United States Patent [19]

Ding et al.

[11] Patent Number: 5,716,834
[45] Date of Patent: Feb. 10, 1998

[54] **CLONED FACTOR C CDNA OF THE SINGAPORE HORSESHOE CRAB, *CARCINOSCORPIUS ROTUNDICAUDA* AND PURIFICATION OF FACTOR C PROENZYME**

[75] Inventors: Jeak Ling Ding; Bow Ho, both of Singapore, Singapore

[73] Assignee: National University of Singapore, Singapore

[21] Appl. No.: 296,014

[22] Filed: Aug. 19, 1994

[51] Int. Cl.[6] .................... C12N 9/50; C12N 15/55; C12N 15/63

[52] U.S. Cl. .................. 435/219; 435/240.2; 435/252.33; 435/254.11; 435/320.1; 536/23.2

[58] Field of Search .................. 435/219, 252.3, 435/320.1, 240.2, 252.33, 254.11; 536/23.2

[56] References Cited

U.S. PATENT DOCUMENTS

| | | | |
|---|---|---|---|
| 4,322,217 | 3/1982 | Dikeman | 435/7.21 |
| 5,082,782 | 1/1992 | Gibson | 435/240.2 |

OTHER PUBLICATIONS

Ho (1983) *Microbios Letters* 24:81–84.
Ho et al. (1985) *Proc. 1st Intl. Cong. Singapore Soc. Microbiol*, pp.664–669.
Kim et al. (1987) Singapore Society for Microbiology, 1987 Annual Scientific Meeting, p. 21.
Ding et al. (1988) *Cytobios* 55:147–154.
Kim et al. (1988) 7th FAOB Symposium, POS–F–01.
Navas et al. (1988) 5 FAOB Congress, MO:19.
Yeo et al. (1989) Second SSM International Congress for Microbiology, BE8.
Navas et al. (1990) *Biochemistry International* 21(5):805–813.
B. Ho et al. (1993) *Biochemistry and Molecular Biology International* 29(4):687–694.
Ding et al (1993) *Biochimica et Biophysica Acta* 1202:149–156.
Ding et al. (1993) *Cytobios* 75:21–32.
Muta et al. (1991) *The Journal of Biological Chemistry* 266(10):6554–6561.
Navas III et al., Proc. 5th FAOB Congress, MO:19, pp. 199 (Aug. 13–18, 1988).
Roopashree et al., Microbiology in the Nineties, pp. 380 (1994).
Ding et al., Biochimica et Biophysica Acta, 1202:149–156 (Sep. 1993).
Ding et al., Essays in Zoology, pp. 337–341 (1990).

*Primary Examiner*—Dian C. Jacobson
*Attorney, Agent, or Firm*—Birch, Stewart, Kolasch & Birch, LLP

[57] ABSTRACT

Full-length and deletion subclones of cDNAs for Factor C of *Carcinoscorpius rotundicauda* are provided. These cDNAs have been cloned into λgt 22 and pGEM 11Zf(+). Further manipulations of the 5' and 3' ends of these cDNAs have been carried out, and these cDNAs have been further subcloned into other expression vectors such as pGEMEX–1, pET 3b, and the yeast shuttle vectors YEpsec 1 and pEMBLyex 4, and pPIC 9 and pHIL D2. Also provided are host cells transformed with expression vectors containing DNA molecules encoding proteins having Factor C-like enzymatic activity, methods of producing such proteins, methods for purifying Factor C zymogens, and methods for protecting Factor C zymogens from autoactivation by Gram negative bacterial endotoxin while the proenzyme is being purified and/or processed from amoebocyte lysates or from recombinant clones, or during storage or subsequent handling. This protection is afforded by the addition of 5–30% $Me_2SO$, which reversibly inhibits the Factor C zymogen.

12 Claims, 45 Drawing Sheets

```
                                       *
                      GTATTTAATGTCTCAACGGTAAAGGTTT     28
CATTGTAGCTAATATTTAACTTCCTCCCTGTGCCCCAAATCGCGAGTATGACGTCAGTTA    88
              *
AGACTTCGTATTTTAAGAGTTAAACACGAGCCTTAAAGAGCGATATTTTTTTGTTAAAC   148
ACTTCCAACTTAATACAATTGGCAAACTTTCAAAAATAAAGTGGAAAAGGAGGTAAAAAA   208
          *
GATGAAAAAAATTCGCATACAATAGAATACAATAAAATGTTGTCTTTACTGTCAACAC   268
                      *
TTACTGTTCGTTCGGTCACAGCTGTGAATCGGGGTGACTTTATGTTTGTAGTGGTCTTAA   328
                *
AAACGGGTACTTGGTTGTTTTGAAAATTTTAAAACCTACATATGATTCTCCTAAAATTTT   388
    *
GTTTATAAATTAGCACCATTTGCGACCTAAATCTTTTTTGTAGTCTTAAGTTTAGTTGAC   448
ATAAAAACAAAATTTGTAACAACACACGGTATAAACTAAATAGCTTCAGATGGGTCGTAT   508
                                              *
GACAAGGAAACTTTTAAATAATTATGAAAGTTTTTTTAAAATTTGACTAAGGTTTAGATT   568
ATGTGGGTGACATGCTTCGACACGTTTCTTTTTGTTTGTGAAAGTTCAGTTTTCTGTTTG   628
 M  W  V  T  C  F  D  T  F  L  F  V  C  E  S  S  V  F  C  L    20
TTGTGTGTGTGGAGGTTTGGTTTCTGTAGGTGGCGTGTTTTCTACAGTTTTCCATTCGTT   688
 L  C  V  W  R  F  G  F  C  R  W  R  V  F  Y  S  F  P  F  V    40
AAGTCAACAGTTGTTTTATTACAGTGTTACCATTACTCTCTCCACAATACCTCAAAGTTC   748
 K  S  T  V  V  L  L  Q  C  Y  H  Y  S  L  H  N  T  S  K  F    60
TACTCTGTGAATCCTGACAAGCCAGAGTACATTCTTTCAGGTTTAGTTCTAGGGCTACTA   808
 Y  S  V  N  P  D  K  P  E  Y  I  L  S  G  L  V  L  G  L  L    80
GCCCAAAAAATGCGCCCAGTTCAGTCCAAAGGAGTAGATCTAGGCTTGTGTGATGAAACG   868
 A  Q  K  M  R  P  V  Q  S  K  G  V  D  L  G  L  C  D  E  T   100
AGGTTCGAGTGTAAGTGTGGCGATCCAGGCTATGTGTTCAACATTCCAGTGAAACAATGT   928
 R  F  E  C  K  C  G  D  P  G  Y  V  F  N  I  P  V  K  Q  C   120
ACATACTTTTATCGATGGAGGCCGTATTGTAAACCATGTGATGACCTGGAGGCTAAGGAT   988
 T  Y  F  Y  R  W  R  P  Y  C  K  P  C  D  D  L  E  A  K  D   140
ATTTGTCCAAAGTACAAACGATGTCAAGAGTGTAAGGCTGGTCTTGATAGTTGTGTTACT  1048
 I  C  P  K  Y  K  R  C  Q  E  C  K  A  G  L  D  S  C  V  T   160
TGTCCACCTAACAAATATGGTACTTGGTGTAGCGGTGAATGTCAGTGTAAGAATGGAGGT  1108
 C  P  P  N  K  Y  G  T  W  C  S  G  E  C  Q  C  K  N  G  G   180
```

FIG. 6A

```
ATCTGTGACCAGAGGACAGGAGCTTGTGCATGTCGTGACAGATATGAAGGGGTGCACTGT    1168
 I  C  D  Q  R  T  G  A  C  R  D  R  Y  E  G  V  H  C           200

GAAATTCTCAAAGGTTGTCCTCTTCTTCCATCGGATTCTCAGGTTCAGGAAGTCAGAAAT    1228
 E  I  L  K  G  C  P  L  L  P  S  D  S  Q  V  Q  E  V  R  N    220

CCACCAGATAATCCCCAAACTATTGACTACAGCTGTTCACCAGGGTTCAAGCTTAAGGGT    1288
 P  P  D  N  P  Q  T  I  D  Y  S  C  S  P  G  F  K  L  K  G    240

ATGGCACGAATTAGCTGTCTCCCAAATGGACAGTGGAGTAACTTTCCACCCAAATGTATT    1348
 M  A  R  I  S  C  L  P  N  G  Q  W  S  N  F  P  P  K  C  I    260

CGAGAATGTGCCATGGTTTCATCTCCAGAACATGGGAAAGTGAATGCTCTTAGTGGTGAT    1408
 R  E  C  A  M  V  S  S  P  E  H  G  K  V  N  A  L  S  G  D    280

ATGATAGAAGGGGCTACTTTACGGTTCTCATGTGATAGTCCCTACTACTTGATTGGTCAA    1468
 M  I  E  G  A  T  L  R  F  S  C  D  S  P  Y  Y  L  I  G  Q    300

GAAACATTAACCTGTCAGGGTAATGGTCAGTGGAATGGACAGATACCACAATGTAAGAAC    1528
 E  T  L  T  C  Q  G  N  G  Q  W  N  G  Q  I  P  Q  C  K  N    320

TTAGTCTTCTGTCCTGACCTGGATCCTGTAAACCATGCTGAACACAAGGTTAAAATTGGT    1588
 L  V  F  C  P  D  L  D  P  V  N  H  A  E  H  K  V  K  I  G    340

GTGGAACAAAAATATGGTCAGTTTCCTCAAGGCACTGAAGTGACCTATACGTGTTCGGGT    1648
 V  E  Q  K  Y  G  Q  F  P  Q  G  T  E  V  T  Y  T  C  S  G    360

AACTACTTCTTGATGGGTTTTGACACCTTAAAATGTAACCCTGATGGGTCTTGGTCAGGA    1708
 N  Y  F  L  M  G  F  D  T  L  K  C  N  P  D  G  S  W  S  G    380

TCACAGCCATCCTGTGTTAAAGTGGCAGACAGAGAGGTCGACTGTGACAGTAAAGCTGTA    1768
 S  Q  P  S  C  V  K  V  A  D  R  E  V  D  C  D  S  K  A  V    400

GACTTCTTGGATGATGTTGGTGAACCTGTCAGGATCCACTGTCCTGCTGGCTGTTCTTTG    1828
 D  F  L  D  D  V  G  E  P  V  R  I  H  C  P  A  G  C  S  L    420

ACAGCTGGTACTGTGTGGGGTACAGCCATATACCATGAACTTTCCTCAGTGTGTCGTGCA    1888
 T  A  G  T  V  W  G  T  A  I  Y  H  E  L  S  S  V  C  R  A    440

GCCATCCATGCTGGCAAGCTTCCAAACTCTGGAGGAGCGGTGCATGTTGTGAACAATGGC    1948
 A  I  H  A  G  K  L  P  N  S  G  G  A  V  H  V  V  N  N  G    460

CCCTACTCGGACTTTCTGGGTAGTGACCTGAATGGGATAAAATCCGAAGAGTTGAAGTCT    2008
 P  Y  S  D  F  L  G  S  D  L  N  G  I  K  S  E  E  L  K  S    480

CTTGCCCGGAGTTTCCGATTCGATTATGTCAGTTCCTCCACAGCAGGTAAATCAGGATGT    2068
 L  A  R  S  F  R  F  D  Y  V  S  S  S  T  A  G  K  S  G  C    500

CCTGATGGATGGTTTGAGGTAGACGAGAACTGTGTGTACGTTACATCAAAACAGAGAGCC    2128
 P  D  G  W  F  E  V  D  E  N  C  V  Y  V  T  S  K  Q  R  A    520
```

FIG. 6B

```
TGGGAAAGAGCTCAAGGTGTGTGTACCAATATGGCTGCTCGTCTTGCTGTGCTGGACAAA    2188
 W   E   R   A   Q   G   V   C   T   N   M   A   A   R   L   A   V   L   D   K     540

GATGTAATTCCAAATTCATTGACTGAGACTCTACGAGGGAAAGGGTTAACAACCACGTGG    2248
 D   V   I   P   N   S   L   T   E   T   L   R   G   K   G   L   T   T   T   W     560

ATAGGATTGCACAGACTAGATGCTGAGAAGCCCTTTATTTGGGAGTTAATGGATCGTAGT    2308
 I   G   L   H   R   L   D   A   E   K   P   F   I   W   E   L   M   D   R   S     580

AATGTGGTTCTGAATGATAACCTAACATTCTGGGCCTCTGGCGAACCTGGAAATGAAACT    2368
 N   V   V   L   N   D   N   L   T   F   W   A   S   G   E   P   G   N   E   T     600

AACTGTGTATATATGGACATCCAAGATCAGTTGCAGTCTGTGTGGAAAACCAAGTCATGT    2428
 N   C   V   Y   M   D   I   Q   D   Q   L   Q   S   V   W   K   T   K   S   C     620

TTTCAGCCCTCAAGTTTTGCTTGCATGATGGATCTGTCAGACAGAAATAAAGCCAAATGC    2488
 F   Q   P   S   S   F   A   C   M   M   D   L   S   D   R   N   K   A   K   C     640

GATGATCCTGGATCACTGGAAAATGGACACGCCACACTTCATGGACAAAGTATTGATGGG    2548
 D   D   P   G   S   L   E   N   G   H   A   T   L   H   G   Q   S   I   D   G     660

TTCTATGCTGGTTCTTCTATAAGGTACAGCTGTGAGGTTCTCCACTACCTCAGTGGAACT    2608
 F   Y   A   G   S   S   I   R   Y   S   C   E   V   L   H   Y   L   S   G   T     680

GAAACCGTAACTTGTACAACAAATGGCACATGGAGTGCTCCTAAACCTCGATGTATCAAA    2668
 E   T   V   T   C   T   T   N   G   T   W   S   A   P   K   P   R   C   I   K     700

GTCATCACCTGCCAAAACCCCCCTGTACCATCATATGGTTCTGTGGAAATCAAACCCCCA    2728
 V   I   T   C   Q   N   P   P   V   P   S   Y   G   S   V   E   I   K   P   P     720

AGTCGGACAAACTCGATAAGTCGTGTTGGGTCACCTTTCTTGAGGTTGCCACGGTTACCC    2788
 S   R   T   N   S   I   S   R   V   G   S   P   F   L   R   L   P   R   L   P     740

CTCCCATTAGCCAGAGCAGCCAAACCTCCTCCAAAACCTAGATCCTCACAACCCTCTACT    2848
 L   P   L   A   R   A   A   K   P   P   P   K   P   R   S   S   Q   P   S   T     760

GTGGACTTGGCTTCTAAAGTTAAACTACCTGAAGGTCATTACCGGGTAGGGTCTCGAGCC    2908
 V   D   L   A   S   K   V   K   L   P   E   G   H   Y   R   V   G   S   R   A     780

ATTTACACGTGCGAGTCGAGATACTACGAACTACTTGGATCTCAAGGCAGAAGATGTGAC    2968
 I   Y   T   C   E   S   R   Y   Y   E   L   L   G   S   Q   G   R   R   C   D     800

TCTAATGGAAACTGGAGTGGTCGGCCAGCGAGCTGTATTCCAGTTTGTGGACGGTCAGAC    3028
 S   N   G   N   W   S   G   R   P   A   S   C   I   P   V   C   G   R   S   D     820

TCTCCTCGTTCTCCTTTTATCTGGAATGGGAATTCTACAGAAATAGGTCAGTGGCCGTGG    3088
 S   P   R   S   P   F   I   W   N   G   N   S   T   E   I   G   Q   W   P   W     840

CAGGCAGGAATCTCTAGATGGCTTGCAGACCACAATATGTGGTTTCTCCAGTGTGGAGGA    3148
 Q   A   G   I   S   R   W   L   A   D   H   N   M   W   F   L   Q   C   G   G     860

TCTCTATTGAATGAGAAATGGATCGTCACTGCTGCCCACTGTGTCACCTACTCTGCTACT    3208
 S   L   L   N   E   K   W   I   V   T   A   A   H   C   V   T   Y   S   A   T     880
```

FIG. 6C

```
GCTGAGATTATTGACCCCAATCAGTTTAAAATGTATCTGGGCAAGTACTACCGTGATGAC    3268
 A  E  I  I  D  P  N  Q  F  K  M  Y  L  G  K  Y  Y  R  D  D      900

AGTAGAGACGATGACTATGTACAAGTAAGAGAGGCTCTTGAGATCCACGTGAATCCTAAC    3328
 S  R  D  D  Y  V  Q  V  R  E  A  L  E  I  H  V  N  P  N        920

TACGACCCCGGCAATCTCAACTTTGACATAGCCCTAATTCAACTGAAAACTCCTGTTACT    3388
 Y  D  P  G  N  L  N  F  D  I  A  L  I  Q  L  K  T  P  V  T     940
                        ✪

TTGACAACACGAGTCCAACCAATCTGTCTGCCTACTGACATCACAACAAGAGAACACTTG    3448
 L  T  T  R  V  Q  P  I  C  L  P  T  D  I  T  T  R  E  H  L     960

AAGGAGGGAACATTAGCAGTGGTGACAGGTTGGGGTTTGAATGAAAACAACACCTATTCA    3508
 K  E  G  T  L  A  V  V  T  G  W  G  L  N  E  N  N  T  Y  S     980
                                          ◆

GAGACGATTCAACAAGCTGTGCTACCTGTTGTTGCAGCCAGCACCTGTGAAGAGGGGTAC    3568
 E  T  I  Q  Q  A  V  L  P  V  V  A  A  S  T  C  E  E  G  Y    1000

AAGGAAGCAGACTTACCACTGACAGTAACAGAGAACATGTTCTGTGCAGGTTACAAGAAG    3628
 K  E  A  D  L  P  L  T  V  T  E  N  M  F  C  A  G  Y  K  K    1020

GGACGTTATGATGCCTGCAGTGGGGACAGTGGAGGACCTTTAGTGTTTGCTGATGATTCC    3688
 G  R  Y  D  A  C  S  G  D  S  G  G  P  L  V  F  A  D  D  S    1040
                        ✪

CGTACCGAAAGGCGGTGGGTCTTGGAAGGGATTGTCAGCTGGGGCAGTCCCAGTGGATGT    3748
 R  T  E  R  R  W  V  L  E  G  I  V  S  W  G  S  P  S  G  C    1060

GGCAAGGCGAACCAGTACGGGGGCTTCACTAAAGTTAACGTTTTCCTGTCATGGATTAGG    3808
 G  K  A  N  Q  Y  G  G  F  T  K  V  N  V  F  L  S  W  I  R    1080

CAGTTCATTTGAAACTGATCTAAATATTTTAAGCATGGTTATAAACGTCTTGTTCCTATT    3868
 Q  F  I  <        1083

ATTGCTTTACTGGTTTAACCCATAAGAAGGTTAACGGGGTAAGGCACAAGGATCATTGTT    3928

TCTGTTTGTTTTTACAAATGGTTCTTTTAGTCAGTGAATGAGAATAGTATCCATTGGAGA    3988

CTGTTACCTTTTATTCTACCTTTTTATATTACTATGCAAGTATTTGGGATATCTTCTACA    4048

CATGAAAATTCTGTCATTTTACCATAAATTTGGTTTCTGGTGTGTGTGTTAAGTCCACCA    4108

CTAGAGAACGATGTAATTTTCAATAGTACATGAAATAAATATAGAACAAATCTATTATAA    4168

AAAAAAAAAAAAAA                                                   4182
```

FIG. 6D

```
                                              GTGAAGGTAACTTAAGT    17

ATGGTCTTAGCGTCGTTTTTGGTGTCTGGTTTAGTTCTAGGGCTACTAGCCCAAAAAATG    77
 M  V  L  A  S  F  L  V  S  G  L  V  L  G  L  L  A  Q  K  M     20

CGCCCAGTTCAGTCCAAAGGAGTAGATCTAGGCTTGTGTGATGAAACGAGGTTCGAGTGT   137
 R  P  V  Q  S  K  G  V  D  L  G  L  C  D  E  T  R  F  E  C     40

AAGTGTGGCGATCCAGGCTATGTGTTCAACATTCCAGTGAAACAATGTACATACTTTTAT   197
 K  C  G  D  P  G  Y  V  F  N  I  P  V  K  Q  C  T  Y  F  Y     60

CGATGGAGGCCGTATTGTAAACCATGTGATGACCTGGAGGCTAAGGATATTTGTCCAAAG   257
 R  W  R  P  Y  C  K  P  C  D  D  L  E  A  K  D  I  C  P  K     80

TACAAACGATGTCAAGAGTGTAAGGCTGGTCTTGATAGTTGTGTTACTTGTCCACCTAAC   317
 Y  K  R  C  Q  E  C  K  A  G  L  D  S  C  V  T  C  P  P  N    100

AAATATGGTACTTGGTGTAGCGGTGAATGTCAGTGTAAGAATGGAGGTATCTGTGACCAG   377
 K  Y  G  T  W  C  S  G  E  C  Q  C  K  N  G  G  I  C  D  Q    120

AGGACAGGAGCTTGTGCATGTCGTGACAGATATGAAGGGGTGCACTGTGAAATTCTCAAA   437
 R  T  G  A  C  A  C  R  D  R  Y  E  G  V  H  C  E  I  L  K    140

GGTTGTCCTCTTCTTCCATCGGATTCTCAGGTTCAGGAAGTCAGAAATCCACCAGATAAT   497
 G  C  P  L  L  P  S  D  S  Q  V  Q  E  V  R  N  P  P  D  N    160

CCCCAAACTATTGACTACAGCTGTTCACCAGGGTTCAAGCTTAAGGGTATGGCACGAATT   557
 P  Q  T  I  D  Y  S  C  S  P  G  F  K  L  K  G  M  A  R  I    180

AGCTGTCTCCCAAATGGACAGTGGAGTAACTTTCCACCCAAATGTATTCGAGAATGTGCC   617
 S  C  L  P  N  G  Q  W  S  N  F  P  P  K  C  I  R  E  C  A    200

ATGGTTTCATCTCCAGAACATGGGAAAGTGAATGCTCTTAGTGGTGATATGATAGAAGGG   677
 M  V  S  S  P  E  H  G  K  V  N  A  L  S  G  D  M  I  E  G    220

GCTACTTTACGGTTCTCATGTGATAGTCCCTACTACTTGATTGGTCAAGAAACATTAACC   737
 A  T  L  R  F  S  C  D  S  P  Y  Y  L  I  G  Q  E  T  L  T    240

TGTCAGGGTAATGGTCAGTGGAATGGACAGATACCACAATGTAAGAACTTGGTCTTCTGT   797
 C  Q  G  N  G  Q  W  N  G  Q  I  P  Q  C  K  N  L  V  F  C    260

CCTGACCTGGATCCTGTAAACCATGCTGAACACAAGGTTAAAATTGGTGTGGAACAAAAA   857
 P  D  L  D  P  V  N  H  A  E  H  K  V  K  I  G  V  E  Q  K    280

TATGGTCAGTTTCCTCAAGGCACTGAAGTGACCTATACGTGTTCGGGTAACTACTTCTTG   917
 Y  G  Q  F  P  Q  G  T  E  V  T  Y  T  C  S  G  N  Y  F  L    300

ATGGGTTTTGACACCTTAAAAATGTAACCCTGATGGGTCTTGGTCAGGATCACAGCCATCC   977
 M  G  F  D  T  L  K  C  N  P  D  G  S  W  S  G  S  Q  P  S    320

TGTGTTAAAGTGGCAGACAGAGAGGTCGACTGTGACAGTAAAGCTGTAGACTTCTTGGAT  1037
 C  V  K  V  A  D  R  E  V  D  C  D  S  K  A  V  D  F  L  D    340
```

FIG. 8A

```
GATGTTGGTGAACCTGTCAGGATCCACTGTCCTGCTGGCTGTTCTTTGACAGCTGGTACT   1097
 D   V   G   E   P   V   R   I   H   C   P   A   G   C   S   L   T   A   G   T       360

GTGTGGGGTACAGCCATATACCATGAACTTTCCTCAGTGTGTCGTGCAGCCATCCATGCT   1157
 V   W   G   T   A   I   Y   H   E   L   S   S   V   C   R   A   A   I   H   A       380

GGCAAGCTTCCAAACTCTGGAGGAGCGGTGCATGTTGTGAACAATGGCCCCTACTCGGAC   1217
 G   K   L   P   N   S   G   G   A   V   H   V   V   N   N   G   P   Y   S   D       400

TTTCTGGGTAGTGACCTGAATGGGATAAAATCGGAAGAGTTGAAGTCTCTTGCCCGGAGT   1277
 F   L   G   S   D   L   N   G   I   K   S   E   E   L   K   S   L   A   R   S       420

TTCCGATTCGATTATGTCCGTTCCTCCACAGCAGGTAAATCAGGATGTCCTGATGGATGG   1337
 F   R   F   D   Y   V   R   S   S   T   A   G   K   S   G   C   P   D   G   W       440

TTTGAGGTAGACGAGAACTGTGTGTACGTTACATCAAAACAGAGAGCCTGGGAAAGAGCT   1397
 F   E   V   D   E   N   C   V   Y   V   T   S   K   Q   R   A   W   E   R   A       460

CAAGGTGTGTGTACCAATATGGCTGCTCGTCTTGCTGTGCTGGACAAAGATGTAATTCCA   1457
 Q   G   V   C   T   N   M   A   A   R   L   A   V   L   D   K   D   V   I   P       480

AATTCGTTGACTGAGACTCTACGAGGGAAAGGGTTAACAACCACGTGGATAGGATTGCAC   1517
 N   S   L   T   E   T   L   R   G   K   G   L   T   T   T   W   I   G   L   H       500

AGACTAGATGCTGAGAAGCCCTTTATTTGGGAGTTAATGGATCGTAGTAATGTGGTTCTG   1577
 R   L   D   A   E   K   P   F   I   W   E   L   M   D   R   S   N   V   V   L       520

AATGATAACCTAACATTCTGGGCCTCTGGCGAACCTGGAAATGAAACTAACTGTGTATAT   1637
 N   D   N   L   T   F   W   A   S   G   E   P   G   N   E   T   N   C   V   Y       540

ATGGACATCCAAGATCAGTTGCAGTCTGTGTGGAAAACCAAGTCATGTTTTCAGCCCTCA   1697
 M   D   I   Q   D   Q   L   Q   S   V   W   K   T   K   S   C   F   Q   P   S       560

AGTTTTGCTTGCATGATGGATCTGTCAGACAGAAATAAAGCCAAATGCGATGATCCTGGA   1757
 S   F   A   C   M   M   D   L   S   D   R   N   K   A   K   C   D   D   P   G       580

TCACTGGAAAATGGACACGCCACACTTCATGGACAAAGTATTGATGGGTTCTATGCTGGT   1817
 S   L   E   N   G   H   A   T   L   H   G   Q   S   I   D   G   F   Y   A   G       600

TCTTCTATAAGGTACAGCTGTGAGGTTCTCCACTACCTCAGTGGAACTGAAACCGTAACT   1877
 S   S   I   R   Y   S   C   E   V   L   H   Y   L   S   G   T   E   T   V   T       620

TGTACAACAAATGGCACATGGAGTGCTCCTAAACCTCGATGTATCAAAGTCATCACCTGC   1937
 C   T   T   N   G   T   W   S   A   P   K   P   R   C   I   K   V   I   T   C       640

CAAAACCCCCCTGTACCATCATATGGTTCTGTGGAAATCAAACCCCCAAGTCGGACAAAC   1997
 Q   N   P   P   V   P   S   Y   G   S   V   E   I   K   P   P   S   R   T   N       660

TCGATAAGTCGTGTTGGGTCACCTTTCTTGAGGTTGCCACGGTTACCCCTCCCATTAGCT   2057
 S   I   S   R   V   G   S   P   F   L   R   L   P   R   L   P   L   P   L   A       680

AGAGCAGCCAAACCTCCTCCAAAACCTAGATCCTCACAACCCTCTACTGTGGACTTGGCT   2117
 R   A   A   K   P   P   P   K   P   R   S   S   Q   P   S   T   V   D   L   A       700

TCTAAAGTTAAACTACCTGAAGGTCATTACCGGGTAGGGTCTCGAGCCATCTACACGTGC   2177
 S   K   V   K   L   P   E   G   H   Y   R   V   G   S   R   A   I   Y   T   C       720

GAGTCGAGATACTACGAACTACTTGGATCTCAAGGCAGAAGATGTGACTCTAATGGAAAC   2237
 E   S   R   Y   Y   E   L   L   G   S   Q   G   R   R   C   D   S   N   G   N       740
```

FIG. 8B

```
TGGAGTGGTCGGCCAGCGAGCTGTATTCCAGTTTGTGGACGGTCAGACTCTCCTCGTTCT   2297
 W  S  G  R  P  A  S  C  I  P  V  C  G  R  S  D  S  P  R  S    760

CCTTTTATCTGGAATGGGAATTCTACAGAAATAGGTCAGTGGCCGTGGCAGGCAGGAATC   2357
 P  F  I  W  N  G  N  S  T  E  I  G  Q  W  P  W  Q  A  G  I    780

TCTAGATGGCTTGCAGACCACAATATGTGGTTTCTCCAGTGTGGAGGATCTCTATTGAAT   2417
 S  R  W  L  A  D  H  N  M  W  F  L  Q  C  G  G  S  L  L  N    800

GAGAAATGGATCGTCACTGCTGCCCACTGTGTCACCTACTCTGCTACTGCTGAGATTATT   2477
 E  K  W  I  V  T  A  A  H  C  V  T  Y  S  A  T  A  E  I  I    820

GACCCCAATCAGTTTAAAATGTATCTGGGCAAGTACTACCGTGATGACAGTAGAGACGAT   2537
 D  P  N  Q  F  K  M  Y  L  G  K  Y  Y  R  D  D  S  R  D  D    840

GACTATGTACAAGTAAGAGAGGCTCTTGAGATCCACGTGAATCCTAACTACGACCCCGGC   2597
 D  Y  V  Q  V  R  E  A  L  E  I  H  V  N  P  N  Y  D  P  G    860

AATCTCAACTTTGACATAGCCCTAATTCAACTGAAAACTCCTGTTACTTTGACAACACGA   2657
 N  L  N  F  D  I  A  L  I  Q  L  K  T  P  V  T  L  T  T  R    880

GTCCAACCAATCTGTCTGCCTACTGACATCACAACAAGAGAACACTTGAAGGAGGGAACA   2717
 V  Q  P  I  C  L  P  T  D  I  T  T  R  E  H  L  K  E  G  T    900

TTAGCAGTGGTGACAGGTTGGGGTTTGAATGAAAACAACACCTATTCAGAGACGATTCAA   2777
 L  A  V  V  T  G  W  G  L  N  E  N  N  T  Y  S  E  T  I  Q    920

CAAGCTGTGCTACCTGTTGTTGCAGCCAGCACCTGTGAAGAGGGGTACAAGGAAGCAGAC   2837
 Q  A  V  L  P  V  V  A  A  S  T  C  E  E  G  Y  K  E  A  D    940

TTACCACTGACAGTAACAGAGAACATGTTCTGTGCAGGTTACAAGAAGGGACGTTATGAT   2897
 L  P  L  T  V  T  E  N  M  F  C  A  G  Y  K  K  G  R  Y  D    960

GCCTGCAGTGGGGACAGTGGAGGACCTTTAGTGTTTGCTGATGATTCCCGTACCGAAAGG   2957
 A  C  S  G  D  S  G  G  P  L  V  F  A  D  D  S  R  T  E  R    980

CGGTGGGTCTTGGAAGGGATTGTCAGCTGGGGCAGTCCCAGTGGATGTGGCAAGGCGAAC   3017
 R  W  V  L  E  G  I  V  S  W  G  S  P  S  G  C  G  K  A  N   1000

CAGTACGGGGGCTTCACTAAAGTTAACGTTTTCCTGTCATGGATTAGGCAGTTCATTTGA   3077
 Q  Y  G  G  F  T  K  V  N  V  F  L  S  W  I  R  Q  F  I  <   1019

AACTGATCTAAATATTTTAAGCATGGTTATAAACGTCTTGTTTCCTATTATTGCTTTACT   3137

AGTTTAACCCATAAGAAGGTTAACTGGGTAAGGCACAAGGATCATTGTTTCTGTTTGTTT   3197

TTACAAATGGTTATTTTAGTCAGTGAATGAGAATAGTATCCATTGAAGACTGTTACCTTT   3257

TATTCTACCTTTTTATATTACTATGTAAGTATTTGGGATATCTTCTACACATGAAAATTC   3317

TGTCATTTTACCATAAATTTGGTTTCTGGTGTGTGCTAAGTCCACCAGTAGAGAACGATG   3377

TAATTTTCACTAGCACATGAAATAAATATAGAACAAATCTATTATAAACTACCTTAAAAA   3437

AAAAAAAAAA   3448
```

FIG. 8C

```
                                                         Start of homology
                                                         ↑
                            GTGAAGGTAACTTAAGTATGGTCTTAGCGTCGTTTTGGTG | TCTGGTTTAGTT
pCrFC21  1   CACGTTTAACGCGAACGTGGAAGAACTCTGAAGTAACTTAAGTATGGTCTTAGCGTCGTTTTGGTG | TCTGGTTTAGTT
pFC53    1   CACGTTTAACGCGAACGTGGAAGAACTCTGAAGTAACTTAAGTATGGTCTTAGCGTCGTTTTGGTG | TCTGGTTTAGTT
pCrFC26  717 ACCATTACTCTCTCCACAATACCTCAAAGTTCTACTCTCTGTGAATCCTGACAAGCCAGAGTACATTCTT | TCAGGTTTAGTT
```

```
GTCAATGAATGAGAATAGTATCCATTGTGACTGTTACCTTTTTATTCTACCTTTTTTATATTACCATGTTTT----------ATGTTTTTTATATTACCATGCAAGTATTTGGAATA 3330
GTCAGTGAATGAGAATAGTATCCATTGTGAAACTGTTACCTTTT----------ATTCTACCTTTTTATATTACATGCAAGTATTTGGATA 3297
GTCAGTGAATGAGAATAGTATCCATTGTGAGACTGTTACCTTTT----------ATTCTACCTTTTTATATTACATGCAAGTATTTGGATA 4039

TCTTCTATACAATATGAAAATTCTGTTTATTTTCCATAAAGTTGGTTTCTG--GTGTGCGTTAAGTCCACCACTGAGAATGATGTAATTT 3418
TCTTC---TACACATGAAAATTCTGTTCATTTTACCATAAATTGGTTTCTGTGCATAAGTCCACCAG--TAGAGAACGATGTAATTT 3383
TCTTCL-TACACATGAAAATTCTGTTCATTTTCATTTTACCATAAATTGGTTTCTGTGTTAAGTCCACCACTAGAGAACGATGTAATTT 4127

TCAATAGTACATGAAATAAATATAGAACAAATCTATTATATAAACTACCTTAAAAAAA 3474
TCACTAGCACATGAAATAAATATAGAACAAATCTATTATATAAACTACCTTAAAAAAAAAAAAAA 3448
TCAATAGTACATGAAATAAATATAGAACAAATCTATTATATAAAAAAAAAAAAAAA 4182
```

FIG. 11I

Averages and values plotted are for that base plus the next 6

```
                                 Hydrophilic      0      Hydrophobic
residue    Score    Avg.     ---------------------.----------------------
   1 M      1.90    0.900                         . *
   2 W     -0.90    0.529                         . *
   3 V      4.20    1.057                         .  *
   4 T     -0.70    1.000                         . *
   5 C      2.50    1.500                         .   *
   6 F      2.80    1.743                         .    *
   7 D     -3.50    1.700                         .    *
   8 T     -0.70    1.700                         .    *
   9 F      2.80    1.686                         .    *
  10 L      3.80    1.171                         .  *
  11 F      2.80    1.229                         .  *
  12 V      4.20    1.229                         .  *
  13 C      2.50    0.986                         . *
  14 E     -3.50    1.171                         .  *
  15 S     -0.80    2.214                         .      *
  16 S     -0.80    2.686                         .       *
  17 V      4.20    3.400                         .          *
  18 F      2.80    2.671                         .       *
  19 C      2.50    1.629                         .    *
  20 L      3.80    1.671                         .    *
  21 L      3.80    1.071                         . *
  22 C      2.50    0.929                         . *
  23 V      4.20    0.929                         . *
  24 W     -0.90   -0.314                      *  .
  25 R     -4.50   -0.314                      *  .
  26 F      2.80   -0.314                      *  .
  27 G     -0.40   -0.114                        *.
  28 F      2.80    0.343                         .*
  29 C      2.50   -0.243                       * .
  30 R     -4.50   -0.714                  *      .
  31 W     -0.90    0.329                         .*
  32 R     -4.50    0.229                       * .
  33 V      4.20    1.271                         .  *
  34 F      2.80    1.271                         .  *
  35 Y     -1.30    0.314                         .*
  36 S     -0.80    0.386                         .*
  37 F      2.80    0.400                         .*
  38 P     -1.60    0.600                         . *
  39 F      2.80    1.429                         .  *
  40 V      4.20    1.571                         .  *
  41 K     -3.90    1.514                         .  *
  42 S     -0.80    1.571                         .  *
  43 T     -0.70    2.043                         .    *
  44 V      4.20    1.957                         .    *
  45 V      4.20    0.900                         . *
  46 L      3.80    0.114                       *  .
  47 L      3.80   -0.543                    *     .
  48 Q     -3.50   -0.543                    *     .
  49 C      2.50   -0.500                     *    .
  50 Y     -1.30   -1.357              *           .
  51 H     -3.20   -1.271               *          .
  52 Y     -1.30   -0.929                 *        .
  53 S     -0.80   -1.300                *         .
  54 L      3.80   -0.786                  *       .
  55 H     -3.20   -1.514              *           .
  56 N     -3.50   -1.171                *         .
  57 T     -0.70   -0.071                       *. 
  58 S     -0.80   -0.471                     *    .
  59 K     -3.90   -0.586                    *     .
```

Fig. 12

CLONED FACTOR C CDNA OF THE SINGAPORE HORSESHOE CRAB, *CARCINOSCORPIUS ROTUNDICAUDA* AND PURIFICATION OF FACTOR C PROENZYME

BACKGROUND OF THE INVENTION

1. Field of the Invention

The present invention relates to cloned cDNAs of *Carcinoscorpius rotundicauda* Factor C useful in the production of Factor C for endotoxin assays and as probes for detecting Factor C genes in other genera and species, Factor C proteins per se, the purification of Factor C proenzyme, and methods for maintaining Factor C, either naturally-occurring or produced via recombinant methods, in its zymogen form.

2. Description of Related Art

There are four extant species of horseshoe crabs: *Limulus polyphemus, Tachypleus tridentatus, Tachypleus gigas* and *Carcinoscorpius rotundicauda*. Within the predominant type of blood cell, i.e., amoebocytes, are enzymes which are activated in the presence of Gram negative bacterial endotoxin, resulting in the final conversion of soluble coagulogen to coagulin clot (FIG. 1). This cascade of enzymes and coagulogen constitutes the commercially available amoebocyte lysate employed for detection of endotoxin. The latter is extremely ubiquitous and indomitable, contaminating parenteral preparations, water, food and pharmaceutical products. The endotoxin also forms the basis of the detection of some Gram negative bacterial infections such as gonorrhoea and meningitis. The Limulus amoebocyte lysate (LAL) constitutes a most rapid and sensitive in vitro assay for detection of femtogram levels of endotoxin (Ho. B, 1983. *Microbios Letts.* 24, 81–84). This diagnostic test for endotoxin forms a crucial FDA-approved pyrogen test which is an integral aspect of quality assurance of many pharmaceutical preparations, especially injectables/parenterals.

Although the production and application of the LAL has become more standardized in recent years (Associates of Cape Cod, Woodshole, Mass., USA, and M. A. Bioproducts, Walkersville, Md., USA), significant variations occur in lysates produced by different manufacturers and even from lot-to-lot within batches produced by individual manufacturers (Ho et al., 1993. *Biochem. & Mol. Biol. Intl.* 29 [4], 687–694). Although the U.S. Limulus population appears unaffected by commercialization, their number could be diminished by overutilization and deterioration of habitat. The Japanese *T. tridentatus* has been pronounced an endangered species and is on its way to extinction (Sekiguchi, K. & Nakamura, K. 1979. In: *Biomedical Applications of the Horseshoe Crabs (Limulidae)*, E. Cohen et al., eds., pp. 37–45, Alan R. Liss, Inc., New York). The availability of a second generation genetically-engineered lysate enzyme receptive to endotoxin, viz., Factor C, would alleviate problems of batch-variation, and also provide a standardized and continuous supply of material for endotoxin/pyrogen assays. This may be achieved through recombinant DNA technology.

Interest in the cloning of Factor C is not new. Japanese workers (Muta et al., 1991, *J. Biol. Chem.* 266, 6554–6561) have cloned the *T. tridentatus* Factor C gene. However, the *T. tridentatus* Factor C gene was cloned in two partial overlapping fragments in separate recombinants (pFC 41 and pFC 53) and reported as a composite DNA sequence totalling 3474 bp.

The potential applications of the genetically-engineered Factor C gene lies in the many possible ways of manipulating and subcloning this gene into a variety of vectors of choice in order to achieve optimum levels of expression of the recombinant Factor C. The biotechnological implications of the resulting recombinant lysate enzyme cannot be overemphasized. Factor C is, afterall, the first enzyme in the amoebocyte lysate coagulation cascade which is activated by endotoxin, which it detects. The recombinant Factor C enzyme may be employed in a chromogenic assay. Upon activation by endotoxin, Factor C converts the substrate to a colored product, thereby detecting and quantifying the endotoxin.

SUMMARY OF THE INVENTION

Accordingly, it is an object of the present invention to provide an isolated, purified DNA molecule comprising a nucleotide sequence that encodes a protein having the same enzymatic activity as Factor C protein in assays for Gram negative bacterial endotoxin. The Factor C protein can be a *Carcinoscorpius rotundicauda* Factor C protein comprising an amino acid sequence selected from the group consisting of SEQ ID NO:2 and SEQ ID NO:4. Said DNA molecule can comprise a nucleotide sequence selected from the group consisting of SEQ ID NO:1 and SEQ ID NO:3, or can comprise a nucleotide sequence selected from the group consisting of a nucleotide sequence that hybridizes to a DNA molecule encoding amino acid sequence SEQ ID NO:2 or SEQ ID NO:4 under salt and temperature conditions equivalent to 5×SSC and 42° C, and that codes on expression for a protein that has the same enzymatic activity as Factor C protein in assays for detecting Gram negative bacterial endotoxin, a nucleotide sequence that is functionally equivalent to a DNA molecule encoding amino acid SEQ ID NO:2 or SEQ ID NO:4 due to the degeneracy of the genetic code and that codes on expression for a protein that has the same enzymatic activity as Factor C protein in assays for detecting Gram negative bacterial endotoxin, and a nucleotide sequence that is functionally equivalent to a DNA molecule encoding amino acid SEQ ID NO:2 or SEQ ID NO:4 in that it codes on expression for a protein in which one or more amino acids has or have been added, deleted, or substituted, but which has the same enzymatic activity as Factor C protein in assays for detecting Gram negative bacterial endotoxin. Said DNA molecule can also comprise the nucleotide sequence of SEQ ID NO:1, wherein nucleotides 1 to 568 have been deleted.

Another object of the present invention is to provide a recombinant vector comprising any of the aforementioned DNA molecules. The vector portion can be a member selected from the group consisting of λgt 22, pGEM 11Zf (+), pGEMEX-1, pET 3b, YEpsec 1, pEMBLyex 4, pIC 9, and pHIL D2.

Another object of the present invention is to provide a host cell transformed with said recombinant vector. Said host cell can be selected from the group consisting of bacteriophage λ, Baculovirus, *E. coli*, a mammalian cell, and a yeast.

Another object of the present invention is to provide a method of producing a protein having the same enzymatic activity as Factor C protein in assays for Gram negative bacterial endotoxin, comprising culturing said host cell under conditions in which said DNA molecule is expressed, and recovering said protein.

Another object of the present invention is to provide an isolated, purified protein molecule comprising an amino acid sequence selected from the group consisting of SEQ ID NO:2, SEQ ID NO:4, a protein molecule comprising an amino acid sequence that is functionally equivalent to SEQ ID NO:2, in which one or more amino acids has or have been added, deleted, or substituted, but which has the same enzymatic activity as Factor C protein in assays for detecting Gram negative bacterial endotoxin, and a protein molecule comprising an amino acid sequence that is functionally equivalent to SEQ ID NO:4, in which one or more amino acids has or have been added, deleted, or substituted, but which has the same enzymatic activity as Factor C protein in assays for detecting Gram negative bacterial endotoxin.

A further object of the present invention is to provide a process for purifying Factor C zymogens, comprising the steps of:

(a) providing an amoebocyte lysate;

(b) fractionating said amoebocyte lysate of step (a) by affinity chromatography employing a buffer containing dimethylsulfoxide and a chelating agent, and pooling fractions for each peak;

(c) desalting said fractions of step (b) by gel filtration chromatography, and pooling fractions for each peak;

(d) fractionating said fractions of step (c) by affinity chromatography, to obtain a fraction containing purified single-chain Factor C and fractions containing double-chain Factor C;

(e) recovering said purified single-chain Factor C;

(f) further fractionating said fractions of step (d) containing double-chain Factor C by gel filtration chromatography to obtain a fraction containing purified double-chain Factor C; and (g) recovering said purified double-chain Factor C.

A further object of the present invention is to provide a method for maintaining Factor C in its zymogen form in a crude amoebocyte lysate, comprising lysing amoebocytes in a solution comprising dimethylsulfoxide and, optionally, a chelating agent.

Yet a further object of the present invention is to provide a method for maintaining Factor C expressed by transformed host cells grown in a culture medium in its zymogen form, comprising contacting said Factor C with dimethylsulfoxide and, optionally, a chelating agent, and subsequently isolating said Factor C in the presence of dimethylsulfoxide and, optionally, a chelating agent. Said Factor C can be accumulated intracellularly within said host cells, and said contacting can be performed by lysing said host cells in the presence of dimethyl-sulfoxide and, optionally, a chelating agent. Said Factor C can also be secreted into said culture medium, and said contacting can be performed by adding dimethylsulfoxide and, optionally, a chelating agent to said culture medium prior to isolating said Factor C.

A still further object of the present invention is to provide a method for maintaining Factor C in its zymogen form, comprising contacting said Factor C with dimethylsulfoxide.

A final object of the present invention is the use of the DNA molecules disclosed herein in recombinant processes to produce proteins having the same enzymatic activity as Factor C protein in assays for Gram negative bacterial endotoxin, and as probes for detecting Factor C genes in species other than *Carcinoscorpius rotundicauda*.

Variant forms of Factor C cDNA of the Singaporean estuarine horseshoe crab, *Carcinoscorpius rotundicauda*, have been cloned into the bacteriophage vector λgt 22 and other vectors. These forms have been mapped and sequenced. One of the recombinant clones, λCrFC 26, contains a full-length Factor C cDNA insert of 4182 bp. It includes 568 bp of 5' untranslated sequence containing seven false start ATGs. The open reading frame codes for a signal peptide of 24 amino acids, followed by 1059 residues of the mature Factor C enzyme. There are six potential glycosylation sites and a typical serine protease catalytic triad of Asp-His-Ser in the mature enzyme. The cDNA terminates with 365 bp of 3' untranslated sequence. In comparison with the *Tachypleus tridentatus* Factor C (TtFC) cDNA, there are notable differences in the restriction sites, and subtle base substitutions in the CrFC cDNA. Whereas λCrFC 26 (4182 bp) cDNA has numerous stem-loop structures, thus obscuring its real start codon, another clone, λCrFC 21 (3448 bp) cDNA, has a well-exposed ATG start site. For ease of manipulation, these cDNAs have been recloned into pGEM 11Zf(+). After manipulations of the 5' and 3' ends of the Factor C cDNAs, the major portions of the cDNAs have been subcloned into expression vectors like pGEMEX-1 and pET 3b. The Factor C cDNA has also been recloned into yeast shuttle secretory (YEpsec 1) and non-secretory (pEMBLyex 4) expression vectors. The full-length CrFc 26 and CrFC 21 cDNAs have been excised from their pGEM11Zf(+) vectors and subkloned into Pichia expression vectors pPIC 9 and pHIL-D2.

Using the T$_7$ promoter in pGEMEX-1 and pET 3b, the CrFC cDNA constructs have been expressed in vitro in the cell-free transcription and translation coupled T$_7$ expression system.

Further scope of the applicability of the present invention will become apparent from the detailed description and drawings provided below. However, it should be understood that the detailed description and specific examples, while indicating preferred embodiments, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 6 shows the complete DNA sequence (SEQ ID NO:1) and deduced amino acid sequence (SEQ ID NO:2) of *C. rotundicauda* Factor C, CrFC 26. The putative signal peptide constitutes the first 24 amino acids. The site of truncation of the signal peptide is indicated by an arrowhead (▲). The potential glycosylation sites are marked with closed diamonds (♦). The amino acid residues constituting the catalytic triad by analogy with trypsin are indicated by (●). A total of 4 polyadenylation sites (AATAAA) were found in CrFC (two at the 5' noncoding sequence, another within the open reading frame, and the last one at the 3' untranslated region), and each is marked with double underlines (__). The seven false start ATG sites found upstream of the authentic ATG site are indicated with single underlines (_). These sites are terminated shortly by in-frame stop codons (★) located several bases downstream. The cleavage site of the Factor C enzymes into heavy and light chain intermediates is indicated by a hollow thick arrow (⇨) between residues R and S, while proteolysis of the light chain into A and B chains due to endotoxin activation is indicated by a solid thick arrow (➡) between the unique phe-ileu site, F and I.

FIG. 8 shows the DNA sequence (SEQ ID NO:3) and deduced amino acid sequence (SEQ ID NO:4) of CrFC 21. The symbols used to denote the potential glycosylation sites, the catalytic triad, the polyadenylation sites, cleavage site of heavy and light chains (between residues R and S), and the proteolytic site of the light chain into A and B chains (between residues F and I) are similar to those described in FIG. 6.

FIG. 9 shows a comparison of the N terminal nucleotide sequences of different Factor C cDNAs isolated from the horseshoe crabs. The clone pFC53 is from *T. tridentatus* (Muta et al., 1991. *J. Biol. Chem.* 266, 6554–6561), while clones CrFC 21 and CrFC 26 are from *C. rotundicauda* (this work). CrFC 21 and pFC53 have identical 5' end sequences, while CrFC 26 has an extra 716 nucleotides at its 5' end.

Figure 11A:
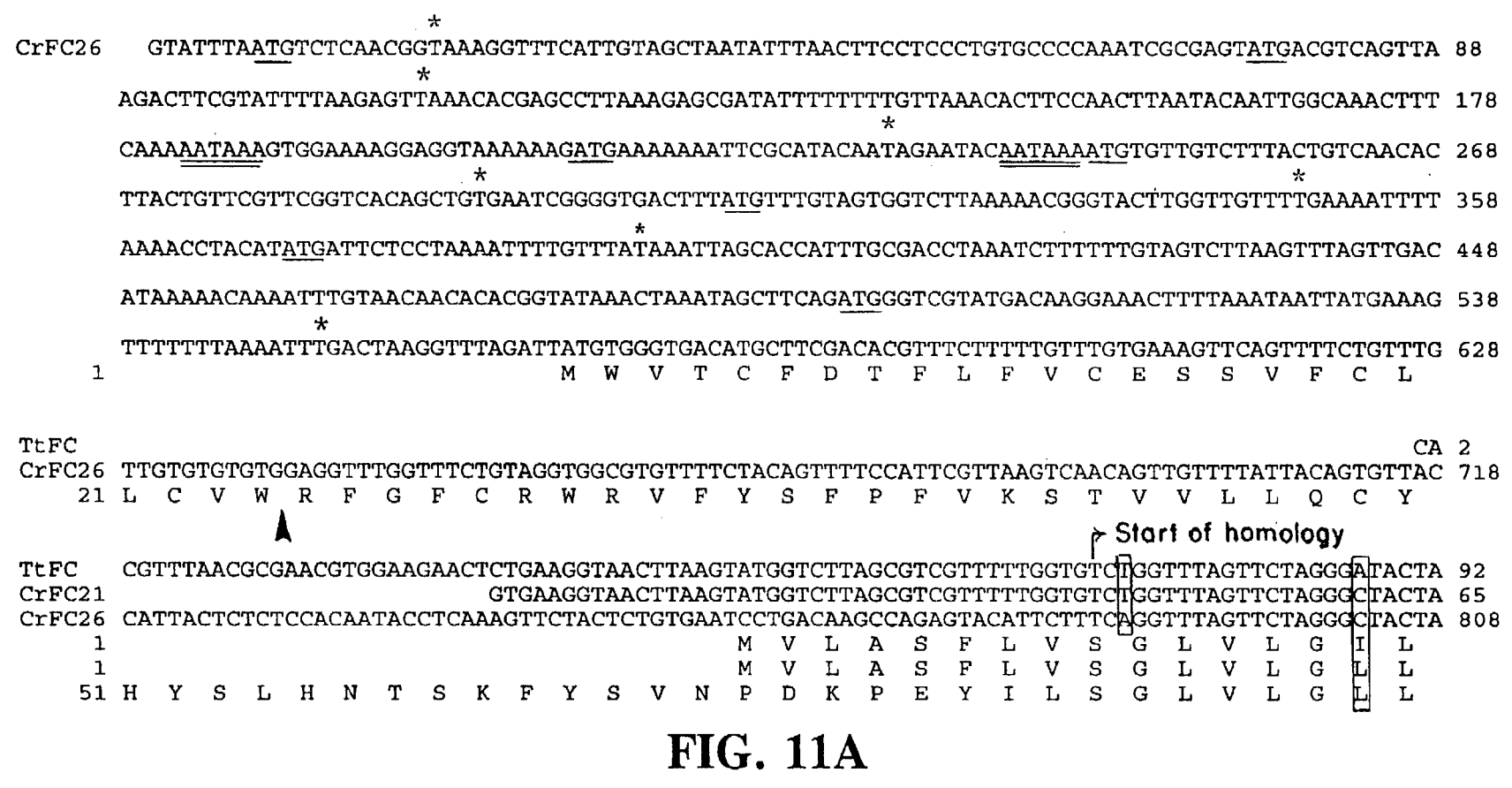
Figure 11B:
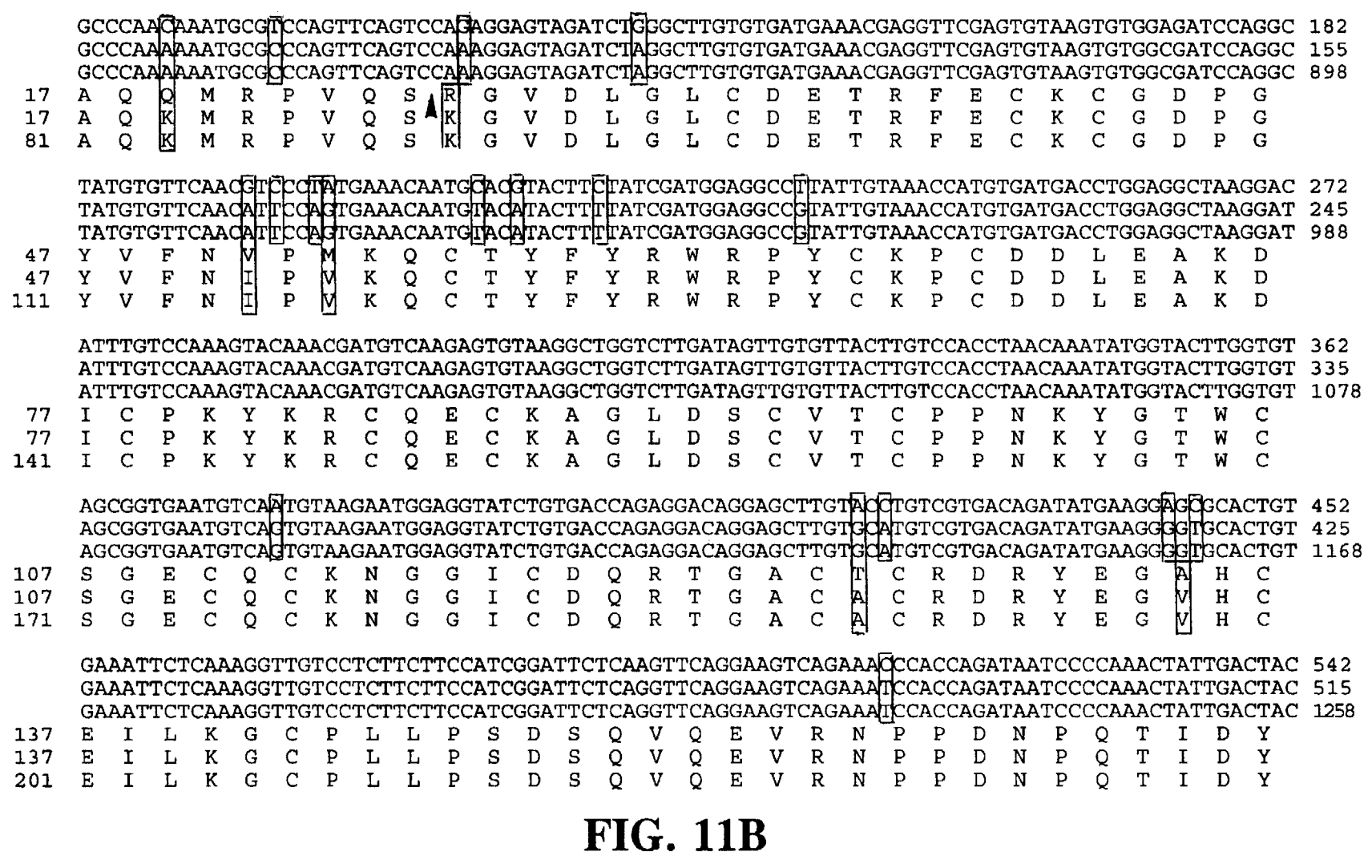
Figure 11C:
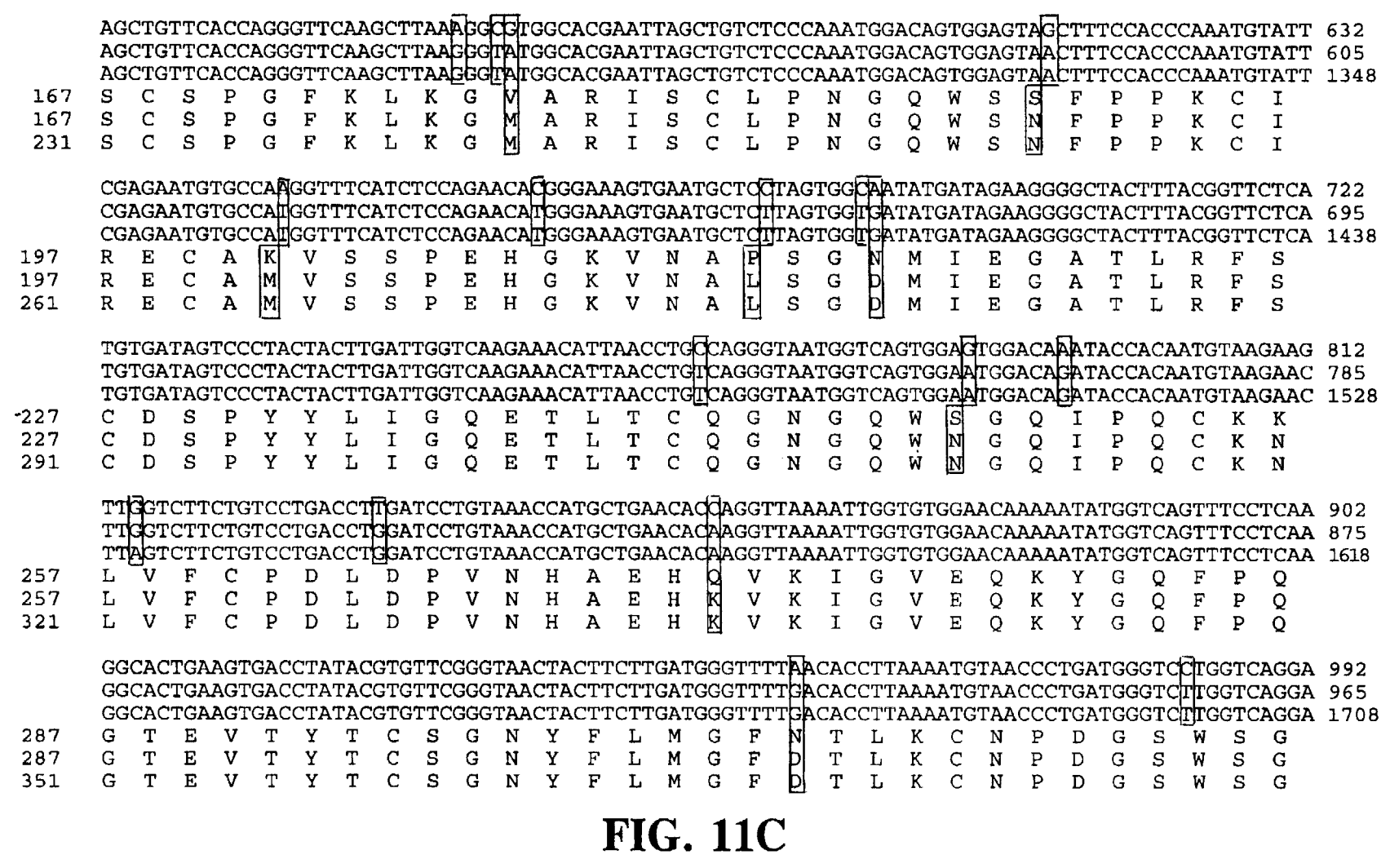
Figure 11D:
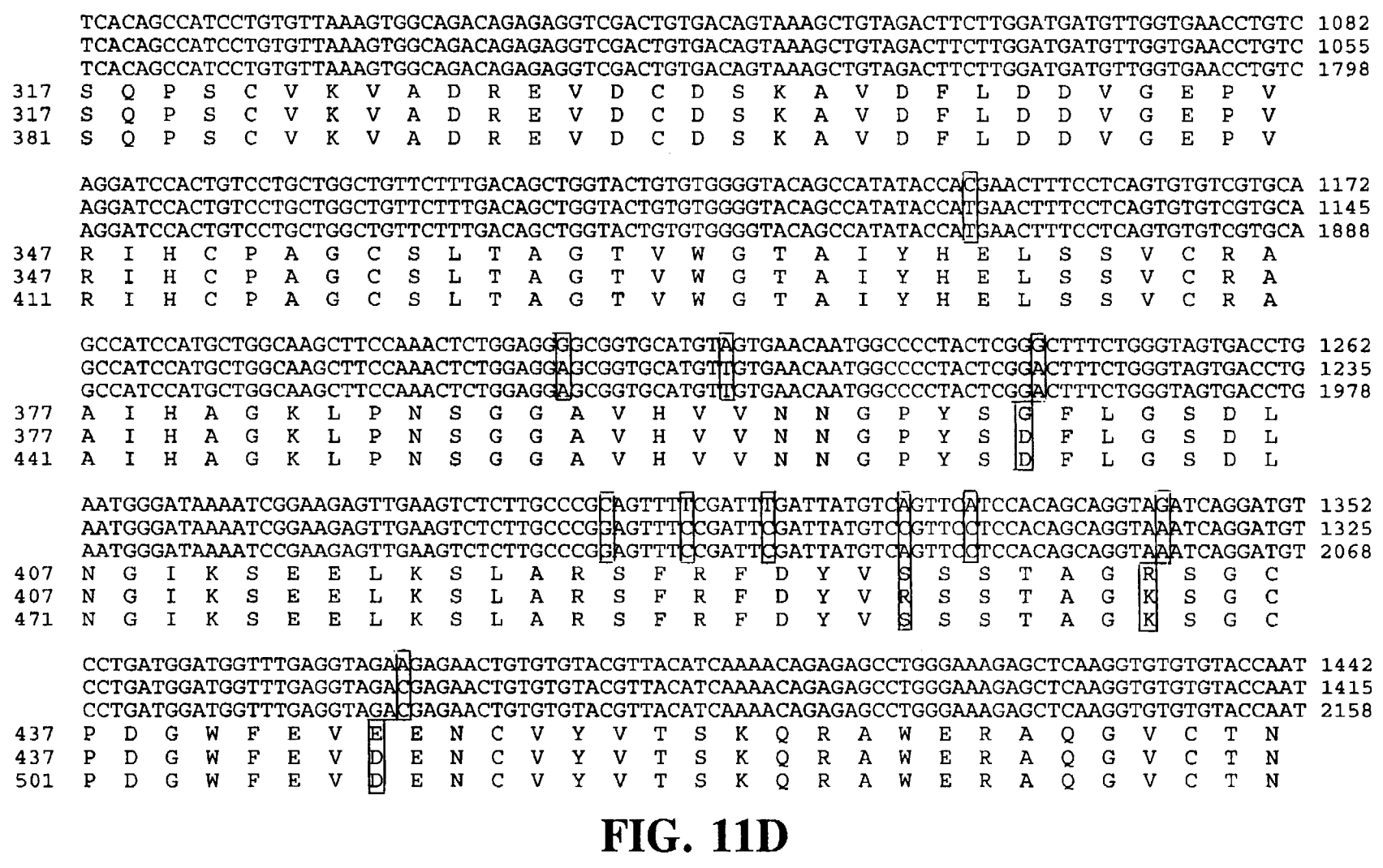
Figure 11E:
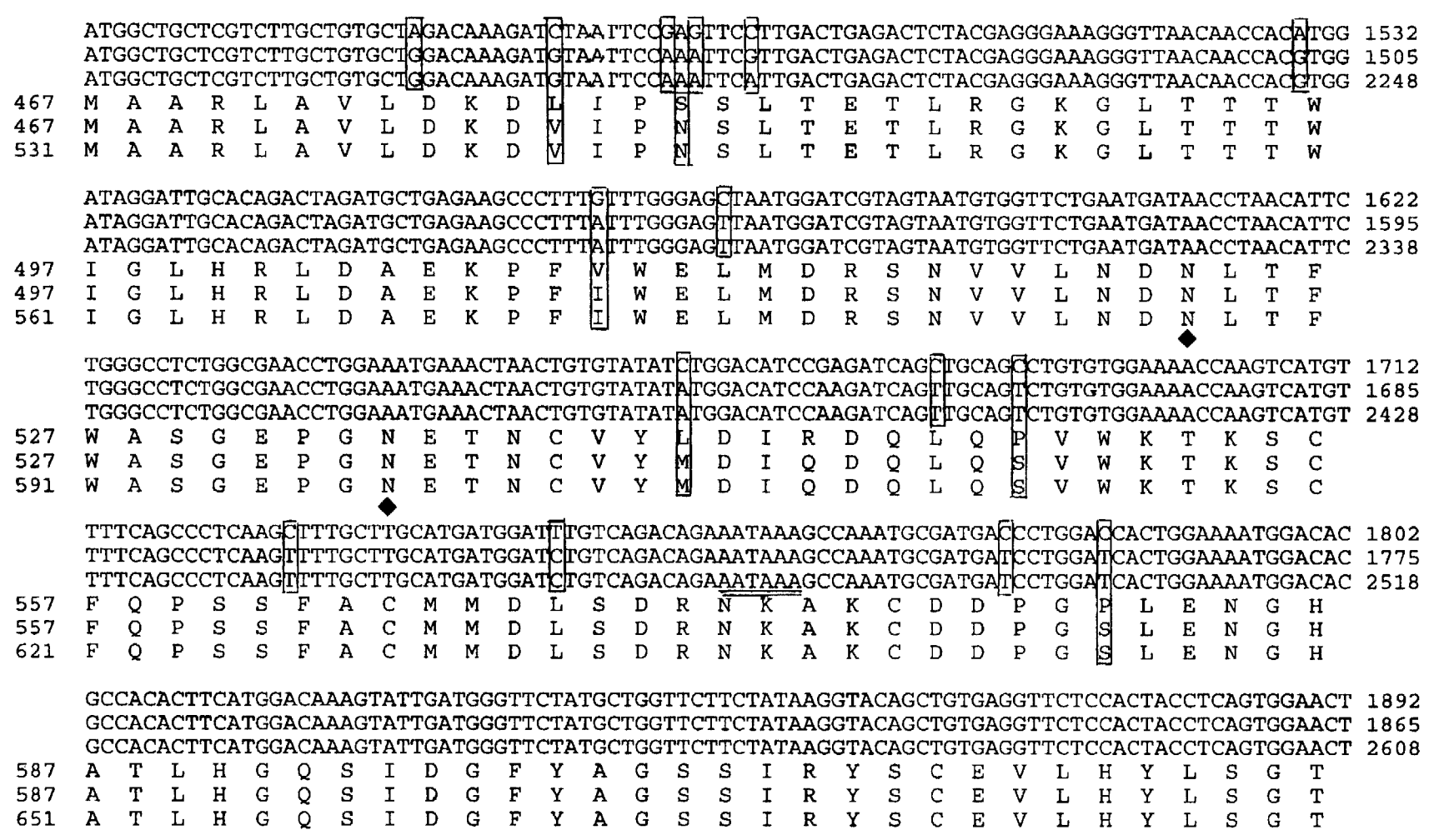
Figure 11F:
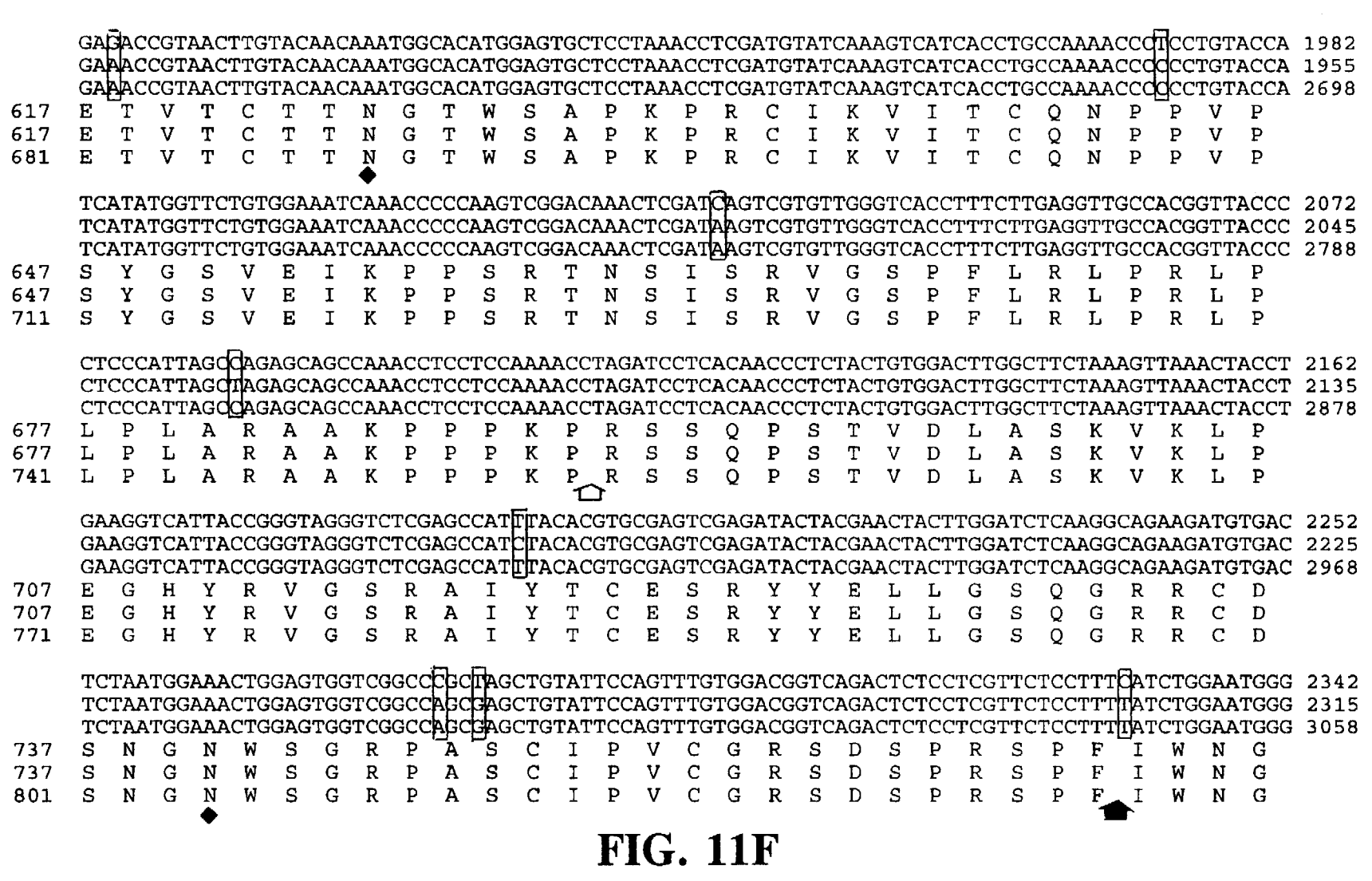
Figure 11G:
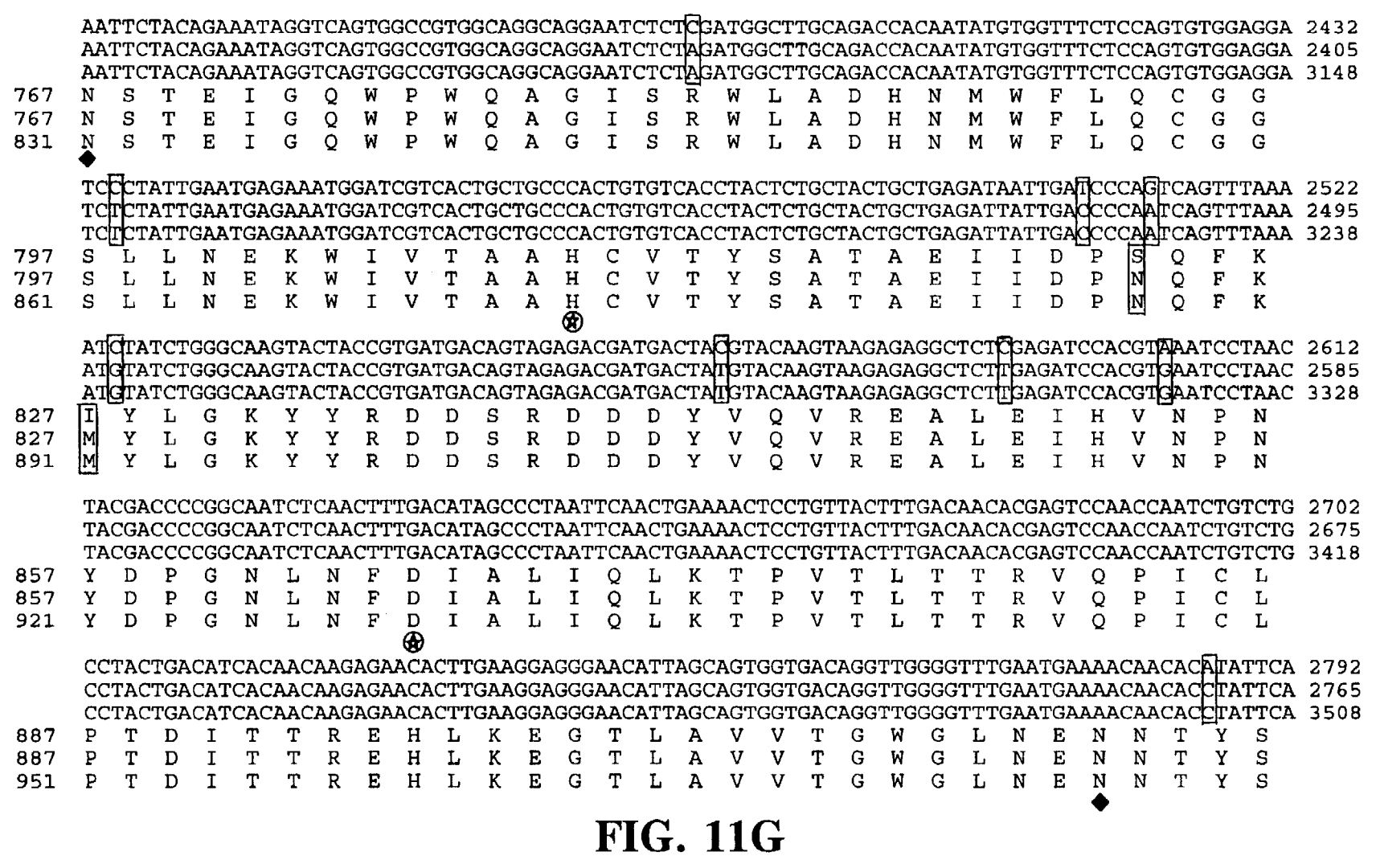
Figure 11H:
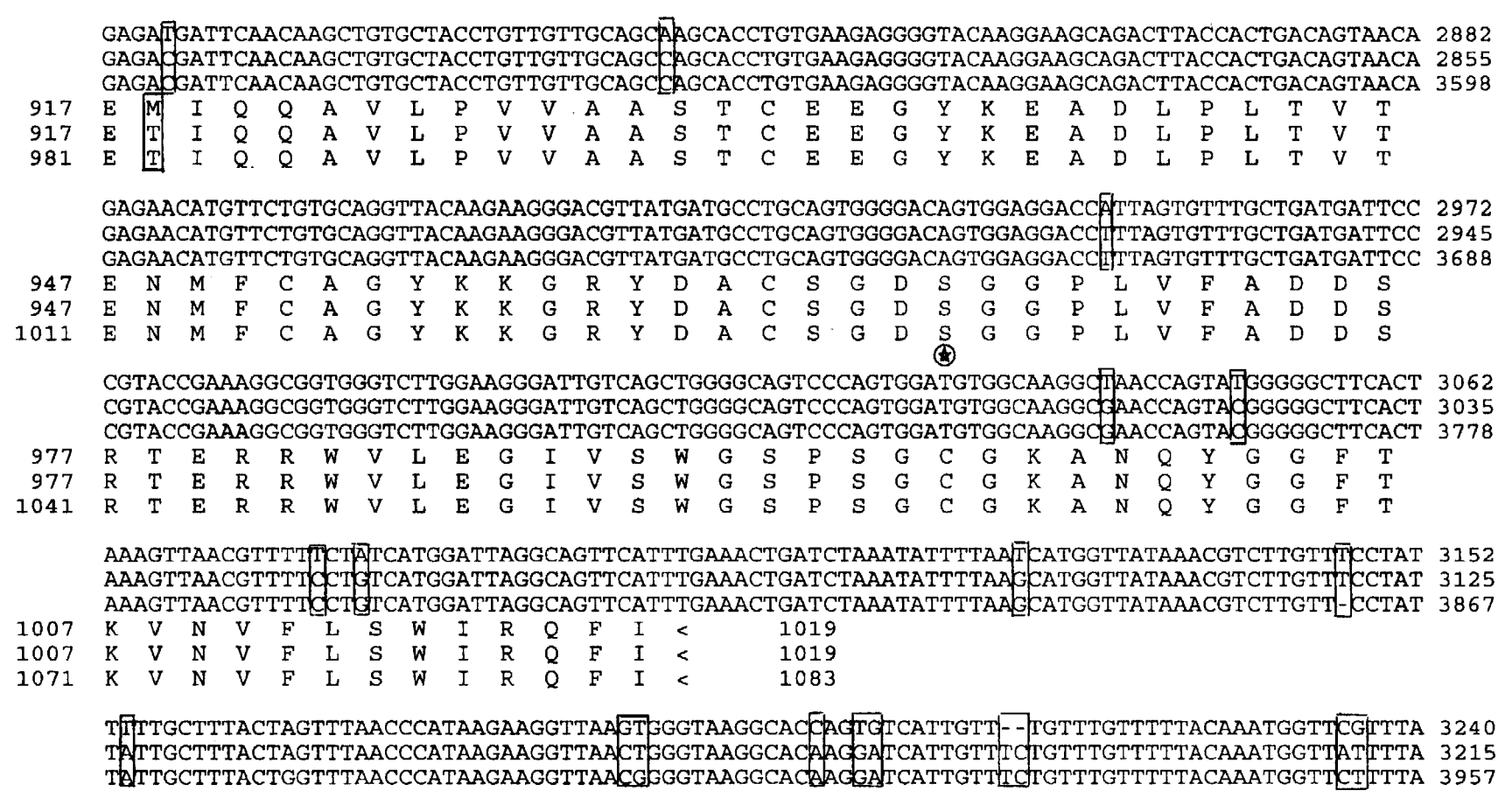

FIG. 11 shows the alignment of the complete DNA sequence and deduced amino acid sequence of *C. rotundicauda* Factor C (CrFC 26 and CrFC 21) with the Factor C of *T. tridentatus* (TtFC, adapted from Muta et al. 1991. *J. Biol. Chem.* 266, 6554–6561). The numbering of the amino acid residues is found at the left, while that of the DNA (in bp) is found at the right. The site of truncation of the signal peptide is indicated by a small arrow head (▲). The "start of homology" region is indicated by a directional arrow (↣). The differences in both the DNA and amino acid sequences are boxed (□). The cleavage site of the Factor C enzymes into heavy and light chain intermediates occurs between residues R and S, indicated by a hollow thick arrow (⇨). Proteolysis of the light chain into A and B subunits due to endotoxin activation is indicated by a solid thick arrow (➡) between F and I. The remaining symbols are as per legend to FIG. 6.

FIG. 12 shows hydropathy analysis of the first 59 deduced amino acid sequence of CrFC 26. The peak spanning residues 1–24 represents the putative signal sequence.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are herein incorporated by reference in their entirety.

Cloning of the *Carcinoscorpius rotundicauda* Factor C cDNA

Figure 1:
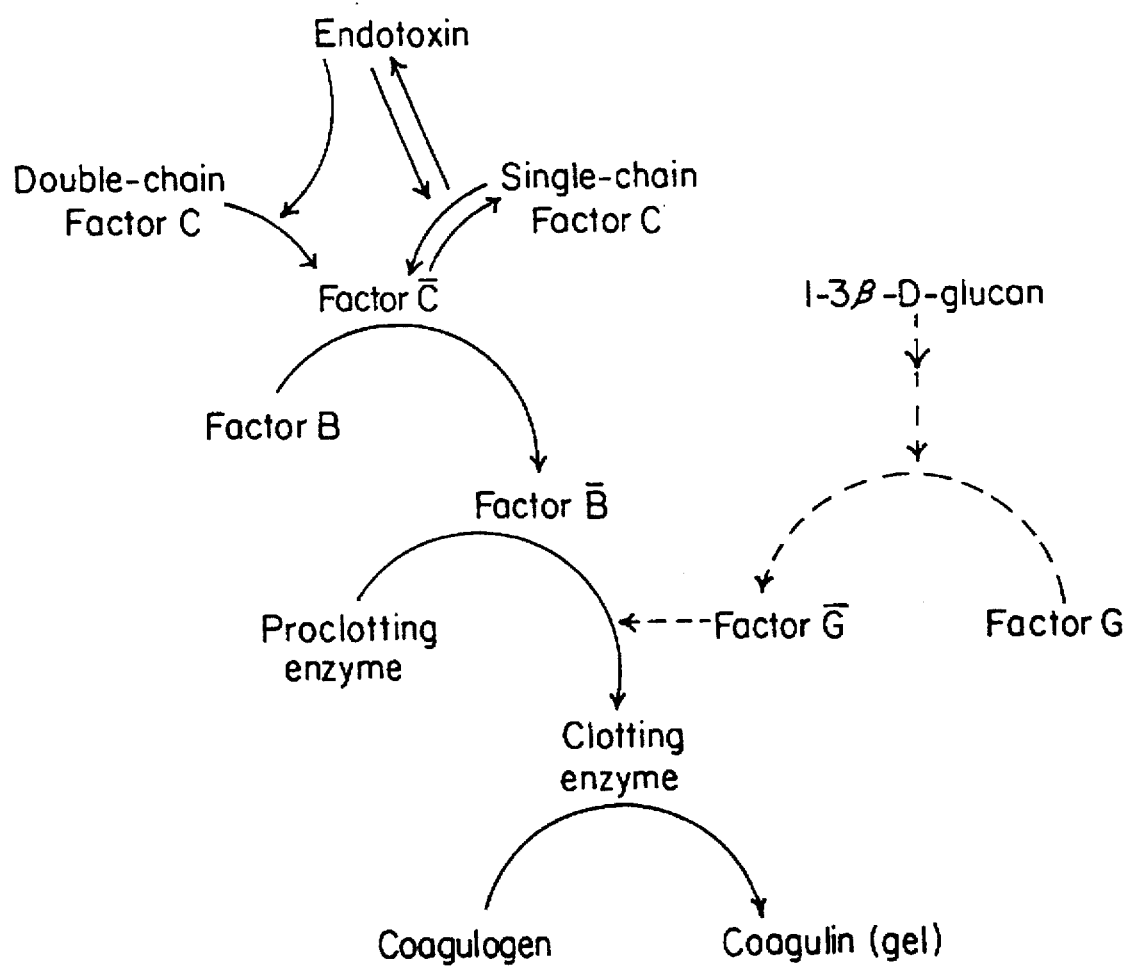
FIG. 1 shows the coagulation cascade reactions in amoebocytes of *C. rotundicauda*. Endotoxin activates both forms of Factor C. Single-chain Factor C exhibits a reversible activation reaction which signifies a form of feedback regulation in the coagulation cascade (Ding et al., 1993. *Biochim. et Biohphys. Acta*, 1202, 149–156). Double-chain Factor C follows a path previously described in *T. tridentatus* (Iwanaga, S. et al., 1985. In: *Microbiology*, Levie et al., eds., pp. 21–24, Am. Soc. Microbiol., Washington). The broken arrows show an alternative pathway of activation of pro-clotting enzyme by 1–3 β glucan.
Figure 2:
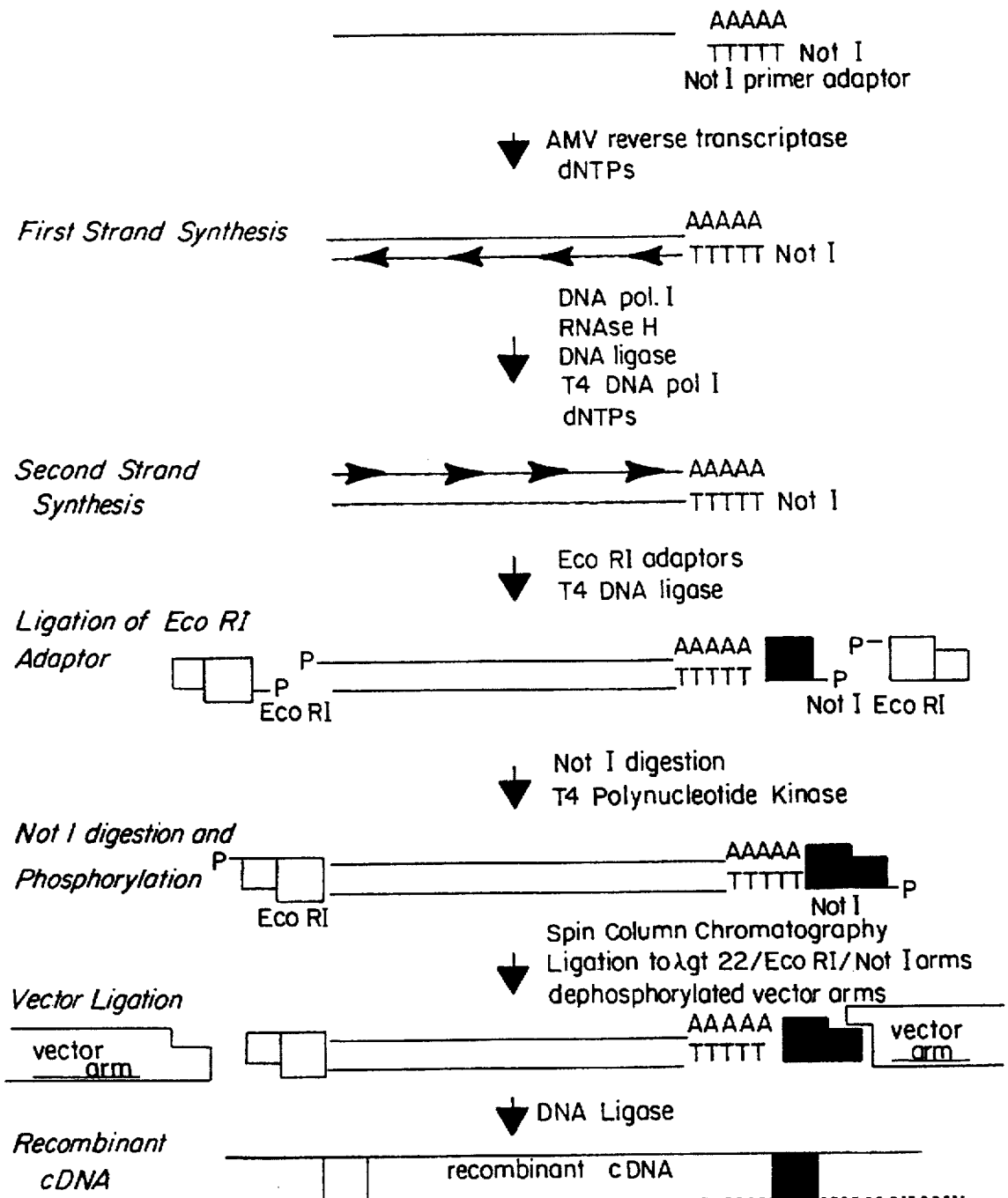
FIG. 2 shows the overall strategy utilized for the synthesis and cloning of the amoebocyte cDNA. Not I primer adaptors were used to prime the first strand synthesis and allow orientation-specific or directional ligation into the vector, bacteriophage λgt 22. A replacement reaction was employed for the second strand synthesis reaction using RNAse H, DNA pol I, and DNA ligase, while Eco RI adaptors were used to produce a sticky ended double-stranded cDNA. After digestion with Not I, the unique restriction ends were phosphorylated with T4 kinase to allow directional ligation to the dephosphorylated Eco RI-Not I digested vector arms. After packaging in vitro, the phage particles were transduced into bacterial host cells (*E. coli* LE392 and Y1090) for subsequent propagation or cloning.

EXAMPLE 1
Construction of Factor C cDNA λ Recombinant Clones
Poly (A)⁺ RNA Preparation From 2.5 g wet weight of amoebocytes, total RNA was purified by using guanidinium isothiocynate (Chirgwin et al., 1987. *Biochemistry* 18, 6294–5299) and ultracentrifugation through a CsCl gradient. The total cellular RNA was digested with RNase-free DNase I (BRL) and extracted with phenol/chloroform. Poly (A)⁺ RNA was purified by chromatography through Oligo-dT Tris Acryl (IBF, France).
cDNA Synthesis and Cloning The mRNAs purified from amoebocytes were used to synthesize cDNAs following a modification of the method of Gubler and Hoffman, 1983 (*Gene* 25, 263–269). Not I primer adaptors were used to prime the first strand cDNA synthesis to ensure orientation-specific ligation to λgt 22 (Promega, USA). A replacement reaction was employed for the second strand synthesis, while Eco RI adaptors were used to produce sticky-ended ds cDNAs. After digestion with Not I, the ds cDNAs flanked by Eco RI-Not I restriction sites were ligated to Eco RI-Not I digested λgt 22 vector arms. The recombinant DNA was packaged and transduced into *E. coli* LE 392 and Y1090. The cloning strategy is outlined in FIG. 2.
Screening of λgt 22 cDNA Library The λgt 22 cDNA library was screened, using as probe, *T. tridentatus* Factor C cDNA (pFC 53, also referred to as λFC 53), which is a partial fragment of the Factor C cDNA (Muta et al., 1991. *J. Biol. Chem.* 266, 6554–6561).

A. Primary Screening

1. Plating of Amoebocyte cDNA Library and Blotting to Nylon Membranes

Plating bacteria (*E. coli* LE392) were propagated in LB medium supplemented with 100mM $MgSO_4$ and 0.2% maltose (w/v). Cultures were grown to an $OD_{600}$ of 0.6. In order to obtain approximately 250,000 pfu of the amoebocyte cDNA library on a Bioassay plate, (245×245 mm, Nunc), 14 µl of the undiluted phage stock containing $1.88 \times 10^7$ pfu/ml were mixed in a 50 ml Nunc centrifuge tube with 2 ml of plating bacteria. The mixture was then incubated at 37° C. for 20 min. to allow the phage particles to adsorb onto the host cells. Maltose is essential for bacterial expression of the lam b gene, which codes for the phage receptors, while magnesium ions facilitate the adsorption of phage particles to these receptors at 37° C. Thirty ml of molten top agarose were then added, and this was immediately mixed and poured onto LB bottom agar supplemented with 1 mM $MgSO_4$. The plate was incubated at 37° C. until the plaques were large enough to contain sufficient DNA for detection, but at the same time were not confluent with each other to allow easy plaque purification. A duplicate plate was similarly prepared to give a screening base of about 500,000 clones. Once the expedient phage size and confluency were achieved, incubation was terminated and the plates were transferred to 4° C. for 1 h. This allows the plaques to absorb enough moisture for them to stick properly to the filters during the blotting step.

A 1.2 µm nylon membrane (22×22 cm, Pall Biodyne A) was randomly labelled with a ballpoint pen on the four sides of one face and then applied face down (ink side up) on each of the two plates. The bottoms of each plate were then accurately marked corresponding to those found on the filters to record the orientation of the filters on the master plate. The filters were left for 2 min. to allow the phage particles to adsorb onto them. The filters were then peeled off slowly from one corner using a pair of forceps with flat ends, and subsequently air dried face up for at least 10 min. A replica filter was then applied onto the same plate, but this was allowed to stick for 10 min. before peeling off. Similarly, the orientation of the replica filter on the master plate was recorded, but the marks were fixed on different locations from the first filter. The replica filter serves to confirm positive clones as only truly hybridizing clones will show autoradiographic signals unambiguously at the same spot on two different filters.

2. Processing of Blotted Filters

After air drying, the phage DNA was denatured by incubating the filters in a solution of 0.2M NaOH/1.5M NaCl for 2 min. Subsequently, the phage DNA was neutralized with 0.4M Tris-HCl, pH 7.6/2×SSC for another 2 min., and then saturated with 2×SSC for 2 min. The denatured phage DNA was then irreversibly immobilized onto the nylon membranes by UV irradiation at 312 nm for 2 min., followed by baking at 80° C. for 1 h.

3. Screening by Hybridization

After baking, membranes were prewashed in a solution of 50 mM Tris-HCl, pH 8.0, containing 1M NaCl 1 mM EDTA, and 0.1% SDS for 30 min. at room temperature to remove any bacterial debris still adhering to the filters. Filters were then prehybridized and hybridized as follows:

Prehybridization was carried out for 6 h at 42° C. in 50% formamide (v/v, Merck), 5×SSC (0.3M NaCl, 0.3M NaCl 0.3M Trisodium citrate), 5× Denhardt's solution (Maniatis et al. (1982) *Molecular Cloning, A Laboratory Manual*, Cold Spring Harbor Laboratory, p. 327), 50 mM phosphate buffer, pH 6.5, and 0.1% SDS. Boiled calf thymus DNA (100 µg/ml, Sigma) was used as carrier DNA. Hybridization was carried out overnight at 42° C. in 25 ml hybridization buffer (50% formamide, 5×SSC, 1× Denhardt's solution, 20 mM phosphate buffer, pH 6.5, 50 µg/ml calf thymus DNA, 0.1% SDS) using $^{32}$P-labelled Factor C cDNA of *T. tridentatus* (pFC53) as the probe. Salt and temperature conditions equivalent to the hybridization conditions employed can be calculated from the following equation (Sambrook et al. (1989) *Molecular Cloning, A Laboratory Manual*, Second edition, Cold Spring Harbor Laboratory Press, pp.9.50–9.51):

$$T_m=81.5° C.-16.6(\log_{10}[Na^+])+0.41(\%G+C)-0.63(\%formamide)-(600/1),$$

where l=the length of the hybrid in base pairs.

The membrane was washed 3× at low stringency with 1×SSC, 0.1% SDS washing solution at room temperature, followed by washing at high stringency with 0.1×SSC, 0.1% SDS at 42° C. for 30 min. and 2× with 0.1×SSC/0.1% SDS for 15 min. each at 42° C., or until low background radioactivity was attained. Membranes were autoradiographed for 5 days with a Hyperfilm MP at −70° C. in the presence of an intensifying screen (Kodak X-Omatic or Dupont Lightning Plus). The film was developed using a Kodak X-Omat MP4 developer.

The Factor C cDNA probe equivalent to 200 ng was radioactively labelled using the Multiprime Labelling system.

B. Secondary and Tertiary Screening

Positive clones which were detected on the autoradiograms of both the main filter and its replica were traced back to their exact locations on the master plate. As the plaques were quite close to each other, a plug of agarose approximately 1 mm in diameter containing a number of plaques located within the most proximate area which gave the postive signal was picked from the plate using a sterile 100 µl Eppendorf tip, the end of which was snipped off. Plugs were resuspended in 1 ml of suspension medium (SM: 50 mM Tris-HCl, pH 7.5 containing 100 mM NaCl 8 mM MgSO$_4$ and 0.01% gelatin, (w/v)), containing a drop of chloroform for at least 1 h at room temperature to enable the phages to elute into the buffer solution.

An aliquot of the SM buffer containing eluted phages was then mixed with 200 µl of plating bacteria and plated a second time on LB plates (90 mm diameter) as described above, but such that only about 50 to 100 widely spaced plaques were formed. These were similarly plaque lifted onto nylon membranes, denatured, hybridized, washed, and exposed as described under "Primary Screening." A well-isolated plaque in the secondary screening was similarly resuspended in SM buffer, and a tertiary screening was performed. Tertiary screening confirms the purity of the secondary plaque by demonstrating whether all the plaques generated gave strong positive signals after autoradiography. A single plaque from the tertiary screening was then used to propagate and purify the presumptive clones for subsequent characterization.

As a rare copy gene, *C. rotundicauda* Factor C cDNA represented only 0.03% of the amoebocyte cDNA library. A total of 40 presumptive clones were isolated, of which 16 were further studied. The *C. rotundicauda* Factor C recombinants (λCrFC) were purified, and the sizes of their inserts were determined after digestion with Eco RI and Not I. There is one Eco RI site within these inserts. The CrFC cDNA partial fragments flanked by Eco RI-Eco RI (EE) and Eco RI-Not I (EN) were further subcloned into pGEM 11 Zf(+) and transformed into *E. coli* JM 109 and DH5α. These subclones, referred to as pEE and pEN, respectively, were characterized by restriction mapping and DNA sequencing.

EXAMPLE 2

Comparison of the Restriction Maps of CrFC and TtFC cDNAs

Figure 3:
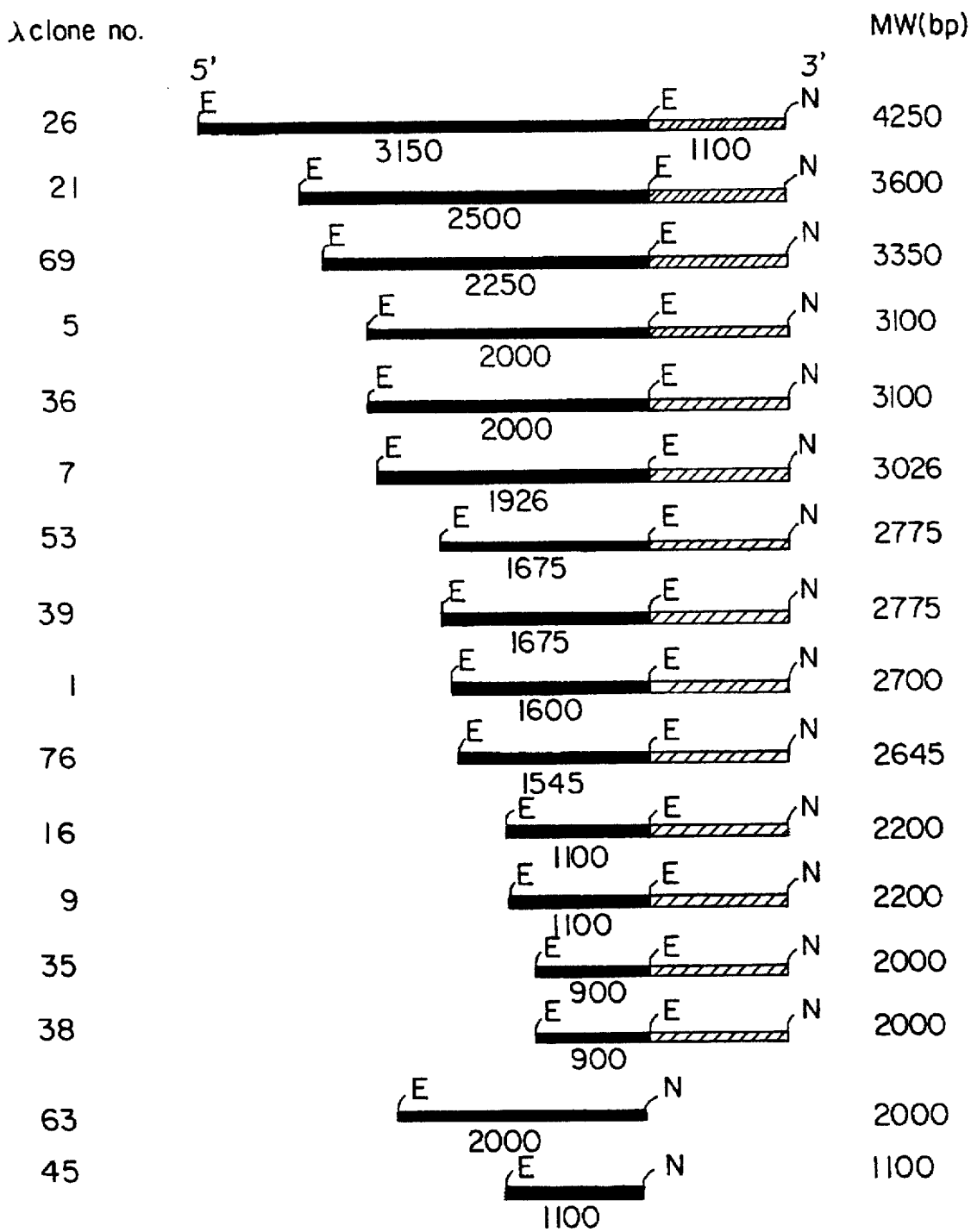
FIG. 3 shows the initial restriction maps of the various Factor C cDNAs isolated and purified from the *C. rotundicauda* amoebocyte cDNA library based on Southern analysis with pFC53 (*T. tridentatus* Factor C cDNA) and the 1100 bp Eco RI-Not I fragment. The cDNAs are arranged in decreasing order of size, and are labelled with the restriction sites Eco RI (E) and Not I (N). Fragments homologous to pFC53 are drawn with solid boxes, while those homologous to the E-N fragment are drawn with engraved boxes.
Figure 4A:
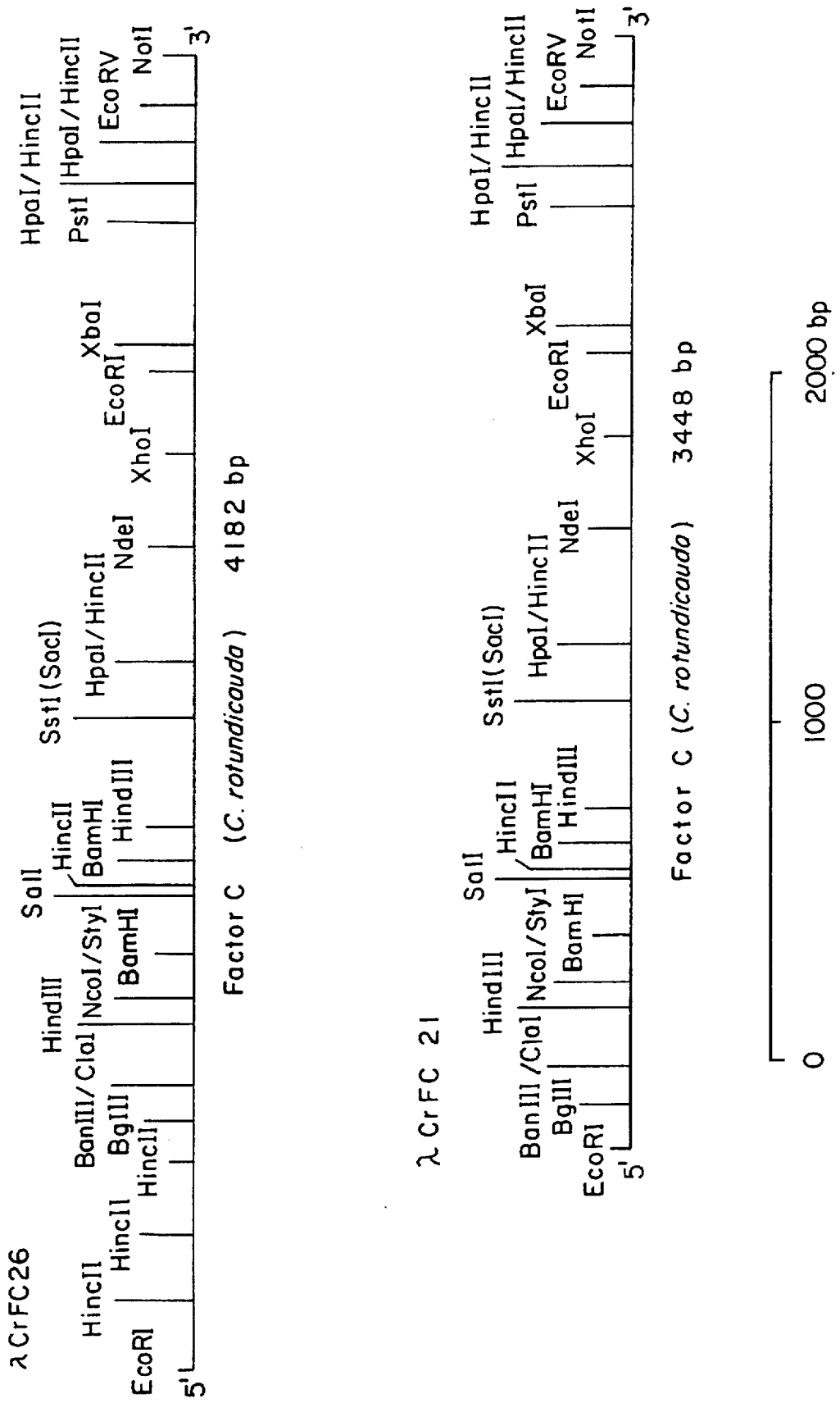
FIG. 4 shows a comparison between the complete restriction maps of λCrFC 26, λCrFC 21 (*C. rotundicauda*), λFC 53, and λFC 41 (T. tridentatus, see Muta et al., 1991. *J. Biol. Chem.* 266, 6554–6561).
Figure 4B:
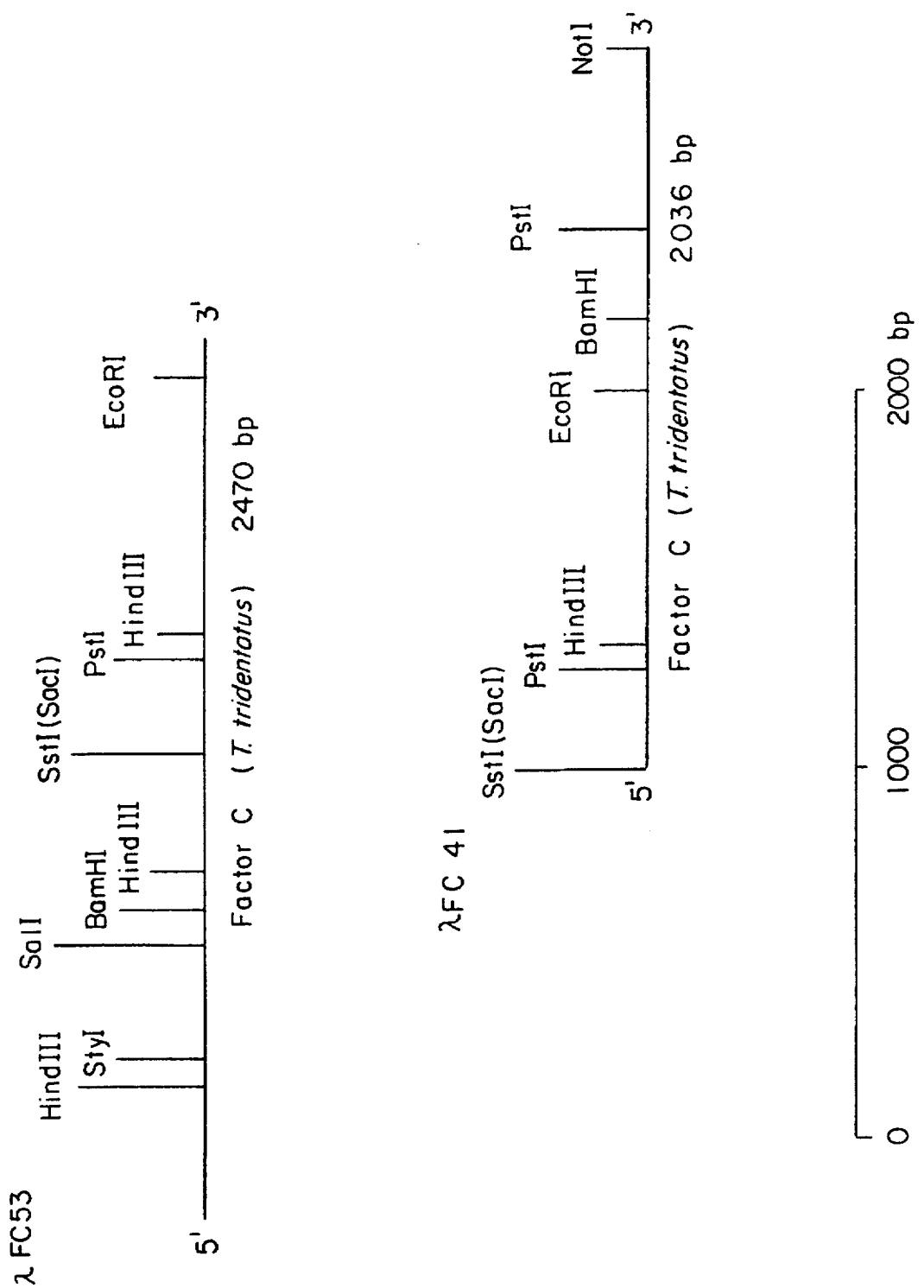

The orientations of the 16 λCrFC clones were determined, and subsequently, their initial restriction maps were analyzed for Eco RI and Not I sites (FIG. 3). The complete restriction maps of the two longest clones of *C. rotundicauda* Factor C cDNAs, λCrFC 21 and λCrFC 26, are shown in FIG. 4, in comparison with the maps of the two overlapping clones of *T. tridentatus* Factor C, TtFC (λFC 53 and λFC 41) (Muta et al., 1991. *J. Biol. Chem.* 266, 6554–6561). λCrFC 26 and λCrFC 21 will henceforth be referred to as CrFC 26 and CrFC 21, respectively. CrFC 26 has a longer 5' terminal end compared to the *T. tridentatus* FC 53. Based on the restriction sites of the λFC 53 and λFC 41 clones, the cDNAs from both species have the same locations for restriction sites such as Sty I, Sal I, Sac I, Hind III and Bam HI. However, notable differences were also observed between the cDNAs: CrFC 26 has two Bam HI sites compared to only one in λFC 53. On the other hand, the former has only two Hind III sites compared to three in the latter. The loss of one Hind III site in CrFC 21 and 26 was due to a base substitution (C to T) at the 1700 and 2443 bp positions, respectively.

λFC 41, on the other hand, encompasses the 3' region of the TtFC. It begins from the Sac I/Sst I site up to the 3' end, and was found to contain the internal Eco RI site relative to that of CrFC 26. The other common site between λFC 41 and CrFC 21 and 26 is the Pst I site proximal to the 3' end, but the second Pst I site near the 5' end of λFC 41 was absent in CrFC 21 and CrFC 26. The Bam HI and Hind III sites in λTtFC 41 were absent in CrFC 21 and CrFC 26.

EXAMPLE 3

The DNA Sequences and Derived Amino Acid Sequences of CrFC 26 and CrFC 21

Figure 5A:
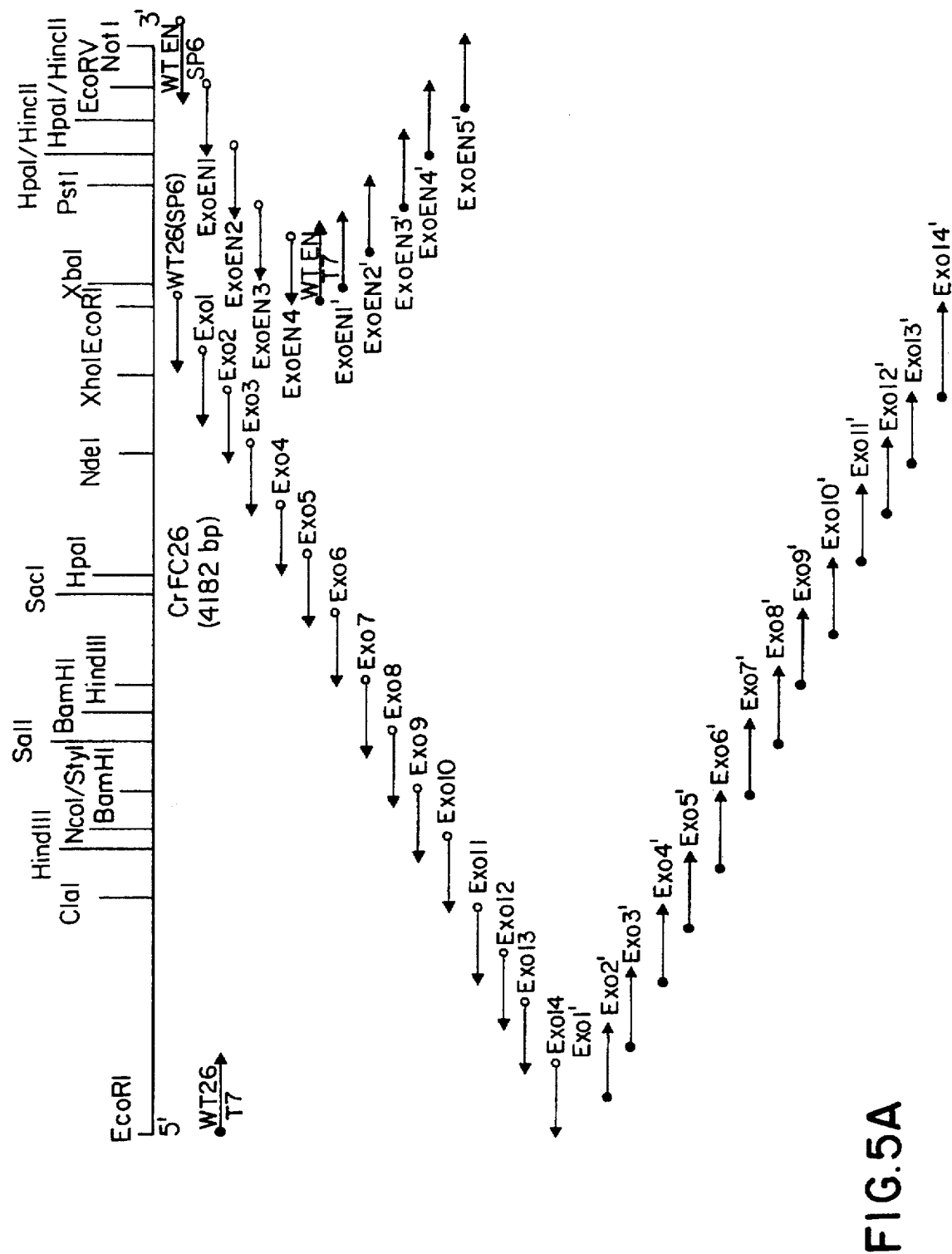
FIG. 5a and FIG. 5b show the sequencing strategies for clones CrFC 26 and CrFC 21, respectively. Deletion subclones were prepared from pEE and pEN in both directions. The arrows indicate the direction and the extent of the sequences obtained. T₇ promoter primer (→) and SP6 promoter primer (→) were used.
Figure 5B:
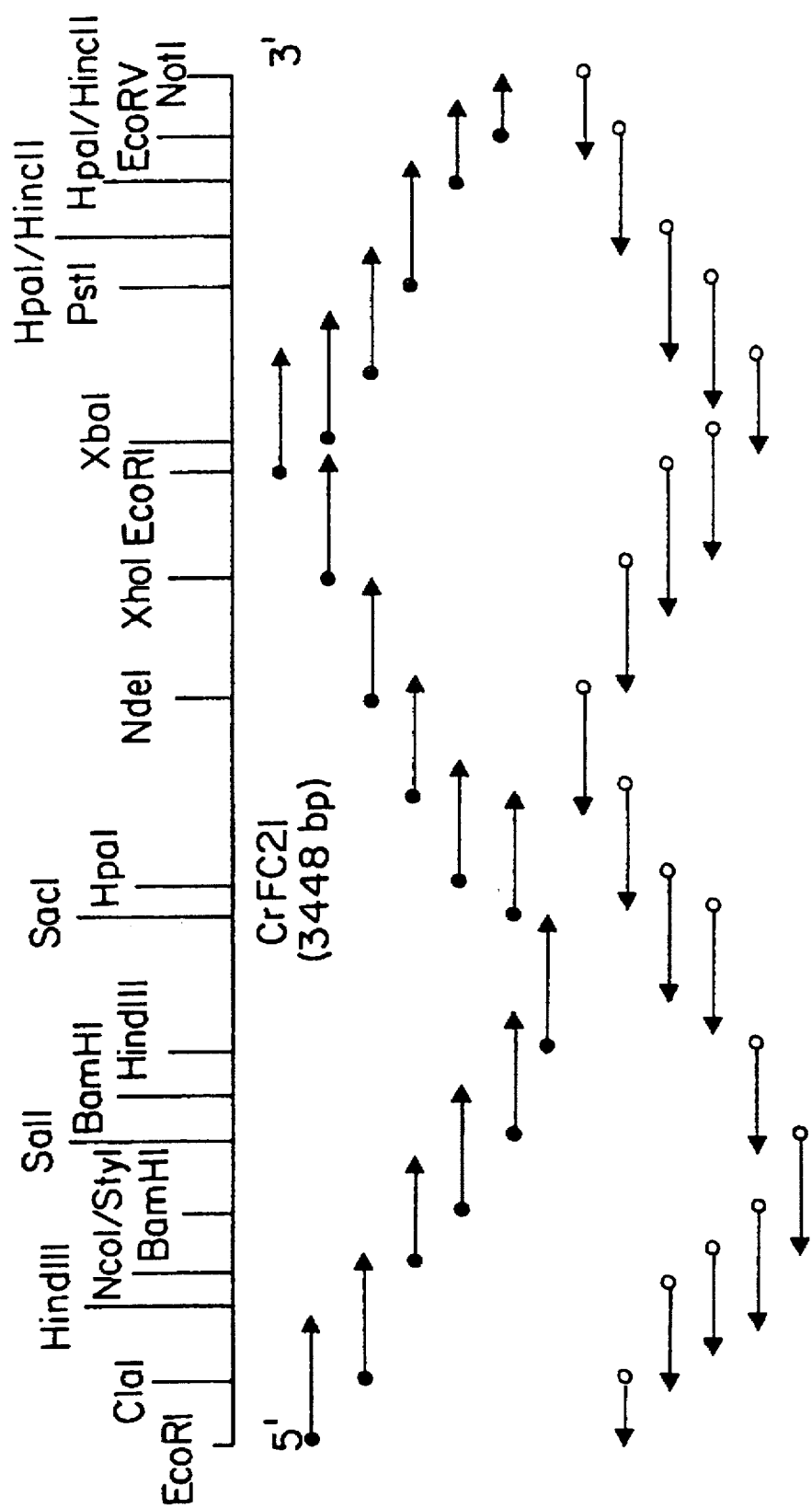
Figure 7A:
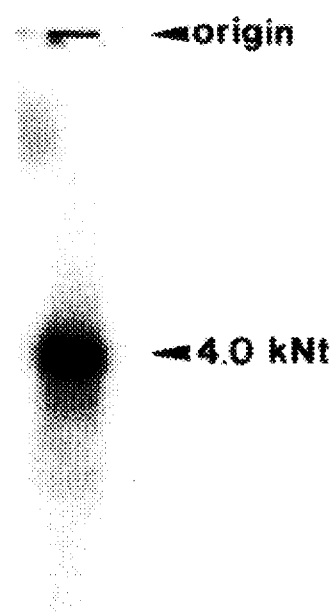
FIG. 7 shows Northern blot analysis of 10 μg total amoebocyte RNA using (a) Eco RI-Eco RI fragment and (b) 369 bp Eco RI-Nde I (5' end) of pCrFC 26 as probes. A single band of approximately 4 kNt was deduced in both blots, indicating that the cDNA isolated is full-length, and that the entire 5' end unequivocally belongs to this species of Factor C.

The DNA sequences of CrFC 26 and CrFC 21 were determined on both strands by the Sanger dideoxy sequencing method. FIGS. 5a and 5b show the sequencing strategies for CrFC 26 and 21, respectively. To counter check the sequences obtained, the 5' ends of other CrFC subclones (pCrFC 69, 1, 16 and 35) were also sequenced using the T$_7$ promoter as primer binding site. The complete cDNA of CrFC 26 was found to be 4182 bp (FIG. 6). This is consistent with the Northern analysis (Reed and Mann, 1985. *Nucl. Acid Res.* 13, 7207–7221) of the amoebocyte total RNA with homologous EE insert, which showed only one hybridizing band at approximately 4 kNt (FIG. 7a). CrFC 26 cDNA includes 568 nucleotides of 5' untranslated sequence containing seven ATGs before the real initiation site, an ORF of 3249 nucleotides coding for a protein of 1083 amino acids, a stop codon, and 365 nucleotides of 3' untranslated sequences. At the 3' end of the cDNA, the canonical hexanucleotide sequence, AATAAA, is present 19 nucleotides upstream from the polyadenylation site (at nucleotide position 4142). There are three other AATAAA sequences, found at nucleotide positions 183, 239 and 2474, respectively. The ORF codes for a signal peptide of 24 amino acids and a Factor C zymogen of 1059 residues, which, prior to N-glycosylation, has a calculated molecular weight of 120, 244 daltons. This is close to the estimated molecular weight of single- and double-chain Factor C enzymes purified from amoebocytes (Ding et al., 1993. Biochim. et Biophys. Acta. 1202, 149–156). The unique proteolytic site due to endotoxin-activation of the Factor C enzyme is found between phe-ileu, thus indicating the integrity of the cloned Factor C cDNA, and its potential application in endotoxin detection.

The CrFC 21 cDNA sequence and its derived amino acid sequence are shown in FIG. 8.

EXAMPLE 4

Variant Forms of the CrFC Gene

Figure 7B:
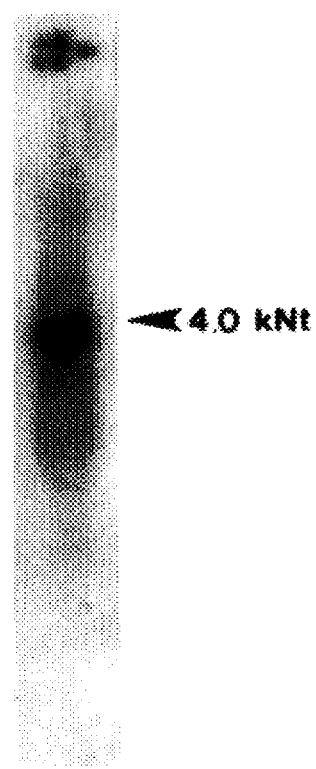

The Factor C cDNA sequence indicates the existence of at least two types of Factor C mRNA in C. rotundicauda. The N-terminal sequences of CrFC 26 and CrFC 21 differed significantly. Comparison of the sequences between C. rotundicauda Factor C clones CrFC 21 and CrFC 26 with that of T. tridentatus (TtFC 53) shows that CrFC 21 and TtFC 53 share precisely similar homology at the 5' end. Yet, the most notable difference in the DNA sequences of Factor C from the two species of horseshoe crabs is the existence of an extra 716 nucleotides at the 5' end of the CrFC 26 (FIG. 9). Thus, CrFC 21 was not merely a truncated species of CrFC 26. Instead, it was derived from a totally distinct species of mRNA that may be exactly identical to the one that gave rise to the T. tridentatus Factor C cDNA. To unequivocally demonstrate the authenticity of the 5' noncoding region of CrFC 26, a further Northern blot analysis was performed, but using only the first 369 bp of the 5' untranslated region of CrFC 26 (fragment flanked by Eco RI and Nde I) as probe. The result in FIG. 7b clearly demonstrates that the entire 5' end of CrFC 26 truly belongs to this particular species of Factor C mRNA. Thus, the existence of the two types of C. rotundicauda Factor C cDNA could be attributable to differential splicing of the initial primary transcript around its 5' terminal.

EXAMPLE 5

Computational Analysis of the 5' Noncoding Region of λCrFC 21 and 26

The unusually long 5' untranslated sequences occur on unusually interesting mRNAs such as epidermal growth factor, EGF (Scott et al., 1983. Science 221, 236–240), oncogenes (Watt et al., 1983. Nature 303, 725–728) and heat shock proteins (Ingolia et al., 1981. Nucl. Acids Res. 9, 1627–1642). This invites speculation that long structures of the 5' noncoding region participate in the regulated expression of these genes, including that of Factor C. However, long 5' noncoding sequences in some mRNAs may have a deleterious effect (Kozak, 1983. Microbiol. Rev. 47, 1–45), especially if they contain secondary structures which may deflect ribosomes from the authentic initiation site that lies further downstream. This was true for the Semliki Forest virus (Lehtovaara et al., 1982. J. Mol. Biol. 156, 731–748) and the recombinant fish antifreeze protein III gene (Li et al., 1991. Protein Eng. 4, 995–1002). This could also apply to CrFC 26 since there are seven false ATG sites (underlined in FIG. 6) lying upstream from the authentic ATG start site found at nucleotide position 569. All these false start sites were followed shortly by in-frame stop sites downstream. This configuration agrees with the ribosome scanning-reinitiation model of translation in eukaryotic genes (Kozak, 1986. Cell 47, 481–483). This is probably one reason why there exists another form of Factor C mRNA having a much shorter 5' noncoding sequence as in CrFC 21, where it may be translated more efficiently.

Figure 10A:
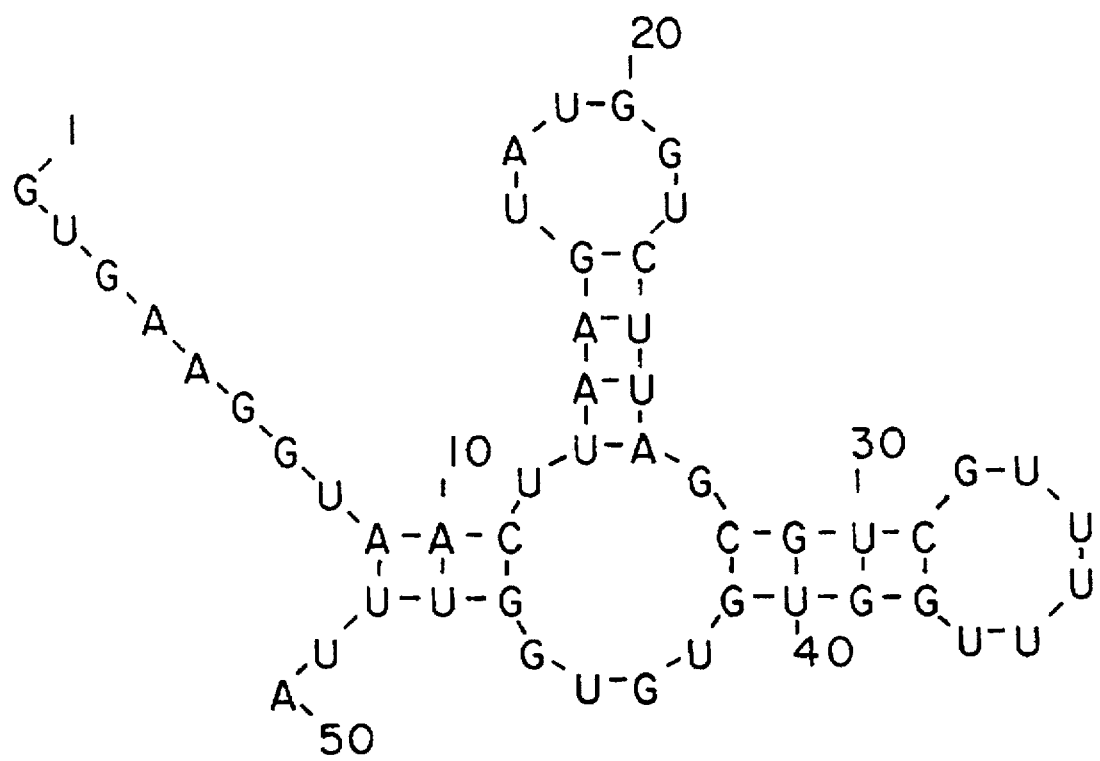
FIG. 10a–10c show the computational predictions of the secondary structures of mRNAs of (a) CrFC 21 and (b) CrFC 26. The leader sequence of CrFC 26 shows numerous hairpin stems and loops. The authentic AUG start codon is boxed. The start codon in CrFC 21 is exposed in a loop, and appears more accessible.
Figure 10B:
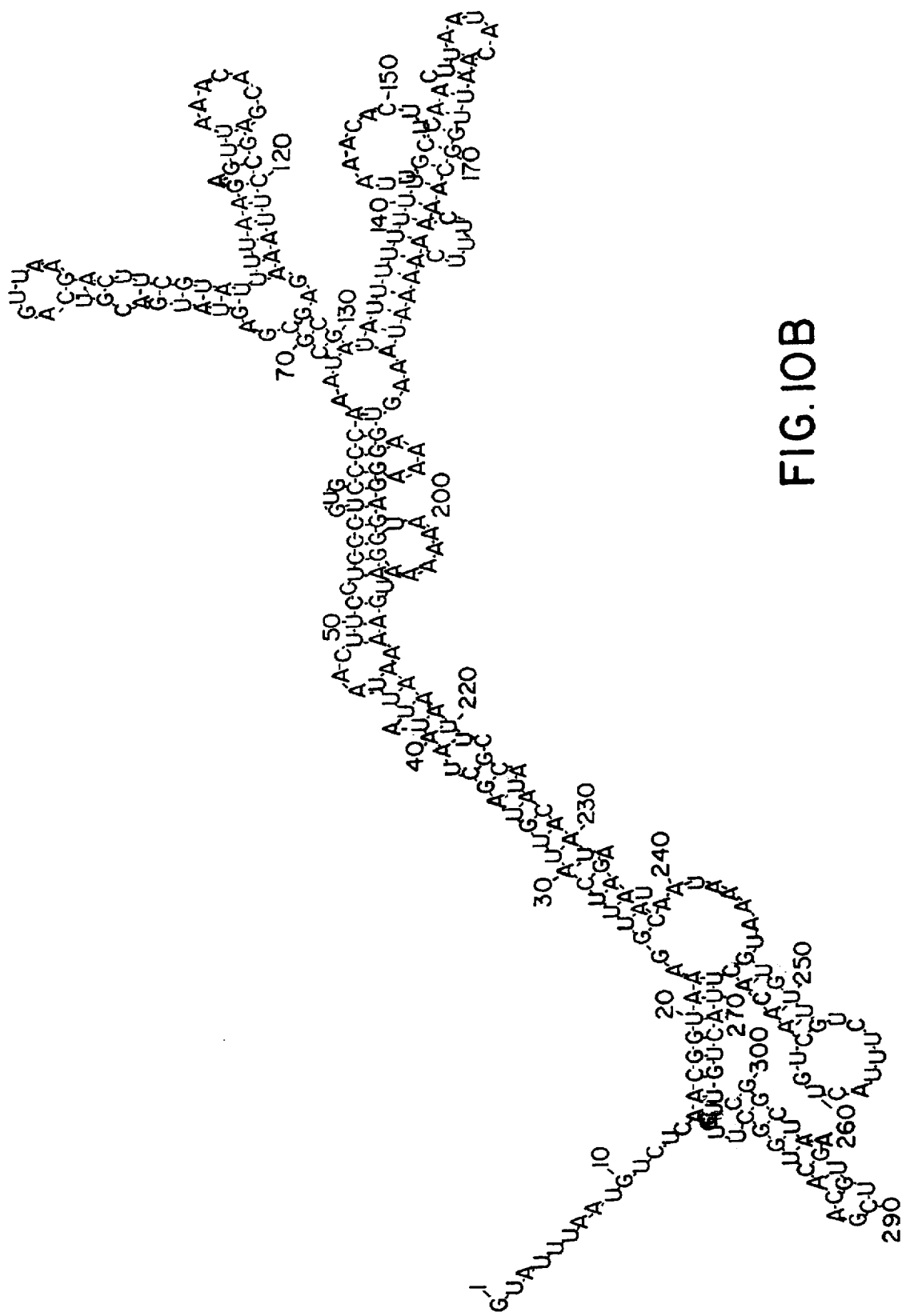
Figure 10C:
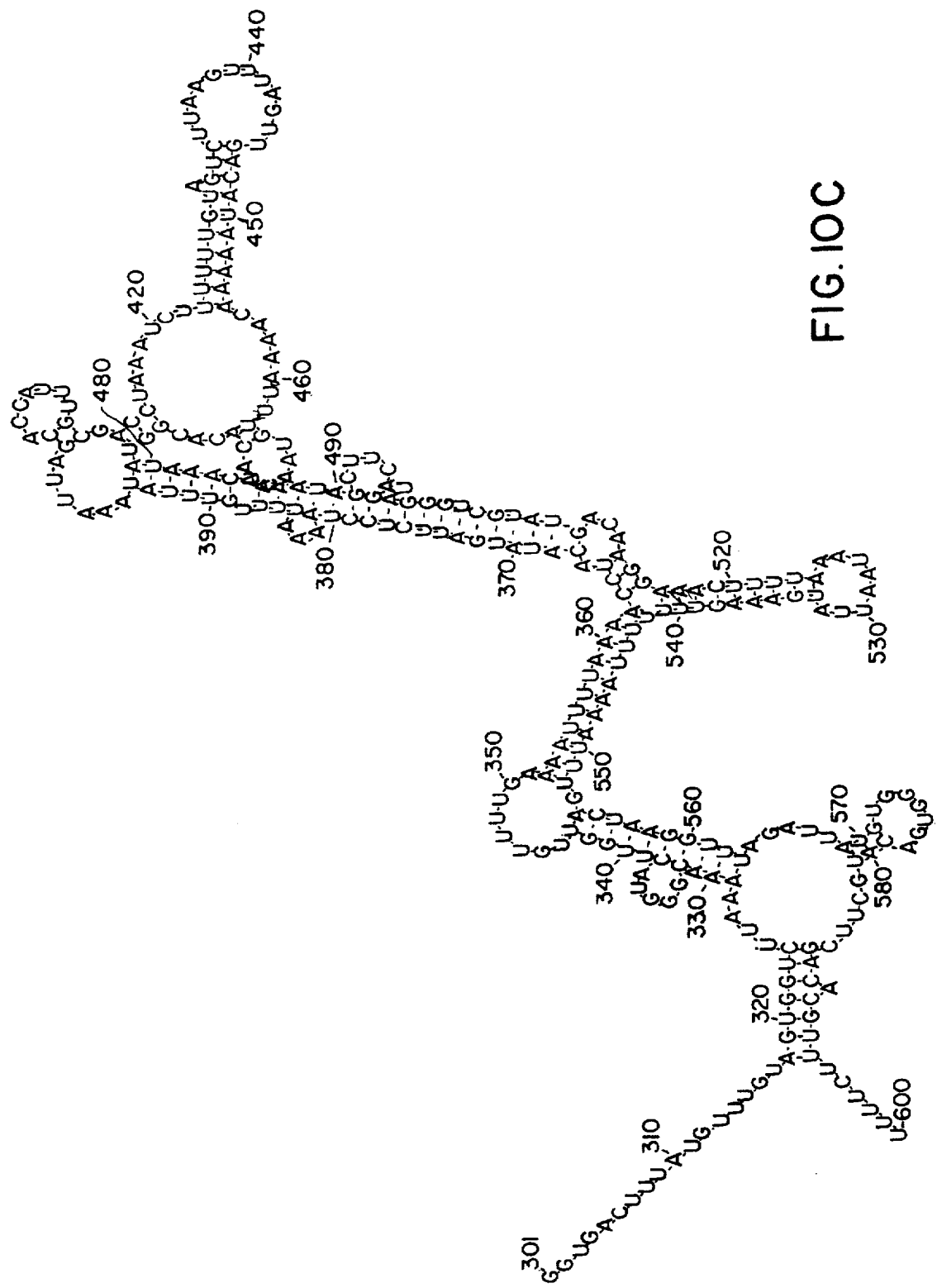

FIGS. 10a and 10b show the secondary structure predicted for the 5' ends of the mRNA of CrFC 21 and CrFC 26, respectively. CrFC 21 exhibits a well-exposed AUG codon in a loop. In contrast, CrFC 26, with its 7 false start codons, shows numerous hairpin stems and loops, and its real start codon appears less accessible to ribosome binding.

From computational analysis of the secondary structures of CrFC 21 and 26, it is clear that both clones could be further manipulated at their 5' ends to give appropriate Factor C cDNAs for subcloning into Pichia pastoris vector for overexpression of the recombinant Factor C enzyme. The recombinant Factor C could be used in a colorimetric assay for endotoxin.

EXAMPLE 6

Homology Between the DNA Sequences of CrFC and TtFC

In comparing the cDNAs of CrFC 26 and 21 with that of TtFC (FIG. 11), the C. rotundicauda gene was found to be longer by 716 nucleotides at the 5' end, and also has an extra 64 amino acids upstream from the starting met. The start of homology of both the DNA and amino acid sequences between the two species was found at nucleotide positions 785 for CrFC 26 and 42 for CrFC 21, as compared to position 69 for TtFC. The homologous region extends through to the poly A tail of both genes, giving 97.7% homology between CrFC 26 and TtFC. Most of the dissimilarities, however, were found in the 3' untranslated region, where a lower percentage homology of 86% was observed.

A majority of the differences between the CrFC and TtFC sequence found within the ORF were due to base substitutions. In fact, these substitutions explain the perceived differences in the restriction sites earlier obtained by restriction mapping (see FIG. 4), for instance, the absence of the Bam HI (GGATCC) site in TtFC, which in CrFC 21 and 26 is located 807 and 1550 bp, respectively, from their 5' ends. This was due to the substitution of the first G by T in TtFC. The converse is shown with the Bam HI site at bp 2431 of TtFC, in which the second C is substituted by a T in the CrFC cDNAs. Similarly, the Pst I site (CTGCAG) of TtFC (at 1688 bp from its 5' end) was not found in CrFC because the first C was substituted by a T. Again, base substitution of C by T was responsible for the loss of the third Hind III site (AAGCTT) in CrFC, which in TtFC was located 1725 bp from the 5' end. Base substitution also occurred at 2361 and 3104 bp of CrFC 21 and 26, respectively, giving the Xba I (TCTAGA) site, where the first A is substituted by a C in TtFC. Similar to TtFC, there are six potential N-glycosylation sites within the CrFC sequence Asn-Xaa-Ser/Thr.

EXAMPLE 7

Structural Domains and Homology Comparison of CrFC With Other Serine Proteases

The secondary folding structures of several blood clotting factors in the human coagulation system are usually identified by common domains derived from homologous regions in the DNA sequence (Furie, B. and Furie, B.C. 1988. *Cell* 53:505–518). Typically, all these factors have a signal peptide at their N-terminal, and a catalytic domain at the C-terminal, which for serine proteases like *C. rotundicauda* Factor C, also contain the catalytic triad, $His^{809}$-$Asp^{865}$-$Ser^{966}$ for CrFC 21 and $His^{873}$-$Asp^{929}$-$Ser^{1030}$ for CrFC 26 (see FIG. 11). A hydropathy profile based on the formula of Kyte and Doolittle (1982. *J. Mol Biol.* 157, 105–132) of the first 59 amino acids of CrFC 26 showed the first 24 residues to be the putative signal peptide rich in hydrophobic amino acids (FIG. 12). CrFC 26 has five short consensus repeats (residues 206–259, 263–318, 324–385, 640–698 and 758–812), one lectin-type domain (500–632), one EGF-like domain (167–200), a cys-rich region (90–165), and one pro-rich region (732–754). The serine protease domain is found at positions 827–1083). No propeptide sequence, kringle domains (Park, C. H. and Tulinsky, A. 1986. *Biochemistry* 25, 3977–3982), amino acid stacks, or finger domains were found.

By scanning the EMBL gene data bank, a homology search for the serine protease catalytic domain of CrFC revealed that it is structurally closest to *T. tridentatus* Factor C, with 97.7% homology in 777 overlapping nucleotides (Table I).

TABLE I

Percentage homology comparison of the catalytic domain of *C. rotundicauda* Factor C with other serine proteases based on entries in the EMBL data bank.

| Gene | % homology | bp overlap |
|---|---|---|
| *Tachypleus tridentatus* Factor C | 97.7 | 777 |
| *Onchorhynchus mykiss* thrombin | 54.4 | 709 |
| *Rattus norvegicus* thrombin | 52.2 | 624 |
| Rat prothrombin | 52.2 | 624 |
| *Acipenser transmontanus* thrombin | 52.8 | 623 |
| *Oryctolagus cuniculus* thrombin | 57.3 | 595 |
| Mouse prothrombin | 52.7 | 509 |
| Human blood coagulation Factor VII | 55.7 | 420 |
| Guinea pig Factor IX | 57.4 | 296 |
| Human liver hepsin | 59.0 | 278 |

From the overall comparison with serine proteases from other species, the CrFC is structurally closest to prothrombin and thrombin. This finding agrees well with the preference of Factor C for hydrolysis of synthetic substrates of thrombin. Surprisingly, a human liver hepsin (Leytus et al., 1986. *Biochemistry* 25, 5098–5102) exhibited a slightly higher level of homology with CrFC than other blood coagulation factors. Although the function of hepsin is still unknown, this serine protease, which lacks a typical signal peptide but instead has a transmembrane domain, was nevertheless shown to have characteristics typical of trypsin. Based on the primary structure of CrFC, it was also found to be catalytically similar to trypsin-type serine protease, although structurally closer to thrombin. This may be explained by the $Asp^{1024}$ (as opposed to Ser) in CrFC 26, analogous to $Asp^{189}$ in trypsin (Hartley, B. S. 1970. *Phil. Trans. R. Soc. London*, 257, 77–87), which strongly suggests that CrFC possesses a substrate specificity similar to that of trypsin.

EXAMPLE 8

Subcloning of CrFC cDNAs in Expression Vectors

Figure 13:
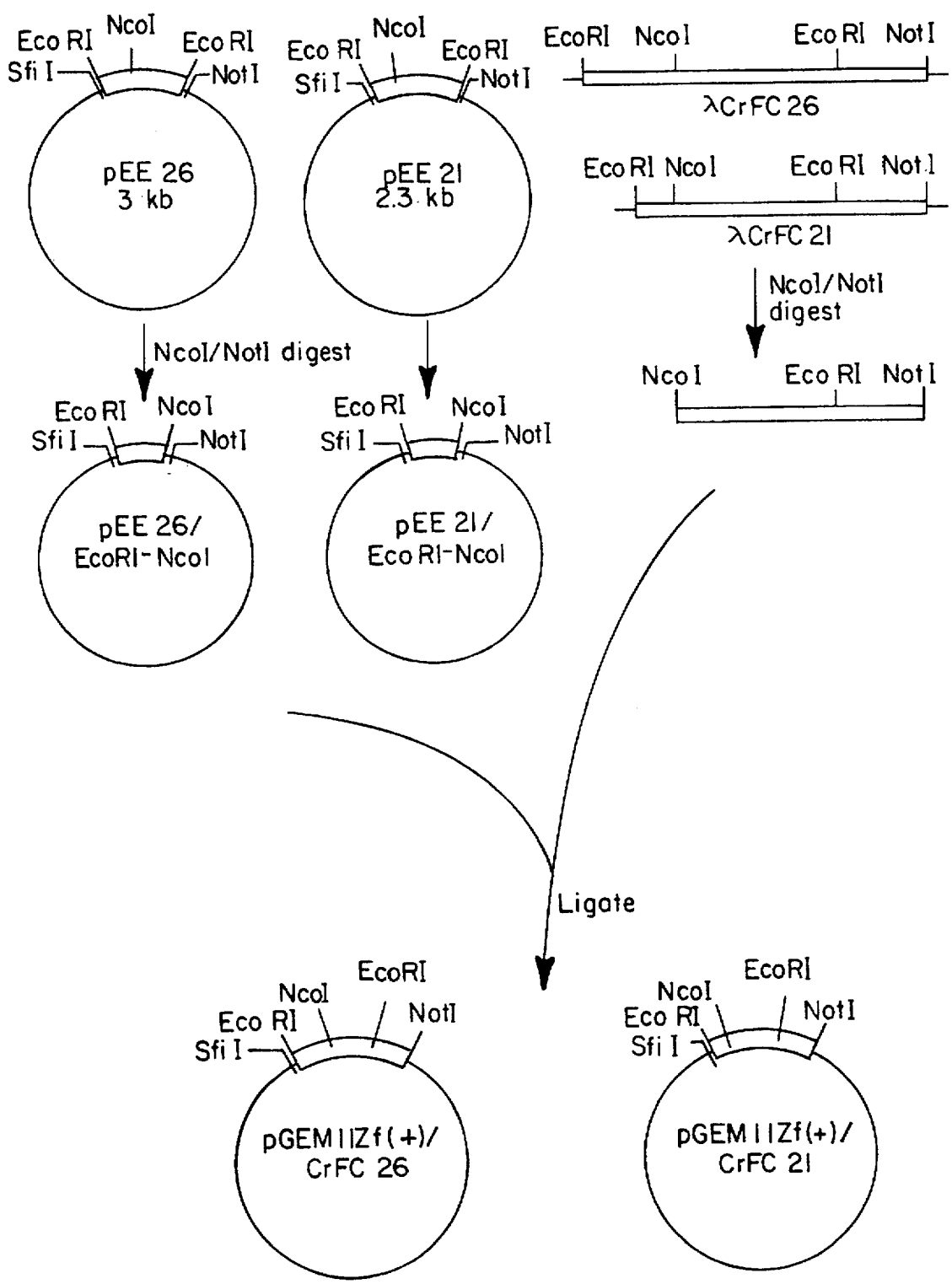
FIG. 13 shows manipulations of pEE 21 (Eco RI-Eco RI=2.3 kb) and pEE 26 (Eco RI-Eco RI=3 kb), and λCrFC 21 and λCrFC 26, to reclone full-length Factor C cDNAs into pGEM11Zf(+). The pEE of both subclones 21 and 26 being originally subcloned in pGEM11Zf(+) (see Example 8) were digested with Nco I and Not I enzymes. In parallel, the original λCrFC 21 and λCrFC 26 recombinants were also digested with Nco I and Not I to release the partial fragments of Factor C cDNA inserts flanked by Nco I-Not I. The pGEM 11Zf(+) containing the remaining Factor C cDNA inserts flanked by Eco RI-Nco I were then ligated to their corresponding Nco I-Not I inserts of Factor C derived from λCrFC clones. Thus, pGEM 11Zf(+)/CrFC 21 and pGEM 11Zf(+)/CrFC 26 were obtained, each containing the complete CrFC cDNAs of clones 21 and 26, respectively. These full length Factor C cDNA inserts could thus be excised intact by digestion with Sfi I and Not I enzymes.
Figure 14:
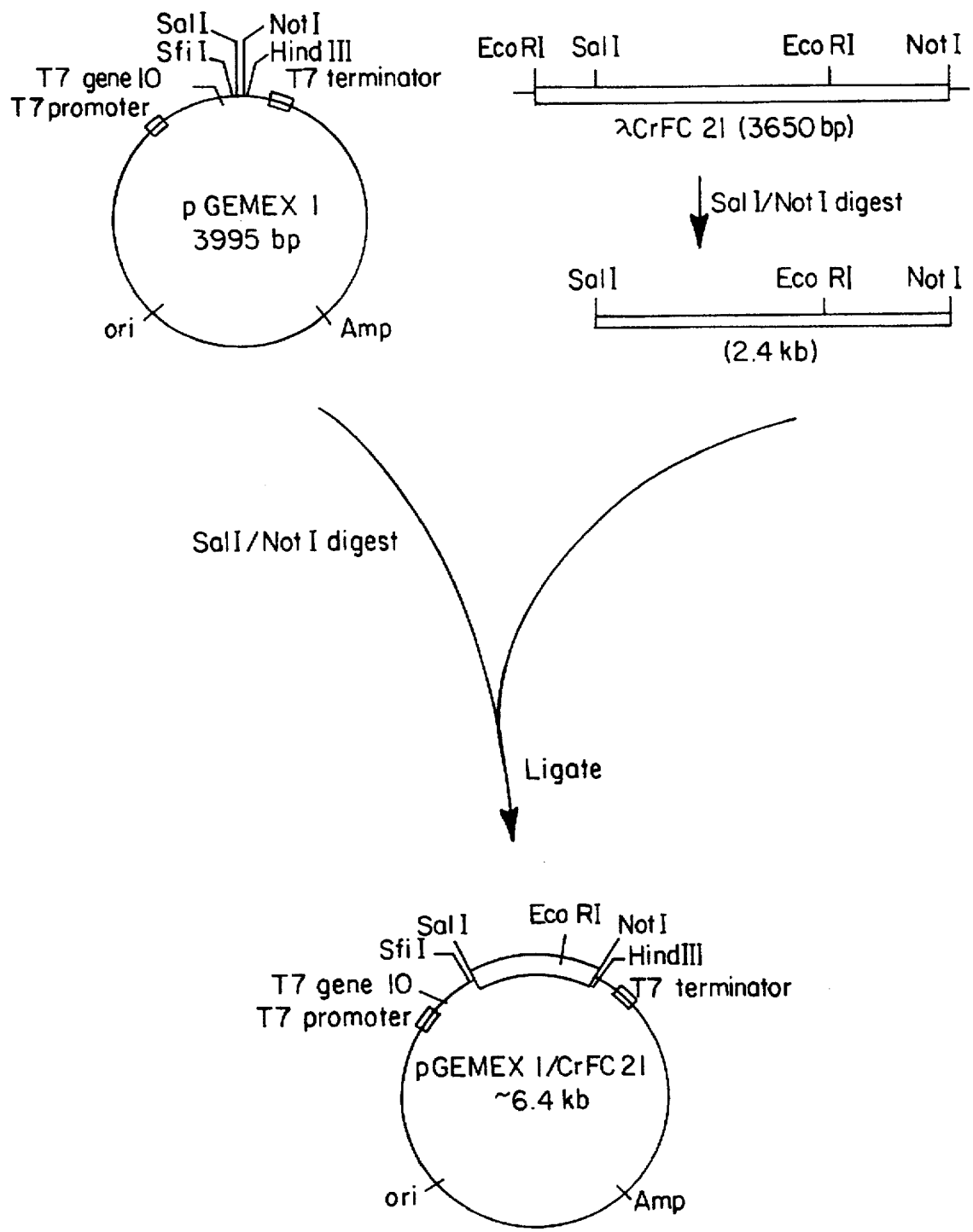
FIG. 14 shows the subcloning of CrFC 21 into pGEMEX-1. The vector pGEMEX-1 codes for a peptide of 260 amino acids which will be fused to the expressed Factor C protein. λCrFC 21 and pGEMEX-1 were digested with Sal I and Not I. The truncated portion of the Factor C cDNA insert of 2.4 kb (flanked by Sal I-Not I) was ligated in-frame into pGEMEX-1. The recombinant pGEMEX-1/CrFC 21 was then transformed into *E. coli* JM 109 (DE 3 lysogenic strain).
Figure 15:
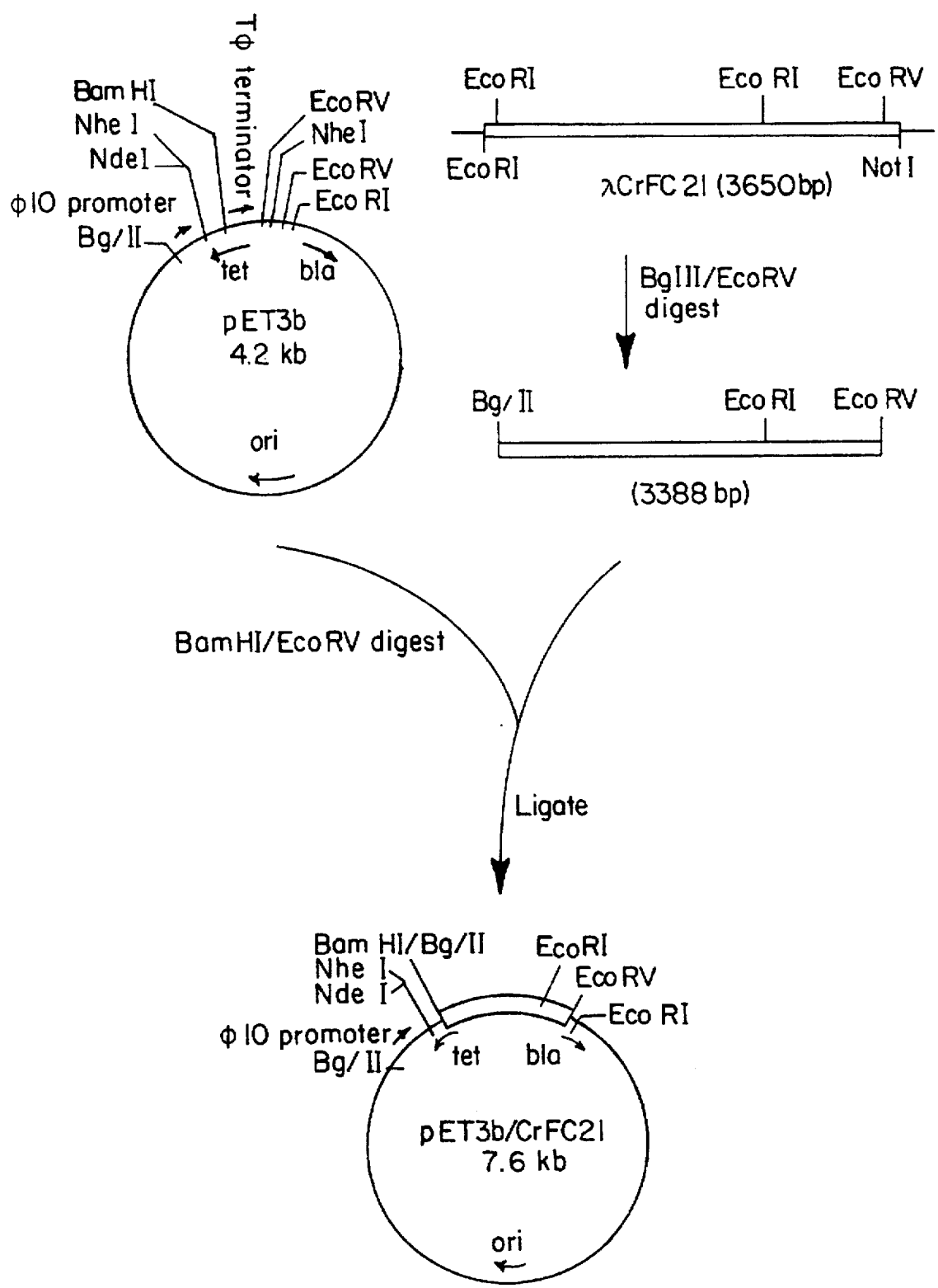
FIG. 15 shows the subcloning of CrFC 21 in pET 3b (pAR 3039). The vector, pET 3b, was constructed in such a way that the foreign gene is cloned in three different reading frames relative to the gene10 initiation codon in the Bam HI site (GGA, GAT, or ATC). For CrFC 21, the GAT codon would give the correct frame for expression. To linearize the vector, pET3b was digested with Bam HI and Eco RV. λCrFC 21 was digested with Bgl II and Eco RV. Bam HI and Bgl II have compatible ends. Ligation of the CrFC of 3388 bp (flanked by Bgl II-Eco RV) with the linearised pET 3b resulted in recombinants containing CrFC, the expression of which will be driven by the φ10 promoter to produce a fusion protein linked to the first 11 amino acids of the gene10 protein. The recombinant was transformed into *E. coli* JM109 (DE 3 lysogenic strain). The FC insert can be released by digestion with Bgl II (upstream) and Eco RV (downstream).
Figure 16A:
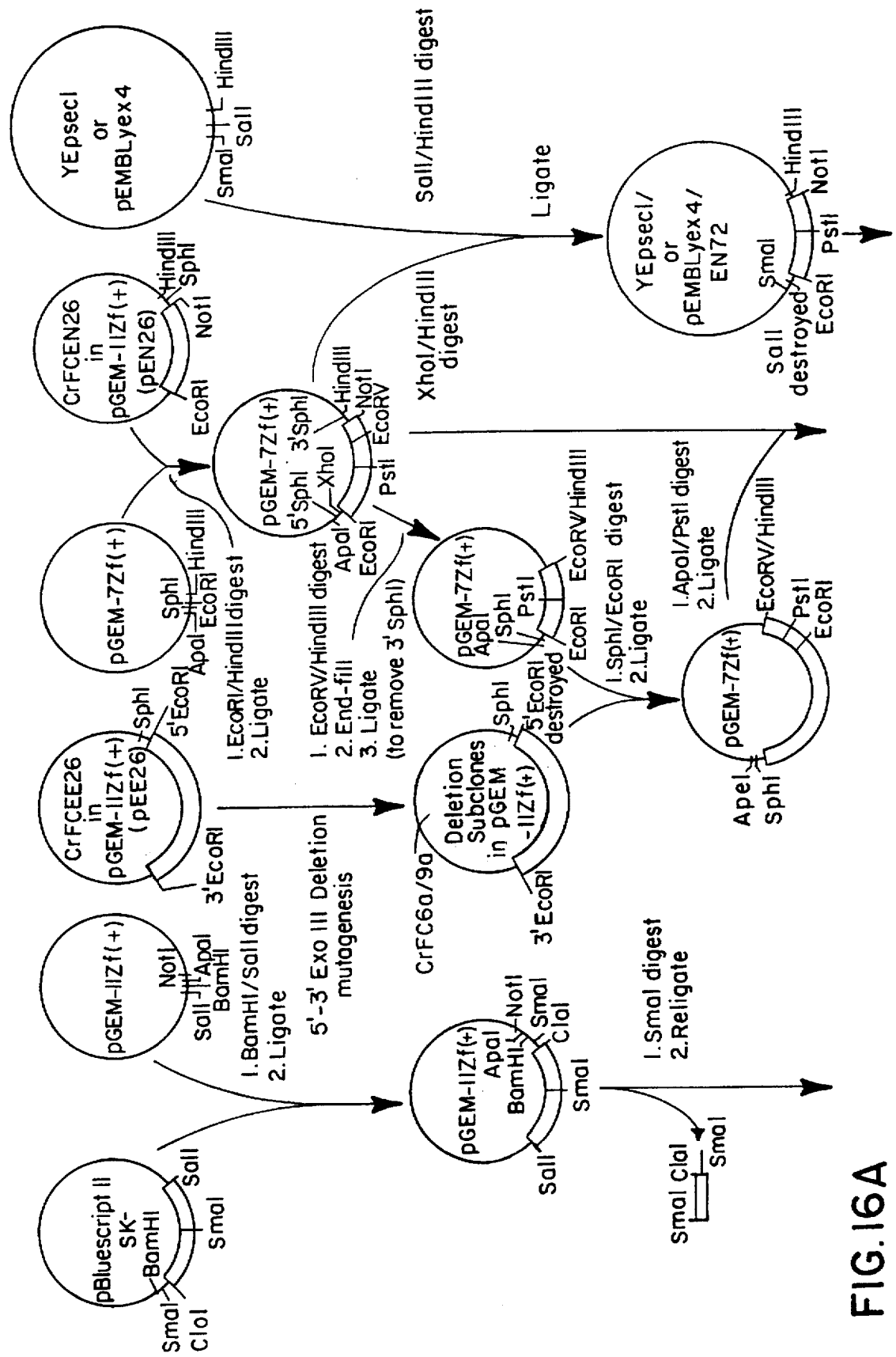
FIG. 16 shows the strategy for cloning CrFC 26 cDNA into *S. cerevisiae* vectors, YEpsec1 and pEMBLyex4. The EcoRI-EcoRI fragment (pEE26) and EcoRI-NotI fragment (pEN26) of CrFC 26 were first cloned individually into pGEM11Zf(+). The 5' untranslated sequences and varying lengths of the DNA encoding the leader peptide of CrFC 26 were deleted by performing 5'-3' Exo III deletion mutagenesis on the EcoRI-EcoRI fragment. The complete deletion mutants were reconstructed in pGEM7Zf(+) by ligating the 5' deleted EcoRI-EcoRI fragment of CrFC26 to the EcoRI-NotI fragment of CrFC 26. To facilitate subsequent manipulations, the complete deletion mutants (6a and 9a) were cloned into a modified pGEM11Zf(+). This plasmid was constructed by inserting a DNA fragment containing a Sma I site and a stuffer DNA segment (shaded blocks) from pBluescript II SK-into the multiple cloning site of pGEM11Zf(+). The deletion mutants were then excised with Sma I and Pst I and inserted into the secretory (YEpsec1) and non-secretory (pEMBLyex4) yeast expression vectors. Unless otherwise indicated, all DNA inserts are oriented in a 5' (left)-3' (right) direction.
Figure 16B:
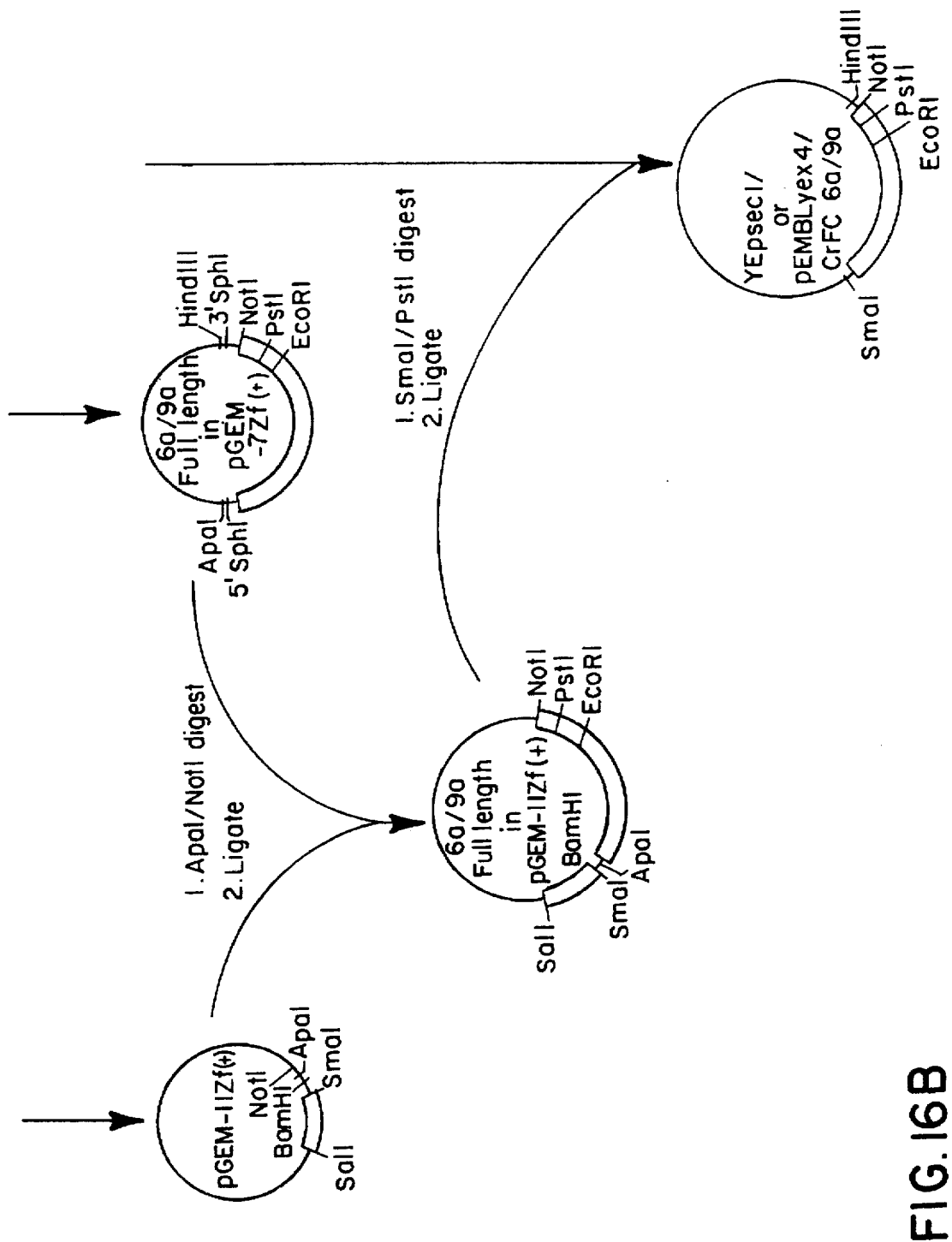
Figure 17A:
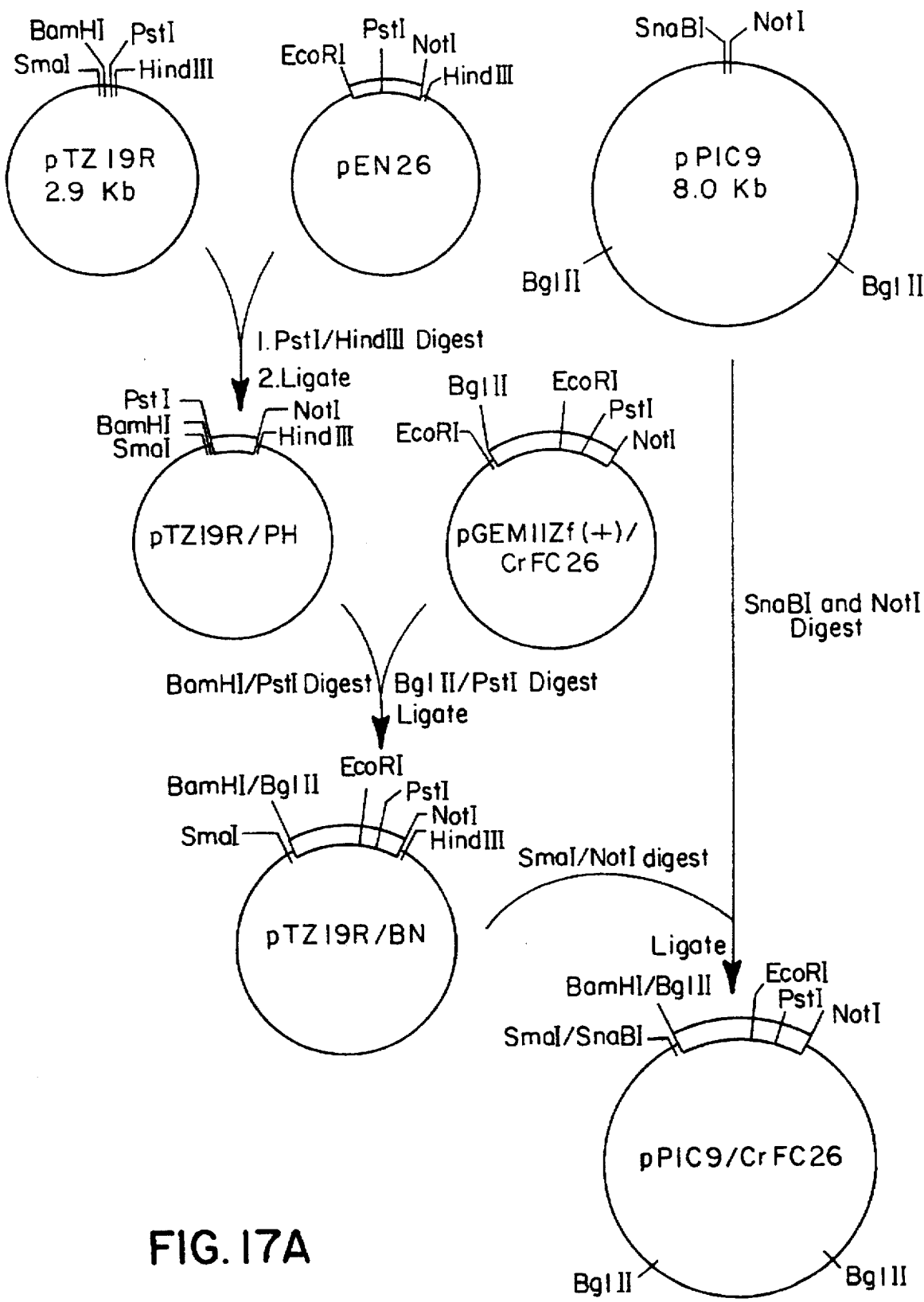
FIG. 17a shows the strategy for cloning CrFC 26 into the *P. pastoris* vector pPIC 9. The vector along with the gene of interest (cloned in frame for the secretory signal) was digested with Bgl II to release the AOX1 flanking insert for transformation into the yeast. Therefore, it was necessary to obliterate the Bgl II site in the CrFC gene and to create a 5' blunt end in frame for the Sna B1 site of the vector. The insert was first subcloned into pTZ19R in two steps. The PstI-HindIII fragment of CrFC insert (derived from pEN26) was first introduced into the vector, followed by the insertion of BglII-PstI fragment of CrFC 26 insert (derived from pGEM11Zf(+)/CrFC 26) into the BamHI-PstI cloning sites of pTZ19R/PH. This step removed the internal Bgl II site in CrFC 26. The insert was then excised using Sma I and Not I digestion from the pTZ19R/BN construct for cloning into compatible Sna B1 and Not I sites in pPIC 9. This construct is henceforth referred to as pPIC9/CrFC 26.
Figure 17B:
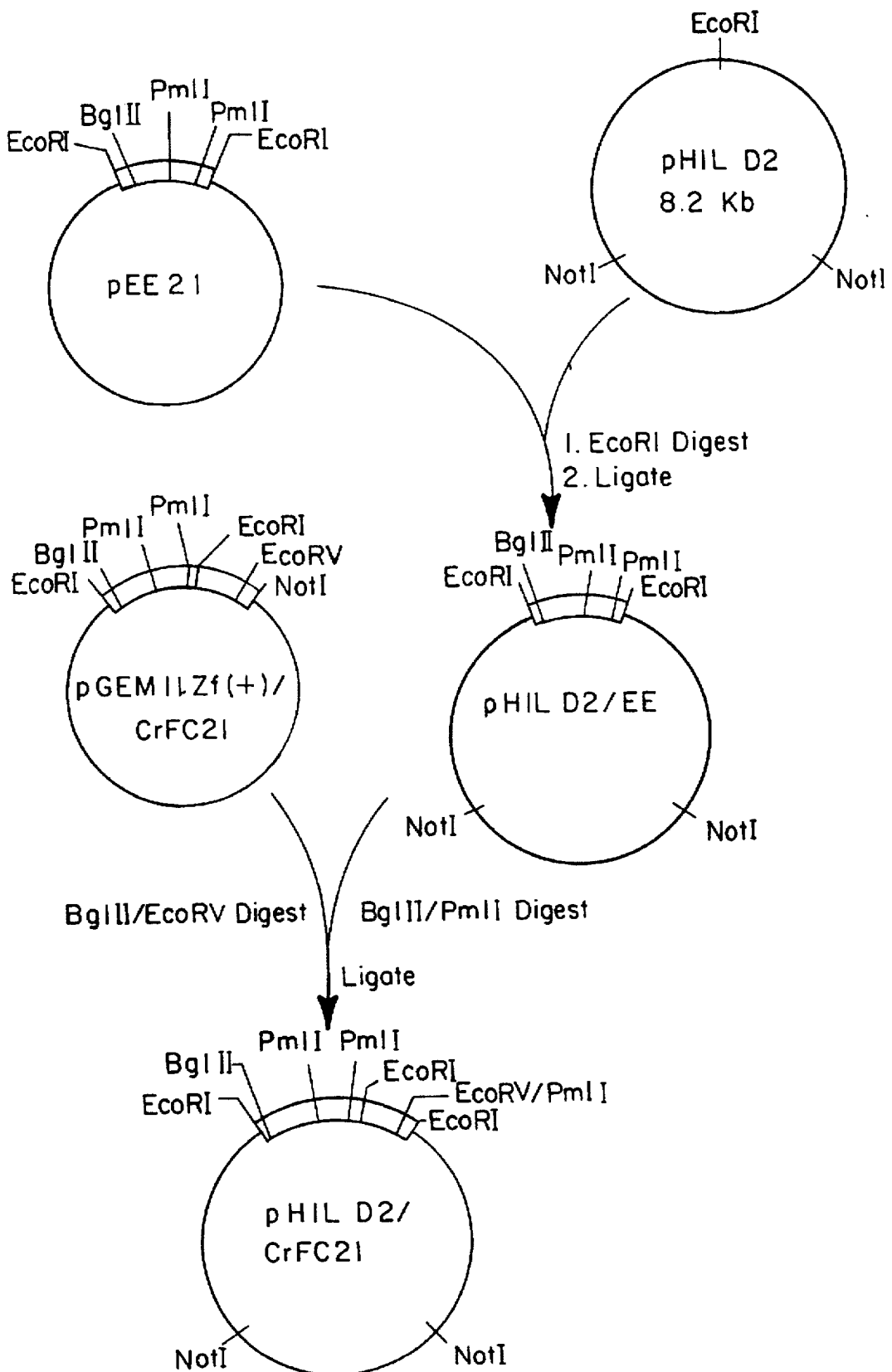
FIG. 17b shows the strategy for cloning CrFC 21 into the *P. pastoris* vector pHIL D2, which is a non-secretory vector. The gene is translated using its own ATG. The EcoRI-EcoRI fragment of Factor C insert, pEE21, was first cloned into the Eco RI site of the pHIL D2 vector. This construct was digested with Bgl II and Pml I to accomodate the BglII-EcoRV fragment of CrFC from the pGEM11Zf(+)/CrFC 21 to generate the full length insert in pHIL D2. This strategy was used to take advantage of the absence of Bgl II site in the pHIL D2 vector. Not I digestion of the vector allowed directional integration of the CrFC gene into the *P. pastoris* vector.

The λCrFC cDNAs were further manipulated and subcloned into various plasmid vectors. Firstly, for easier manipulations of the clones, the complete Factor C cDNAs that were originally cloned in λgt 22 (clones 21 (3448 bp) and 26 (4182 bp), each being flanked by multicloning sites: Eco RI and Not I) were recloned into plasmid, pGEM11Zf (+) to give pGEM11Zf(+)/CrFC 21 and pGEM11Zf(+)/CrFC 26, respectively. The recloning strategy is outlined in FIG. 13. Secondly, restriction digestions of the Factor C insert in recombinant clone λCrFC 21 with Sal I and Not I yielded a 2.4 kb fragment which was then subcloned into expression vector pGEMEX-1 (FIG. 14). Thirdly, digestion of λCrFC 21 with Bgl II and Eco RV resulted in a 3388 bp Factor C insert which was subcloned into pET 3b expression vector pAR 3039 that was previously linearized using Bam HI and Eco RV (FIG. 15). Fourthly, since the gene may not be apparently expressed at detectable levels in vivo in the *E. coli* host (possibly due to activation of the gene product by the Gram negative host bacterial endotoxin, resulting in the active Factor C being toxic to the host), the CrFC 26 was also inserted into yeast shuttle secretory (YEpsec1) and non-secretory (pEMBLyex4) expression vectors (FIG. 16). The CrFC 21 and CrFC 26 were further excised from their pGEM11Zf(+) vector and subcloned into vectors capable of transforming them into the methylotrophic yeast, *Pichia pastoris* (FIG. 17). The superiority of the *P. pastoris* system lies in the AOX1 promoter-driven expression of the Pichia vectors, which would result in high levels of expression of the CrFC cDNAs. The rationale behind the use of the yeast system is that (a) the gene under study is from a higher eukaryote whose product needs to be post-translationally modified, and (b) advantage will be taken of the absence of endotoxin in the yeast host to obtain the inactive Factor C proenzyme.

cDNAs And Proteins For Factor C

Each of the nucleic acid sequences and polypeptides disclosed herein, or their biologically functional equivalents, can be used in accordance with the present invention. The term "biologically functional equivalents," as used herein, denotes nucleic acid sequences and polypeptides exhibiting the same or similar biological activity as the particular nucleic acid sequences and polypeptides described herein.

For example, the nucleic acid sequences described herein can be altered by base substitutions, additions, or deletions to produce biologically functionally equivalent nucleic acids that encode proteins exhibiting Factor C enzymatic activity in endotoxin assays. In addition, due to the degeneracy of the genetic code, other DNA sequences that encode substantially the same amino acid sequences as described herein exhibiting Factor C enzymatic activity in endotoxin assays may be used in the practice of the present invention. These include, but are not limited to, nucleotide sequences comprising all or portions of the Factor C cDNAs described herein which are altered by the substitution of different codons that encode a physiologically functionally equivalent amino acid residue within the sequence, thus producing a silent change. Similarly, the Factor C proteins, or derivatives thereof, of the present invention include, but are not limited to, those containing all of the amino acid sequences substantially as described herein, including altered sequences in which functionally equivalent amino acid residues are substituted for residues within the sequence, resulting in a silent change. For example, one or more amino acid residues within the sequence can be substituted with another amino acid of similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The variants of Factor C cDNAs and proteins contemplated herein should possess more than 75% homology, preferably more than 85% homology, and most preferably more than 95% homology, to the naturally occurring Factor C cDNAs and proteins discussed herein. To determine this homology, two proteins are aligned so as to obtain a maximum match using gaps and inserts. Homology is determined as the product of the number of matched amino acids divided by the number of total amino acids plus gaps and inserts, multiplied by 100.

Also included within the scope of the present invention are Factor C fragments or derivatives thereof which are differentially modified during or after translation, e.g., by glycosylation, proteolytic cleavage, etc.

In addition, the recombinant Factor C-encoding nucleic acid sequences of the present invention may be engineered so as to modify processing or expression of Factor C. For example, and not by way of limitation, a signal sequence may be inserted upstream of Factor C encoding sequences to permit secretion of Factor C, and thereby facilitate harvesting or bioavailability.

Additionally, a given Factor C isoform or mutein can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including, but not limited to, in vitro site-directed mutagenesis (Hutchinson et al. (1978) *J. Biol. Chem.* 253:6551), use of TAB® linkers (Pharmacia), etc.

Expression Vectors For Factor C

The vectors contemplated for use in the present invention include those into which a DNA sequence as discussed herein can be inserted, along with any necessary operational elements. Such vectors can then be subsequently transferred into a host cell and replicated therein. Preferred vectors are those whose restriction sites have been well documented and which contain the operational elements preferred or required for transcription of the DNA sequence.

Certain embodiments of the present invention employ vectors which would contain one or more of the DNA sequences described herein. It is preferred that all of these vectors have some or all of the following characteristics: (1) possesses a minimal number of host-organism sequences; (2) be stably maintained and propagated in the desired host; (3) be capable of being present in high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) contain a DNA sequence capable of terminating transcription.

The cloning vectors capable of expressing the DNA sequences of the present invention contain various operational elements. These "operational elements" can include at least one promoter, at least one initiator codon, and at least one termination codon. These "operational elements" may also include one or more of the following: at least one operator, at least one leader sequence for proteins to be exported from intracellular space, at least one gene for a regulator protein, and any other DNA sequences necessary or preferred for appropriate transcription and subsequent translation of the cloned Factor C DNA.

Certain of these operational elements may be present in each of the preferred vectors of the present invention. It is contemplated that any additional operational elements which may be required may be identified and added to these vectors using methods known to those of ordinary skill in the art, such as those described by Sambrook et al. (1989) *Molecular Cloning, A Laboratory Manual*, Second Edition, Cold Spring Harbor Laboratory Press.

Regulators

Regulators serve to prevent expression of the DNA sequence in the presence of certain environmental conditions and, in the presence of other environmental conditions, will allow transcription and subsequent expression of the protein coded for by the Factor C DNA sequences. Regulatory segments can be inserted into the vector such that expression of the DNA sequence will not occur, or will occur to a greatly reduced extent. Expression of the desired protein is induced by addition of a substance to the environment capable of causing expression of the DNA sequence after the desired cell density has been reached.

Promoters

The expression vectors must contain promoters which can be used by the host cell for expression of its own proteins. Many promoters have been isolated and characterized, enabling one skilled in the art to use them for expression of the recombinant Factor C forms.

Transcription Terminators

The transcription terminators contemplated herein serve to stabilize the vector. Those sequences described by Rosenberg et al. (1979) *Ann. Rev. Genet.* 13:319–353 can be used in the present invention.

Non-translated Sequences

It may also be desirable to construct the 3' or 5' end of the coding region to allow incorporation of 3' or 5' non-translated sequences into the cDNA transcript. Included among these non-translated sequences are those which stabilize mRNA, as disclosed by Schmeissner et al. (1984) *J. Mol. Biol.* 176:39–53.

Leader Sequences and Translational Couplers

Additionally, DNA coding for an appropriate secretory leader (signal) sequence can be present at the 5' end of the DNA sequence, as set forth by Watson, M.E. in *Nucleic Acids Res.* 12:5145–5163, if the protein is to be excreted from the host cytoplasm. The DNA for the leader sequence must be in a position that allows the production of a fusion protein in which the leader sequence is immediately adjacent to and covalently joined to Factor C, i.e., there must be no transcription or translation signals between the two DNA coding sequences.

In some species of hosts, the presence of an appropriate leader sequence will allow transport of the completed protein into the periplasmic space. In the case of some Saccharomyces, the appropriate leader sequence will allow transport of the protein through the cell membrane and into the extracellular medium. In this situation, the protein may be purified from other extracellular proteins.

Translation Terminators

The translation terminators contemplated herein serve to stop the translation of mRNA. They may be either natural, as described by Kohli, J., *Mol. Gen. Genet.* 182:430–439, or synthetic, as described by Pettersson, R.F. (1983) *Gene* 24:15–27.

Selectable Markers

Additionally, the cloning vectors contemplated herein can contain a selectable marker, such as a drug resistance marker or other marker which causes expression of a selectable trait by the host cell.

Such a drug resistance or other selectable marker facilitates the selection of transformants. Additionally, the presence of such a selectable marker in the cloning vector may be of use in keeping contaminating microorganisms from multiplying in the culture medium. A pure culture of the transformed host cells would be obtained by culturing the cells under conditions which require the induced phenotype for survival. The operational elements discussed herein are routinely selected by those of ordinary skill in the art in light of prior literature, including Sambrook et al., discussed supra, and the teachings contained herein. General examples of these operational elements are set forth in B. Lewin (1983) *Genes*, Wiley & Sons, New York. Various examples of suitable operational elements may be found in the vectors discussed above, and may be gleaned via review of the publications discussing the basic characteristics of the aforementioned vectors.

Upon synthesis and isolation of all the necessary and desired component parts, the vector can be assembled by methods generally known to those of ordinary skill in the art. Assembly of such vectors is within the ordinary skill in the art, and, as such, is capable of being performed without undue experimentation.

Multiple copies of the DNA sequences of the present invention and their accompanying operational elements may be inserted into each vector. In such case, the host cell would produce greater amounts per vector of the desired form of Factor C. The number of multiple copies of the DNA sequence which may be inserted into the vector is limited only by the ability of the resultant vector, due to its size, to be transferred into and replicated and transcribed in an appropriate host cell.

Host Cells

Vectors suitable for use in various host cells are contemplated for use in the present invention. Such host cells include, for example, *E. coli*, yeasts such as *Saccharomyces cerevisiae* and *Pichia pastoris*, Baculovirus, and mammalian cells, including, for example, Chinese Hamster Ovary cells.

In the case of yeasts, useful promoters include Gal 1 and 10, Adh 1 and 11, and Pho 5. Transcription terminators can be chosen from among Cyc, Una, Alpha Factor, and Sac 2. Transcriptional start sites and leader peptides can be obtained from the invertase, acid phosphatase, and Alpha factor genes. Useful selection markers are Ura 3, Leu 2, His 3, and Tap 1.

In the case of expression in mammalian cells, the DNA encoding the present forms of Factor C should have a sequence efficient at binding ribosomes. Such a sequence is described by Kozak in *Nucl. Acids Res.* (1987) 15:8125–8132. The Factor C-encoding fragment can be inserted into an expression vector containing a transcriptional promoter and a transcriptional enhancer as described by Guarente in *Cell* (1988) 52:303–305 and Kadonaga et al. (1987) *Cell* 51:1079–1090. A regulatable promoter as in the Pharmacia plasmid pMSG can be used, if necessary or desired. The vector should also possess a complete polyadenylation signal as described by Ausubel et al. (1987) in *Current Protocols in Molecular Biology*, Wiley, so that mRNA transcribed from the vector is properly processed.

In order to select a stable cell line that produces Factor C as described herein, the expression vector can carry the gene for a selectable marker such as a drug resistance marker or a complementary gene for a deficient cell line, such as a dihydrofolate reductase (dhfr) gene for transforming a dhfr⁻ cell line, as described by Ausubel et al., supra. Alternatively, a separate plasmid carrying the selectable marker can be cotransformed along with the expression vector.

Vectors for mammalian cells can be introduced therein by several techniques, including calcium phosphate:DNA coprecipitation, electroporation, or protoplast fusion. Coprecipitation with calcium phosphate as described by Ausubel et al., supra, is the preferred method.

By way of example, vectors and host cells contemplated for the heterologous expression of the Factor C cDNAs disclosed herein include the use of the T7 system in pGEMEX1, pET3b(pAR3039), and pGEM11Zf(+), and the GST system in pGEX1,2,3. The host cells can be chosen from among JM109, JM109(DE3), DH5α, HMS174(DE3) plysS, and λCE6(phage).

For expression in *Pichia pastoris*, the host strain can be GS115, and useful vectors are pHIL D2, pPIC 9, and pHIL S1.

For expression in the Baculovirus system, host cells can be *Spodoptera frugiperda* SF9 and SF21; the vectors can be pBlue Bac His, A, B, C; pBlue Bac III; pVL1392; pVL 1393; and pAC360. The host for initial cloning can be *E. coli* DH5α, JM109, or TOP 10F.

For expression in mammalian cells, the vector for transfection can be pCDNAI, wherein all initial cloning is in *E. coli* MC1061/PE3. Mammalian host cells can be African green monkey derived COS1 or COS7 cells which express the SV40 large T antigen. The mouse fibroblast cell line NIH3T3, which also expresses the SV40 large T antigen, can also be used.

EXAMPLE 9

Expression of Factor C cDNA Constructs In Vitro

Figure 18A:
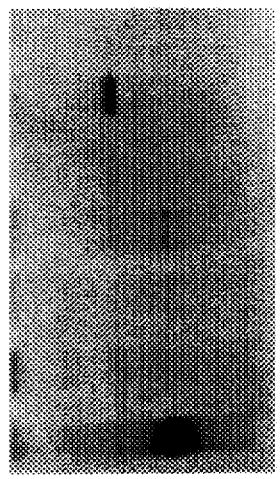
FIG. 18 shows the products of in vitro cell-free expression of CrFC cDNA constructs in plasmid vectors containing $T_7$ promoters. The Promega in vitro transcription and translation (TnT T7 coupled reticulocyte lysate) system was used to test the expression potentials of 2 μg each of these constructs. $^{35}$S-cys was used to label the translation products. The Factor C proteins were either produced as fusion or non-fusion proteins depending on their vectors: pGEMEX-1/CrFC 21 (Factor C insert coding sequence of 2036 bp+780 bp of fusion gene in vector) yielded a Factor C-fusion protein of 103 kDa; pGEM11Zf(+)/CrFC21 (Factor C insert coding sequence of 3083 bp) yielded a protein of 113 kDa; pEE21 (pGEM11Zf(+)/CrFC 21, containing 2300 bp Eco RI-Eco RI fragment of Factor C coding insert) yielded an 85 kDa protein; pGEM11Zf(+)/CrFC 26-6a and -9a (deletion mutants of CrFC 26, harbouring 3421 bp and 3462 bp, respectively, of Factor C insert coding sequence) each yielded limited amounts of Factor C of 113 kDa; pET3b/CrFC 21 (Factor C insert coding sequence of 3023 bp+30 bp fusion gene 10 of the vector) yielded a Factor C-fusion protein of 112 kDa; pGEM11Zf(+)/CrFC 26 (with full-length Factor C insert of 4182 bp, intact with the 5' untranslated region containing the 7 false start codons) did not express any Factor C protein. Positive control: luciferase gene gave the expected protein of 61 kDa. Negative control: pGEMEX-1 vector expressed a 28 kDa fusion protein.
Figure 18B:
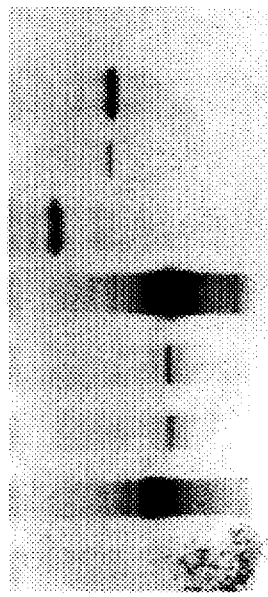

The CrFC cDNAs subcloned into pGEM11Zf(+), pGEMEX-1, and pET 3b were subjected to in vitro transcription and translation using the Promega transcription and translation system (TnT $T_1$ coupled rabbit reticulocyte lysate). The expression of the cDNA inserts was driven by T7 promoter in their respective vectors. Using 2 µg each of the recombinant DNA construct, variable rates of transcription and translation were observed, giving the expected sizes of either fusion or non-fusion Factor C gene products (FIG. 18). These results therefore demonstrate that the CrFC cDNAs were subcloned in frame with their $T_7$ promoters. The pGEM11Zf(+)/CrFC 26 full-length cDNA was not expressed, possibly due to its high number of false start codons (see FIG. 6).

The deletion subclones of CrFC 26, viz., pGEM11Zf(+)/CrFC 26–6a and –9a, which lack the 5' untranslated region of CrFC 26, were better expressed, yielding faint bands of Factor C proteins. Deletion subclones 6a and 9a were created by carrying out 5' –3' Exo III nuclease mutagenesis on the Eco RI fragment of CrFC 26 cDNA which had been cloned into the unique Eco RI site of pGEM11Zf(+). In order to perform the deletion mutagenesis, the recombinant clones was first digested with Not I, and the recessed ends Klenow-filled with α-phosphorothioate nucleotides to create a protected site resistant to Exo III nuclease digestion. The clone was then subsequently digested with Xba I to create a sensitive site from which Exo III nuclease digestion could initiate. The deletion mutagenesis was carried out at 30° C., and aliquots of the reaction mixture were removed at 30-second intervals to produce a series of deletion mutants. Subclones containing deletions of appropriate sizes were sequenced using Sanger's dideoxy method. Deletion subclones 6a and 9a were selected for expression analyses because they contain complete deletions of the 5' untranslated DNA sequence, and also partial deletions of the DNA sequence encoding the putative leader peptide. Deletion subclone 9a starts at nucleotide position 721, while subclone 6a starts at nucleotide position 762. Complete deletion of the 5' untranslated DNA sequence from both sublclones is expected to release their expression from the control of any translational signals which may be encoded in the 5' untranslated sequence. Manipulation of the CrFC 26 sequence to eliminate some or all of the false start codons is therefore expected to produce deletion subclones which can be successfully expressed, producing active Factor C.

On the other hand, the pGEM11Zf(+)/CrFC 21 full-length cDNA construct is more efficiently expressed than its CrFC 26 counterparts because CrFC 21 has the true ATG and Kozak consensus sequence belonging to the CrFC 21 cDNA insert itself, which makes it more complete and translatable. The 6a and 9a constructs were not driven by the CrFC 26's own true ATG. Rather, The ATG in both cases was present in the multicloning site of pGEM11Zf(+). However, in pGEMEX-1 vector, CrFC 21 (pGEMEX-1/CrFC 21 construct) yielded the highest level of incorporation of $^{35}$S-cys and a correspondingly more intense band of translated Factor C gene product. This may be due to the fact that the fusion 260 amino acids code for the $T_7$ gene10 capsid protein and is thus best transcribed under its own $T_7$ promoter using the compatible $T_7$ RNA polymerase. This efficient expression of CrFC 21 was also observed in pET 3b vector.

These results indicate that the present CrFC cDNA recombinant clones can be expressed in heterologous systems, depending on the manner of insertion of the cDNAs into appropriate vectors.

Purification of Factor C Proenzyme

Attempts to purify Factor C proenzyme from amoebocyte lysates have often been hampered by the ubiquitous endotoxin which activates the zymogen into an active serine protease enzyme. This results in poor yields as well as considerable loss of enzymatic activity. In order to improve the purification procedure, dimethylsulfoxide, Me$_2$SO, and chelating agents, such as EDTA, have been incorporated in the buffer solution to prevent the premature activation of the cascade reaction during purification. This has led to a simple and unique procedure for concomitantly purifying two isoforms of Factor C precursor enzymes, with a corresponding amelioration of their total yields and specific activities. The data presented infra show that both the single- and double-chain forms of the enzyme have endotoxin receptors to which endotoxin binds to activate their catalytic sites. Data presented infra also show that these endotoxin-binding sites in Factor C are competitively but reversibly occupied by Me$_2$SO in the range of from about 5% to about 30% when the latter is added during purification.

EXAMPLE 10

Preparation of Amoebocyte Lysate from *C. rotundicauda*

Horseshoe crabs were bled by cardiac puncture as previously described by Jorgensen and Smith, 1973. *Appl. Microbiol.* 26, 43–48. Blood was collected into a solution of 0.125% N-ethylmaleimide/3% NaCl (w/v) and centrifuged at 150× g for 30 min at 26° C. Amoebocytes were washed with 3% NaCl and lysed overnight with pyrogen-free water at 4° C. The lysate was lyophilized by freeze-drying.

EXAMPLE 11

Purification of Single- and Double-Chain Factor C Proenzymes

The first step in the purification of Factor C is as previously reported (Navas et al., 1990. *Biochem. Intl.* 21, 805–813), except for the addition of Me$_2$SO, preferably in an amount of about 5%, v/v, and a chelating agent, such as EDTA, preferably in an amount of about 1 mM, in the gel filtration buffer. Freeze-dried Carcinoscorpius amoebocyte lysate (CAL) containing 326 mg total protein was reconstituted in 4 ml pyrogen-free water before fractionation on Sepharose CL-6B (2.6×97 cm) which was previously equilibrated with 0.05M Tris-HCl, pH 8.0, containing 0.154M NaCl 5% Me$_2$SO (v/v), and 1 mM Na$_2$EDTA. The flow rate was maintained at 20 ml/h. The fractions for each peak were pooled separately and lyophilized. The freeze-dried fractions were reconstituted in pyrogen-free water and desalted through Sephadex G-25 (1×6 cm) packed in a BioRad 10-DG column using pyrogen-free water as the mobile phase. Desalting effected the removal of Me$_2$SO together with all the other salts from the enzyme fractions. Me$_2$SO apparently hinders the binding of Factor C to the subsequent affinity column. The desalted enzyme fractions were separately subjected to affinity chromatography through a heparin-Sepharose CL-6B column (1×11 cm) at 25° C. using the Pharmacia FPLC system. The mobile phase contained 0.02M Tris-HCl, pH 8.0, with 1 mM Na$_2$EDTA. Protein ($A_{280nm}$) was eluted with a linear gradient of 0–0.5M NaCl at a flow rate of 0.75 ml/min and immediately stored at 4° C. This step essentially purified single-chain Factor C to apparent homogeneity, while double-chain Factor C was still co-eluted with proclotting enzyme. The fractions containing the double-chain Factor C were pooled and concentrated to a volume of 0.2 ml, and further purified by gel filtration in a Pharmacia FPLC Superose 12 column (HR 10/16) using 0.02M Tris-HCl, pH 8.0, containing 1 mM Na$_2$EDTA as the mobile phase.

Figure 19A:
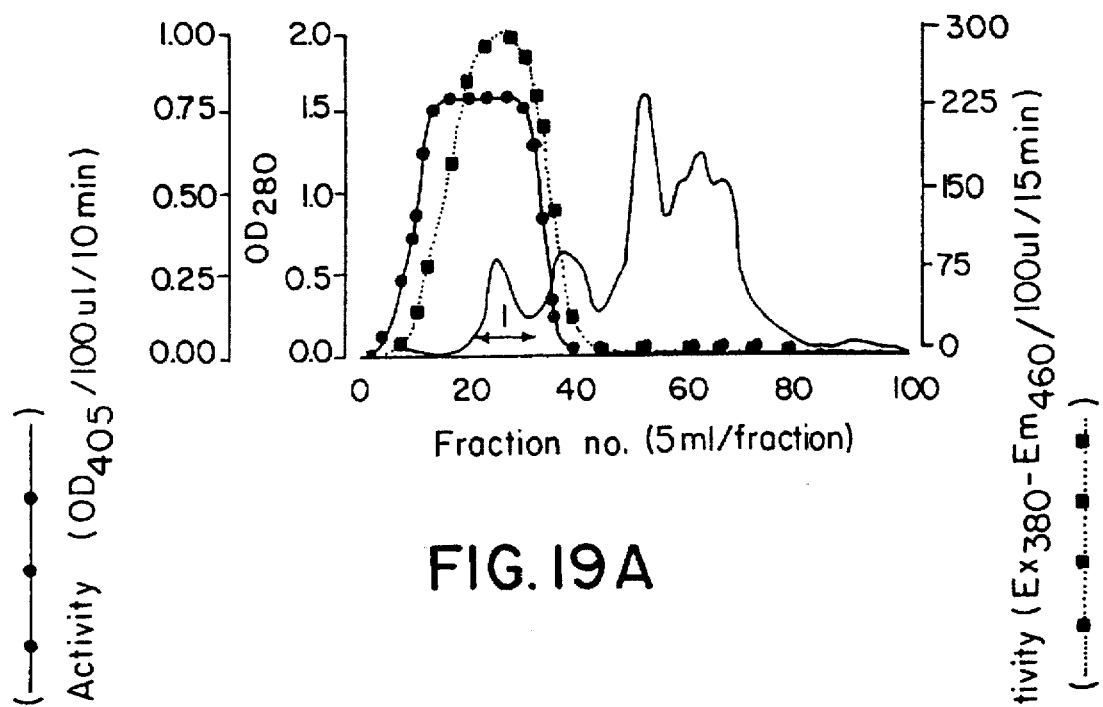
FIG. 19(a) shows the elution profile of whole CAL lysate chromatographed on Sepharose CL-6B (2.6×97 cm) equilibrated with 0.05M Tris-HCl pH 8.0, containing 0.154M NaCl.
Figure 19B:
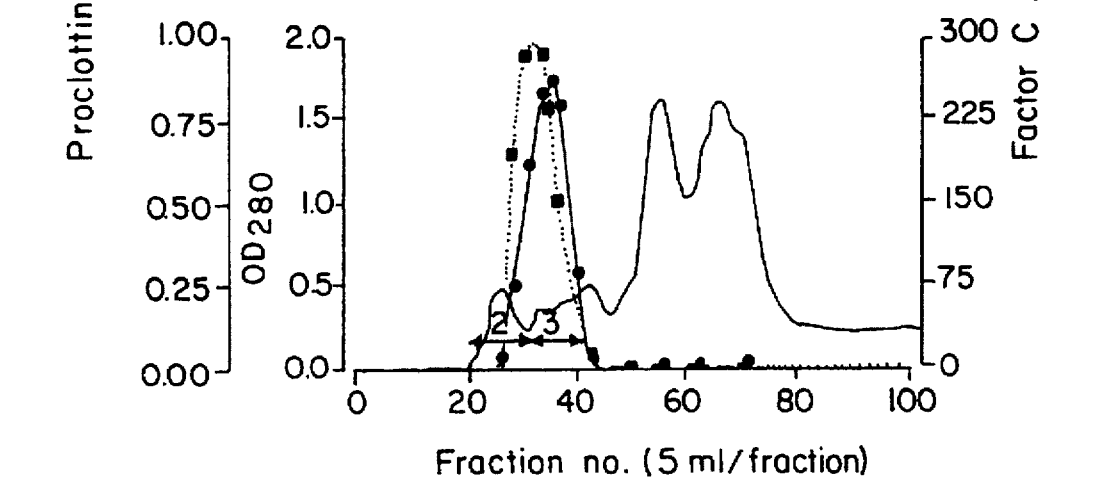
FIG. 19(b) shows the elution profile with the addition of 5% $Me_2SO$ and 1 mM Na2EDTA. A total of 326 mg CAL was loaded onto the column, which was run at a flow rate of 20 ml/h. Panel (a) shows Factor C (assayed according to Nakamura et al., 1986. *Eur. J. Biochem.* 154, 511–521) and proclotting enzyme (assayed according to Harada-Suzuki et al., 1982. *J. Biochem.* 92, 793–800) co-eluting over a broad range into the first peak. However, panel (b) shows narrower peaks of these enzyme activities. Double-headed arrows (←→) indicate all pooled fractions with corresponding electrophoretic profiles shown in FIG. 20.
Figure 20A:
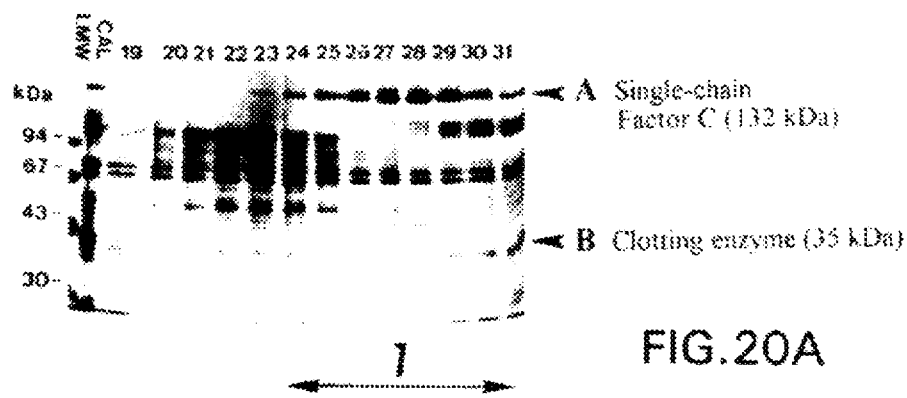
FIG. 20 shows reducing SDS-PAGE (8% polyacrylamide) analysis of protein fractions obtained from the Sepharose CL-6B column using buffers without (a) and with (b) 5% $Me_2SO$ and 1 mM $Na_2EDTA$. Fraction numbers are written on top of each lane, and double-headed arrows correspond to pooled fractions found in FIG. 19. A total amount of 15 μg protein was loaded into each lane. Low molecular weight (LMW) marker proteins were used to estimate the sizes of the protein bands of interest. In (a), single-chain Factor C (band A, 132 kDa) was shown to co-elute with the heavy chain of clotting enzyme (band B, 35 kDa). In (b), single-chain Factor C eluted separately (arrow 2) from the other enzymes, although no apparent activity was detected due to the presence of 5% $Me_2SO$, which inactivates single-chain Factor C activity (also see FIG. 25). The heavy chain (band C) and light chain (band D) of the double-chain Factor C were found in fractions 30 (►) onwards as demarcated by double-headed arrow No. 3. These fractions gave high enzyme activity as it was not inhibited by 5% $Me_2SO$ (refer to FIG. 19). The 52 kDa light-chain (band D) of the double-chain Factor C is glycosylated and is thus less intensely stained by Coomassie blue.
Figure 21:
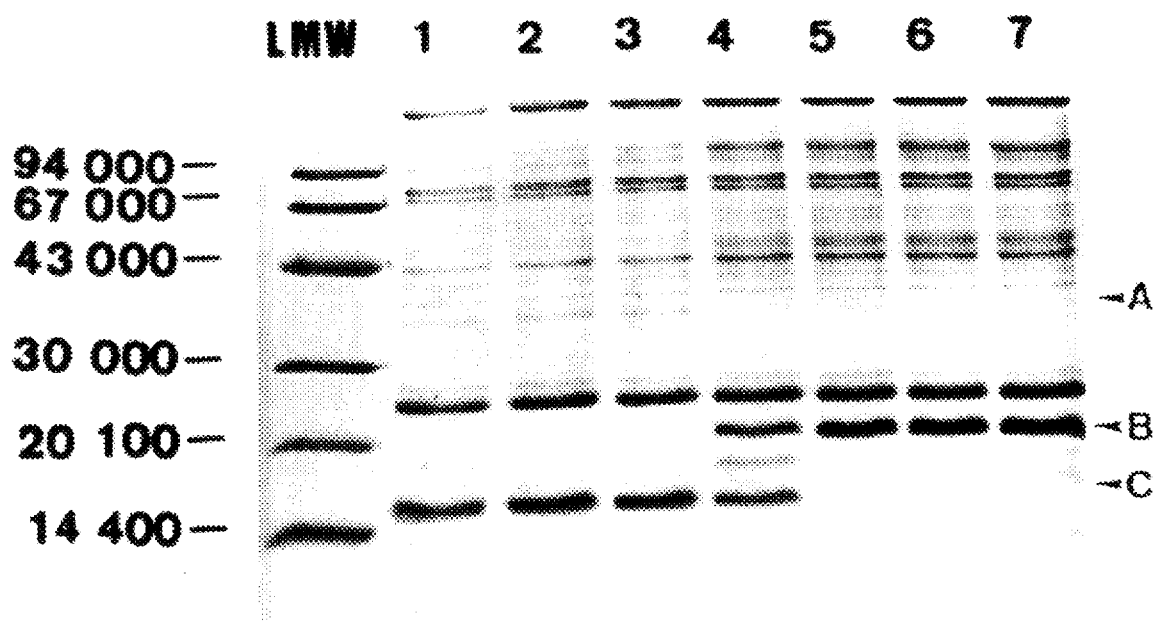
FIG. 21 shows routine preparations of Carcinoscorpius amoebocyte lysate analyzed on SDS-reducing PAGE (15%). The seven batches of lysate preparations were loaded in the PAGE gel in order of decreasing extent of autoactivation. Lanes 1–3 show the presence of the heavy chain of clotting enzyme (band A, 35 kDa), and complete conversion of coagulogen (band B, 21 kDa) to coagulin (band C, 17 kDa). Thus, appearance of bands A and C is indicative of autoactivation and poor lysate quality. On the other hand, lysates in lanes 5–7 are considered to be of high quality since no coagulin is apparent. Lane 4 shows a batch of lysate which is of intermediate quality and sensitivity in its detection of endotoxin.

The chromatograms from gel filtration (Sepharose CL-6B) of Factor C in the absence and presence of 5% Me$_2$SO and EDTA are compared in FIGS. 19a and 19b. In the absence of Me$_2$SO and EDTA, both Factor C and proclotting enzyme co-eluted in the first peak with an apparent native molecular mass of 495 kDa (FIG. 19a). This confirmed earlier observations (Wright and Jong, 1986. *J. Exp. Med.* 164, 1876–1888) that the coagulation enzymes, being glycoprotein in nature, tend to aggregate in the absence of a denaturing agent. The suspected single-chain Factor C (band A, FIG. 20a) was seen to be coincident with the $A_{280nm}$ elution profile of the first peak in FIG. 19a. However, the appearance of a band which corresponds to the heavy chain of the clotting enzyme (band B in FIG. 20a and band A in FIG. 21) implied that autoactivation (Nakamura et al., 1985. *J. Biochem.* 97, 1561–1574) occurred during the chromatography, thus suggesting that Factor C could have been transformed to its active form. Morever, it was also found that during some routine preparations of Factor C, coagulogen (band B, FIG. 21) was prematurely transformed to coagulin (band C, FIG. 21).

To circumvent this problem, the same chromatographic run was performed in the presence of Me$_2$SO and EDTA as shown in FIG. 19b. Under this condition, autoactivation was precluded and there was a substantial difference in the elution profile. A small protein peak, where both Factor C and proclotting enzyme were found to be concentrated, appeared between the first two peaks of the previous run. By SDS-PAGE analysis, single-chain Factor C (band A, FIG.

Figure 20B:
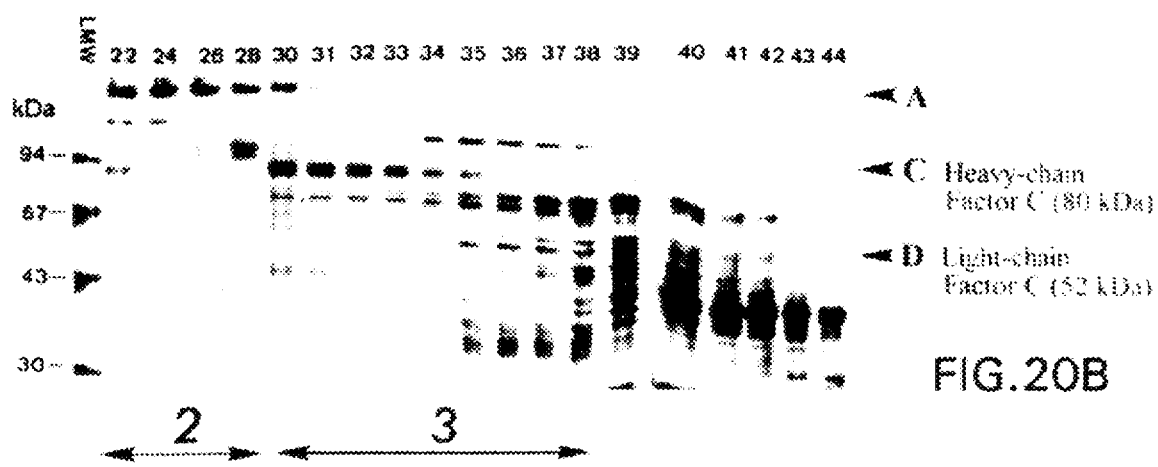
Figure 22A:
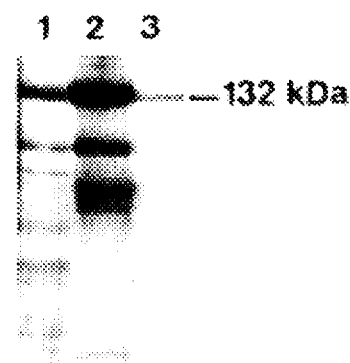
FIG. 22 shows affinity chromatography of pooled first peak fractions (refer to arrow 2, FIG. 19b) on a heparin-Sepharose CL-6B column (1×11 cm). The silver-stained electrophoretic gel profile shows: Lane 1, whole CAL; 2, pooled first peak fractions (arrow 2 in FIG. 19b and 20b); 3, single-chain Factor C.
Figure 22B:
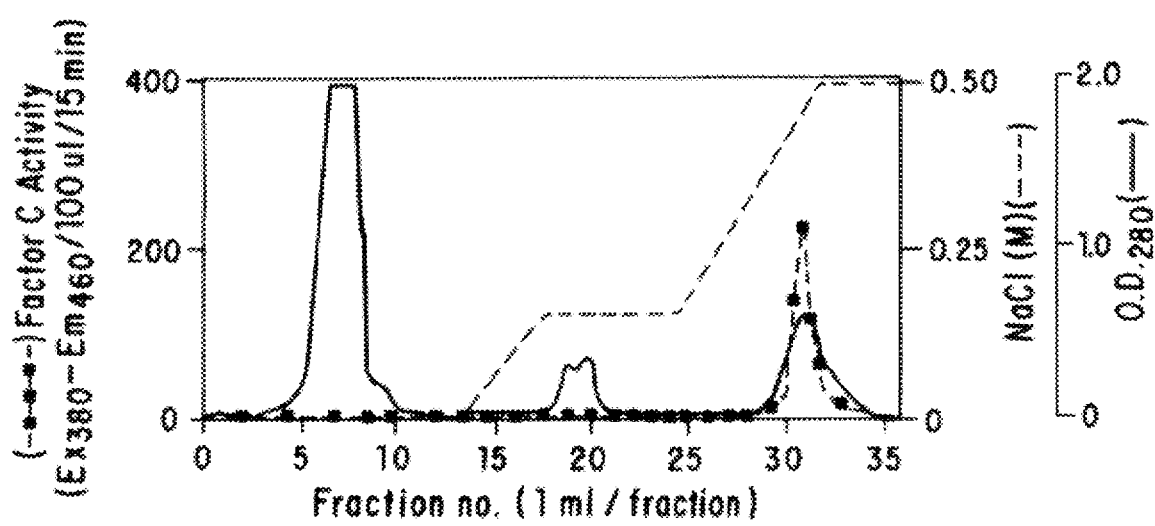
Figure 23A:
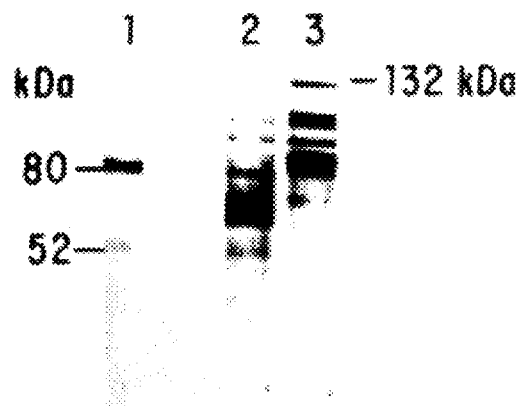
FIG. 23 shows the purification of double-chain Factor C by gel filtration on FPLC Superose 12 HR 10/30 column which was equilibrated at room temperature with a flow rate of 0.4 ml/min. The pooled enzyme fractions (lane 2) equivalent to 1.2 mg protein was loaded into the column. This was previously eluted from the heparin-Sepharose CL-6B column. The double-chain Factor C was eluted in a single tube (fraction 22), and the silver-stained reducing SDS-PAGE gel shows that it consists of 80 kDa and 52 kDa subunits (lane 1). The pooled first peak fractions (refer to arrow 2, FIG. 19b) containing the single-chain form is shown in lane 3. Each lane consists of 15 µg total protein.
Figure 23B:
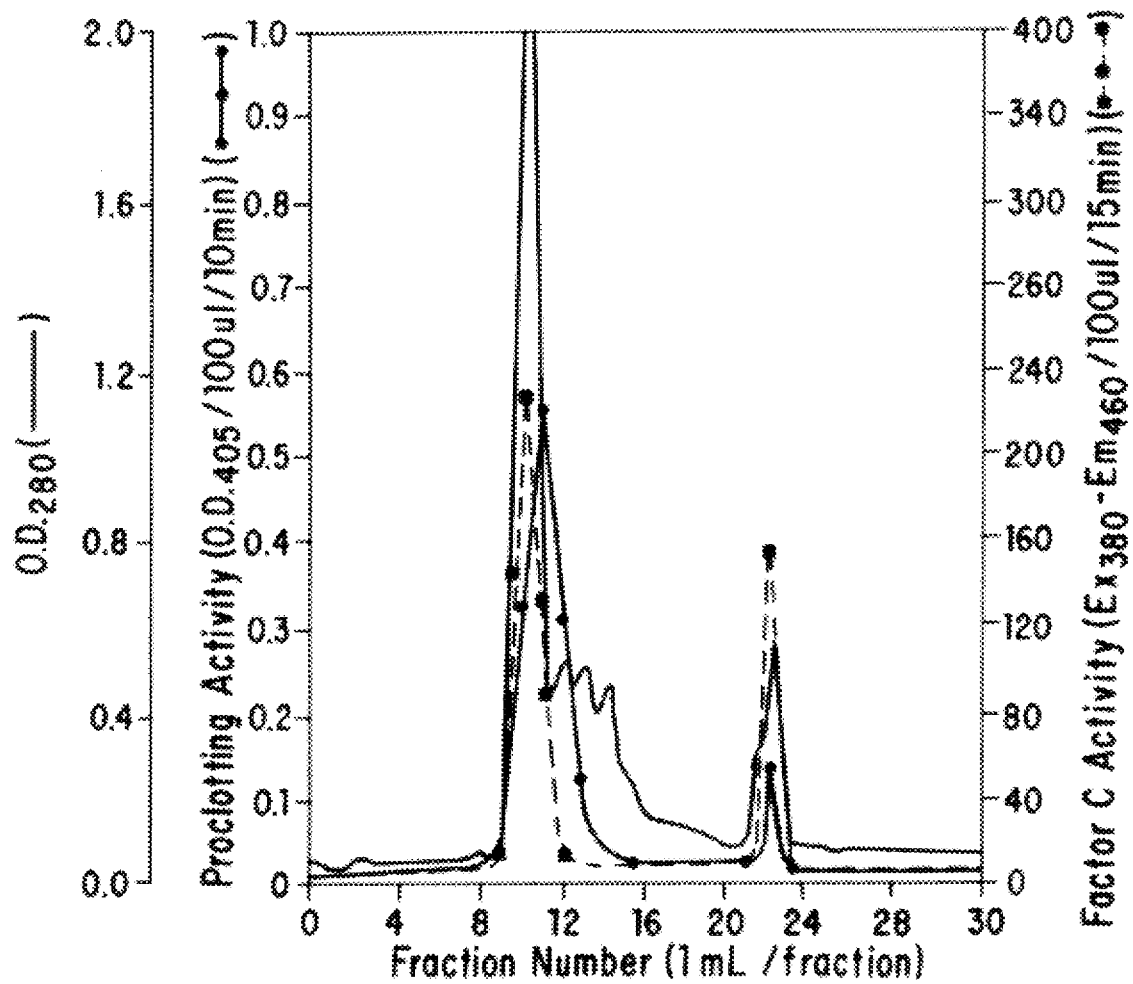
Figure 25:
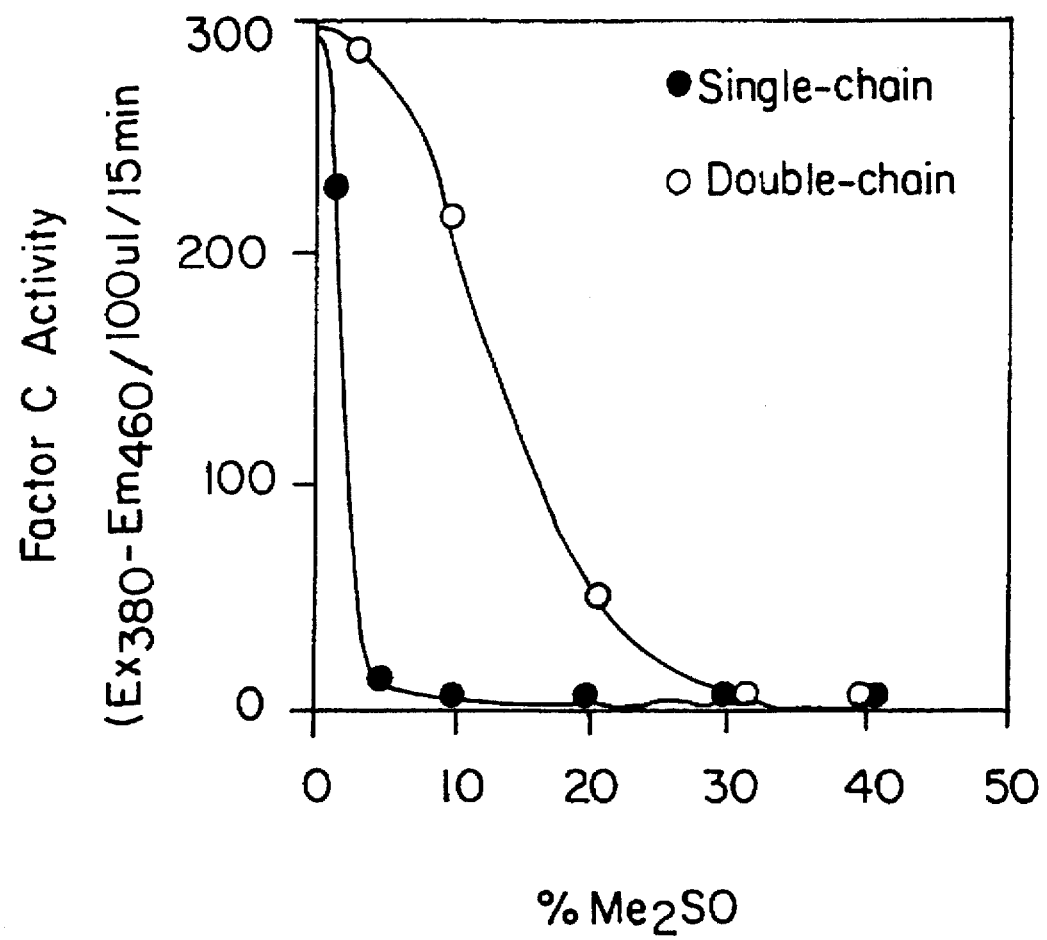
FIG. 25 shows the effect of increasing concentrations of $Me_2SO$ on the two forms of purified Factor C. Prior to the addition of the substrate, 5 µg of each enzyme was incubated for 1 h with 5 µg endotoxin. Single-chain Factor C was more susceptible, losing 95% of its activity at 5% $Me_2SO$, while double-chain Factor C was totally inactivated only at 30% $Me_2SO$.

20b) was also shown to be more well-separated from other contaminating proteins. However, in the presence of Me$_2$SO and EDTA, this band of single-chain Factor C did not seem to exhibit any activity. Instead, another form of Factor C was suspected to be responsible for such activity coincident with fractions 30–38 (bands C and D, FIG. 20b). This was attributable to the heavy- and light-chain, respectively, of the double-chain form of Factor C. Both peaks 2 and 3 in FIG. 19b were separately pooled, concentrated, and subjected to desalting through Sephadex G-25 using pyrogen-free water as eluent. With the removal of Me$_2$SO, the pooled first peak fractions regained a considerable amount of Factor C activity, contributing 30% of the total. This can be explained by earlier kinetic studies (Navas et al., 1990. *Biochem. Intl.* 21, 805–813) which showed that Me$_2$SO reversibly inactivates single-chain Factor C by binding to its endotoxin receptor site. Furthermore, single-chain Factor C was found to be more enriched at this stage, as compared to that in the previous purification. FIG. 22 shows the elution profile of single-chain Factor C. By this method, single-chain Factor C was purified 563-fold, to apparent homogeneity, giving a yield of 41% (Table II). By the same method, however, the double-chain Factor C still co-eluted with proclotting enzyme. Thus, further purification performed by gel filtration on Superose 12 using FPLC (FIG. 23) finally isolated the double-chain Factor C, giving 1520-fold purification (Table III).

were found to possess properties typical of serine proteases. In particular, both were irreversibly inhibited by small amounts of DFP and PMSF. However, both forms of Factor C reacted differently in the presence of Me$_2$SO. Single-chain Factor C was highly susceptible to Me$_2$SO, being almost completely inhibited by 5% Me$_2$SO, whereas double-chain Factor C activity was completely inhibited only at 30% Me$_2$SO (FIG. 25). Being more susceptible to Me$_2$SO, single-chain Factor C did not exhibit any apparent activity during the initial gel filtration step, where the Factor C assay was performed in the presence of 5% Me$_2$SO. This differential sensitivity of the two forms of Factor C to Me$_2$SO was instrumental in distinguishing the assay of one form from the other, and in the final purification simultaneously, of the two forms of Factor C. Thus, Me$_2$SO4 in the range of from about 5% to about 30%, v/v, can be used to inhibit Factor C.

EXAMPLE 12

Endotoxin Binding Assay

To test the presence of endotoxin (LPS) binding sites on Factor C, 10 μg aliquots of endotoxin were electrophoresed in duplicate in 15% polyacrylamide gels containing SDS. One set was silver stained according to the method of Tsai and Frasch, 1982. *Anal. Biochem.* 119, 115–119, while the other was electroblotted onto an Immobilon PVDF membrane (Millipore) using the same procedure as described above. The electroblotted membrane containing endotoxin was blocked by incubating in 50 mM Tris-HCl, pH 8.0, containing 0.2M NaCl (TBS) with 30 mg/ml BSA for 30 min at 37° C. The membrane was cut into strips (LPS strips), and each strip was separately incubated with slight agitation at 37° C. with 5 μg each of purified single-chain and double-chain Factor C fractions. The strips were then washed three times for 5 min each with TBS before incubation for 3 h at 37° C. with rabbit anti-CAL antiserum diluted 500-times in TBS containing 1 mg/ml BSA. A control experiment was carried out by incubating replicate LPS strips earlier treated with single- or double-chain Factor C with pre-immune rabbit serum instead of rabbit anti-CAL antiserum.

TABLE II

Purification of single-chain Factor C
Factor C activity from the Sepharose CL-6B column was determined after desalting the protein fractions through Sephadex G-25 in order to reactivate the enzyme by the removal of DMSO.

| | | Protein | | | Enzyme | | | |
|---|---|---|---|---|---|---|---|---|
| Purification step | Volume (ml) | mg/ml | Total (mg) | U/ml | Total (U) | U/mg | Recovery (%) | Purification (-fold) |
| CAL | 4 | 81.50 | 326.00 | 74.25 | 297 | 0.91 | 100 | 1 |
| Sepharose CL-6B | 40 | 0.04 | 1.60 | 5.82 | 233 | 155.33 | 78 | 171 |
| Heparin Sepharose CL-6B | 5 | 0.05 | 0.25 | 24.54 | 123 | 512.50 | 41 | 563 |

TABLE III

Purification of double-chain Factor C

| | | Protein | | | Enzyme | | | |
|---|---|---|---|---|---|---|---|---|
| Purification step | Volume (ml) | mg/ml | Total (mg) | U/ml | Total (U) | U/mg | Recovery (%) | Purification (-fold) |
| CAL | 4.0 | 81.50 | 326.00 | 74.25 | 297 | 0.91 | 100 | 1 |
| Sepharose CL-6B | 35.5 | 0.08 | 2.84 | 7.21 | 256 | 90.14 | 86 | 99 |
| Heparin Sepharose CL-6B | 5.0 | 0.24 | 1.20 | 36.84 | 184 | 153.33 | 62 | 168 |
| Superose 12 | 1.0 | 0.06 | 0.06 | 83.00 | 83 | 1383.33 | 28 | 1520 |

Figure 24:
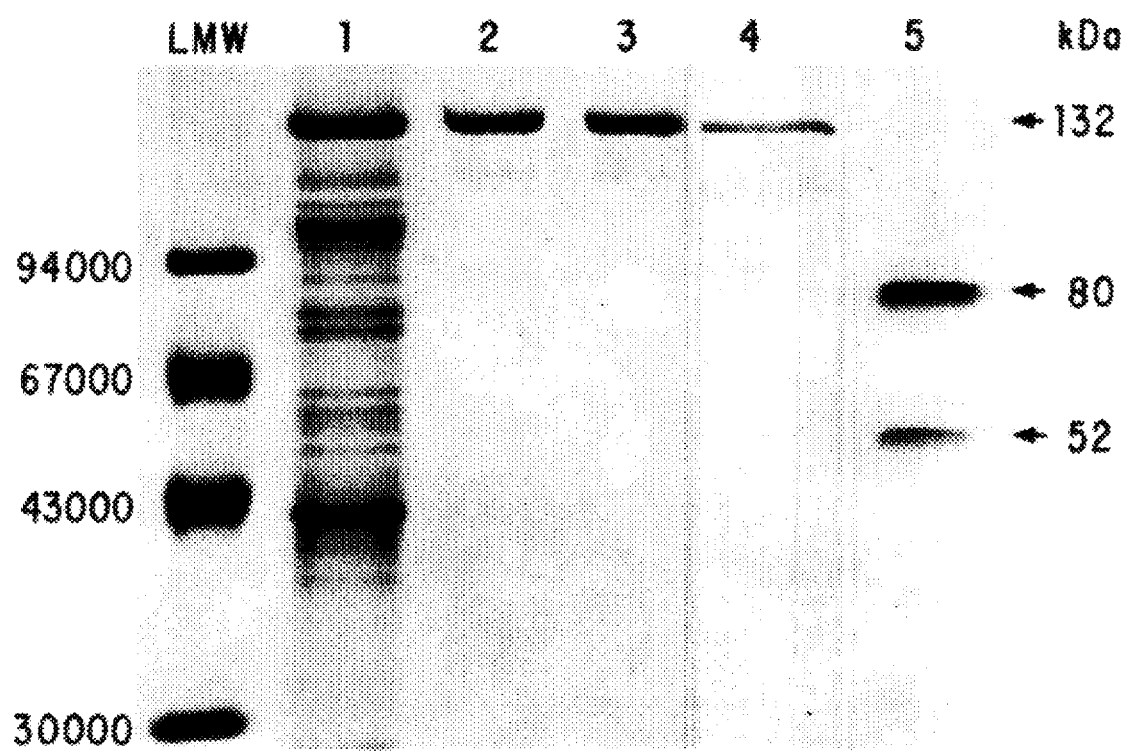
FIG. 24 shows a comparison of single-chain (lanes 2 and 4) and double-chain (lanes 3 and 5) forms of Factor C electrophoresed in SDS-PAGE in the absence (lanes 2 and 3) and presence (lanes 4 and 5) of β-mercaptoethanol. Lane 1 contained 15 µg of CAL.

By non-reducing and reducing SDS-PAGE analysis, the single-chain Factor C remained as a single polypeptide with a calculated apparent molecular mass of 132 kDa (FIG. 24, lanes 2 and 4), while its double-chain form was found to be composed of a heavy (80 kDa) and a light chain (52 kDa) when resolved under reducing SDS-PAGE (FIG. 24, lane 5). The molecular masses reported here are slightly heavier than those reported for *T. tridentatus* (Nakamura et al., 1986. *Eur. J. Biochem.* 154, 511–521). Comparing the effective sizes of their component chains, it is apparent that the light chain of the enzyme from *C. rotundicauda* was heavier than that from *T. tridentatus*. Both forms of Factor C from *C. rotundicauda*

Subsequently, the strips were washed with TBS, followed by incubation for 1 h at 37° C. with peroxidase-conjugated goat anti-rabbit IgG (Zymed) in TBS with 1 mg/ml BSA. After rinsing extensively, the strips were stained with 60 µl $H_2O_2$ and 60 mg chloro-1-napthol (Sigma) in 20% methanol (v/v).

Figure 26A:
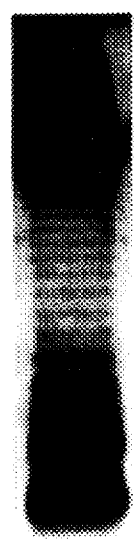
FIG. 26 shows endotoxin binding assay of Factor C. Panel A shows silver-stained endotoxin electrophoresed under reducing conditions on a 15% polyacrylamide gel. Panel B shows a modified Western blot where 10 µg of electrophoretically resolved endotoxin was electroblotted onto a PVDF membrane (LPS strips), reacted with single-chain (lane 1) and double-chain Factor C (lane 2) followed by whole CAL antibody and stained with peroxidase-conjugated goat anti-rabbit antibody. The stained portions indicate the lipid A moiety which is known to be the functional component of endotoxins that specifically binds Factor C (Lei and Morrison, 1988. *J. Immunol.* 141, 996–1011). Control LPS-strips, with bound single- or double-chain Factor C incubated with normal rabbit serum did not show any hybridization.
Figure 26B:
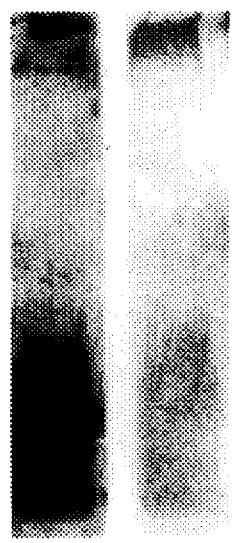

FIG. 26 shows that LPS electroblotted to an Immobilon membrane was recognized by both the single-and double-chain Factor C. The single-chain Factor C showed higher capacity for binding to LPS as indicated by the stronger hybridization signal (FIG. 26B, lane 1) compared to its double-chain counterpart. Since LPS and $Me_2SO$ bind to the same receptor on Factor C, this observation is supported by the earlier finding of the higher susceptibility of single-chain Factor C to $Me_2SO$ (FIG. 25), which completely but reversibly inhibited the activation of Factor C, causing steric hindrance which renders it non-functional (Navas et al., 1990. *Biochem. Intl.* 21, 805–813). Similarly, EDTA chelates $Ca^{2+}$, which renders it unavailable to act as co-factor for the activation of Factor C (Dewanjess et al., 1990. *J. Nucl. Med.* 31, 234–245). The endotoxin receptors in both zymogen forms are probably similar to those typical of other LPS-binding proteins (Wright et al., 1986. *J. Exp. Med.* 164, 1876–188; Lei et al., 1988. *J. Immunol.* 141, 996–1011; Tobias et al., 1989. *J. Biol. Chem.* 264, 10867–10871). When either form of Factor C was complexed to LPS strips and incubated with its fluorometric substrate, the Factor C activity remained detectable. This shows that Factor C has an endotoxin-binding site which is unique from its serine protease catalytic site. This endotoxin receptor site is also capable of binding $Me_2SO$, which concomitantly results in its apparent inactivation.

Therefore, using a simple and unique protocol, two forms of Factor C were simultaneously isolated from the Carcinoscorpius amoebocyte lysate. This represents a considerable advancement over earlier methods (Nakamura et al., 1986. *Eur. J. Biochem.* 154, 511–521; Tokunaga et al., 1987. *Eur. J. Biochem.* 167, 405–416) used to isolate the two forms of Factor C from *T. tridentatus*. Furthermore, incorporation of 5% $Me_2SO$ and 1 mM $Na_2EDTA$ not only averted the endotoxin-induced activation of the enzymes, but was instrumental in the isolation, detection, and differentiation of one form of Factor C from the other.

Thus, during the initial stages of amoebocyte lysate preparation, $Me_2SO$ can be used as a reversible inhibitor of endotoxin-induced Factor C activation. For this purpose, $Me_2SO$ can be employed at a concentration of from about 5% to about 30%, v/v. At the final step of lysate preparation, this transient inactivation of Factor C can be reversed by removal of $Me_2SO$. This method will help to overcome the deleterious effects of the ubiquity of endotoxin, and ensures higher quality lysate preparations. Of course, Factor C preparations or solutions of any type can also be protected in this manner as well.

For example, Factor C can be maintained in its zymogen form in any type of preparation, including crude amoebocyte lysates, or by lysing amoebocytes in a solution comprising $Me_2SO$. This solution can further contain a chelating agent such as EDTA, where the lysing solution is pyrogen-free water, or any other solution suitable for lysis, suspension, or storage. $Me_2SO$ can be employed in a concentration of from about 5% to about 30%, v/v, preferably about 5%, v/v, and when present, the chelating agent such as EDTA, $Na_2EDTA$, EGTA, or any other similarly acting chelating agent, can be employed at a concentration of about 1 mM. For long-term storage of such protected lysates before use, the lysates thus prepared can be lyophilized. These steps are useful for long-term storage and maintenance of industrial quantities of amoebocyte lysates prior to and during further treatment of the lysates, or during handling or storage of any Factor C-containing solutions or preparations prior to use to protect Factor C from autoactivation and to maintain it in its zymogen form. $Me_2SO$ and EDTA can subsequently be removed by desalting through Sephadex G-25 or by any other chemical methods of neutralizing $Me_2SO$ and EDTA when the enriched lysate is required, e.g., for LAL assay.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Relevant Publications on *C. rotundicauda* Factor C

1. Ho, B. (1983) "An improved Limulus amoebocyte lysate assay". *Microbios Letts.* 25:81–84.
2. Ho, B. & Ding, J. L. (1985) "Comparison of sensitivity of Tachypleus and Limulus amoebocyte lysate in rapid detection of Gram negative bacteria". *Intl. Congr. on Microbiol. in the 80's*, eds. G. Lim & B. H. Nga. pp. 664–669.
3. Kim, J. C., Ding, J. L. & Ho, B. (1987) "Preparation of active amoebocyte lysate from Tachypleus gigas and *Carcinoscorpius rotundicauda*". Abstract in *Proc. Ann. Sci. Meeting of the Singapore Soc. Microbiol.* 10–11 Jan. 1987, ed. Y. C. Chan, p. 21.
4. Ding, J. L., Kim, J. C. & Ho, B. (1988) "Pokeweed mitogen stimulates DNA synthesis in cultured amoebocytes of *Carcinoscorpius rotundicauda*." *Cytobios* 55:147–154.
5. Kim, J. C., Ding, J. L. & Ho, B. (1988) "Endotoxin activation of clotting proteins from *Carcinoscorpius rotundicauda* amoebocyte lysate." In: *Advances in Biochem. & Biotechnol. in Asia and Oceania*, eds. A. Sipat, K. Ampon, R. Perumal, S. Aziz, and V. Thambyrajah, Malaysia, p. F1.
6. Navas III, M. A. A., Ding, J. L. & Ho, B. (1989) "Purification and characterisation of Factor C and pro-clotting enzyme from amoebocyte lysate of *Carcinoscorpius rotundicauda*". Abstract in *Proc. 5th FAOB Congr.*, 13–18 Aug. 1989, Seoul, S. Korea. p. 199.
7. Yeo, S. A., Ho, B. & Ding, J. L. (1989) "Preservation of Factor C activity and removal of its inhibitory factor from *Carcinoscorpius rotundicauda*." Abstract in *Intl. Symp. New Frontiers Food & Med. Microbiol.*, Singapore. p. 79.
8. Navas III, M. A. A., Ding, J. L. & Ho, B. (1990) "Inactivation of Factor C by dimethyl sulfoxide inhibits coagulation of the Carcinoscorpius amoebocyte lysate" *Biochem. Intl.*, Academic Press, Australia. 21(5):805–813.
9. Ho, B., Kim. J. C. & Ding J. L. (1993) "Electrophoretic analysis of endotoxin-activated gelation reaction of *Carcinoscorpius rotundicauda* amoebocyte lysate" *Biochem. & Mol. Biol. Intl.*, Acad. Press, Australia. 29(4):687–694.
10. Ding, J. L., Navas, M. A. A. & Ho, B. (1993) "Two forms of Factor C from the amoebocytes of *Carcinoscorpius rotundicauda*: Purification and characterisation" *Biochim. et Biophys. Acta* 1202: 149–156.
11. Ding, J. L., Sababathy, Tr.K. & Ho, B. (1993) "Morphological changes in *Carcinoscorpius rotundicauda* amoebocytes and *E. coli* during their interaction" *Cytobios* 75:21–32.

We claim:

1. An isolated DNA molecule encoding a protein having an amino acid sequence selected from the group consisting of SEQ ID NO:2 and SEQ ID NO:4.

2. The DNA molecule of claim 3, having a nucleotide sequence selected from the group consisting of SEQ ID NO:1 and SEQ ID NO:3.

3. The DNA molecule of claim 2, wherein said DNA molecule has the nucleotide sequence of SEQ ID NO:1, wherein nucleotides 1 to 568 have been deleted.

4. A recombinant vector comprising DNA encoding an amino acid sequence selected from the group consisting of SEQ ID NO:2 and SEQ ID NO:4.

5. The recombinant vector of claim 4, wherein said DNA has a nucleotide sequence selected from the group consisting of SEQ ID NO:1 and SEQ ID NO:3.

6. A host cell transformed with said recombinant vector of claim 5.

7. The host cell of claim 6, wherein said host cell is selected from the group consisting of *E. coli*, a mammalian cell, an insect cell, and a yeast.

8. A method for producing a protein having the enzymatic activity of Factor C protein in assays for Gram negative bacterial endotoxin, comprising culturing said host cell according to claim 6 under conditions such that said DNA molecule is expressed, and recovering said protein.

9. The recombinant vector of claim 4, wherein the vector portion is a member selected from the group consisting of λgt 22, pGEM 11Zf(+), pGEMEX-1, pET 3b, YEpsec 1, pEMBLyex 4, pIC 9 and pHIL D2.

10. A host cell transformed with said recombinant vector of claim 4.

11. The host cell of claim 10, wherein said host cell is selected from the group consisting of *E. coli*, a mammalian cell, an insect cell, and a yeast.

12. A method of producing a protein having the same enzymatic activity as Factor C protein in assays for Gram negative bacterial endotoxin, comprising culturing said host cell of claim 10 under conditions in which said DNA molecule is expressed, and recovering said protein.

* * * * *

UNITED STATES PATENT AND TRADEMARK OFFICE
CERTIFICATE OF CORRECTION

PATENT NO. : 5,716,834
DATED : Feb. 10, 1998
INVENTOR(S) : DING et al.

It is certified that error appears in the above-indentified patent and that said Letters Patent is hereby corrected as shown below:

On the Cover Page
    [54] In the Title
        change "CDNA" to --cDNA--

Column 1, line 1
    change "CDNA" to --cDNA--

Column 2, line 51
    change "pIC" to --pPIC--

Column 4, line 20
    change "sublconed" to --subcloned--

Column 8, line 13
    Change "Na2EDTA" to --$Na_2EDTA$--

UNITED STATES PATENT AND TRADEMARK OFFICE
CERTIFICATE OF CORRECTION

PATENT NO. : 5,716,834
DATED : Feb. 10, 1998
INVENTOR(S) : DING et al.

It is certified that error appears in the above-indentified patent and that said Letters Patent is hereby corrected as shown below:

Column 13, line 27
    change "C. rotundicauda" to
        --*C. rotundicauda*--

Column 54, line 4 of claim 9
    change "pIC" to --pPIC--

Signed and Sealed this

Twenty-second Day of September, 1998

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,716,834
DATED : February 10, 1998
INVENTOR(S) : DING et al.

It is certified that error appears in the above-identified patent and that said Letters Patent is hereby corrected as shown below:

Column 53:

Claim 2, change "claim 3" to --claim 1--

Signed and Sealed this

Fourth Day of January, 2000

Attest:

Attesting Officer

Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 4182 base pairs
    ( B ) TYPE: nucleic acid
    ( C ) STRANDEDNESS: single
    ( D ) TOPOLOGY: both ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Carcinoscorpius rotundicauda ( i x ) FEATURE:
    ( A ) NAME/KEY: CDS
    ( B ) LOCATION: 569..3817

( x i ) SEQUENCE DESCRIPTION: SEQ ID NO:1:

```
GTATTTAATG TCTCAACGGT AAAGGTTTCA TTGTAGCTAA TATTTAACTT CCTCCCTGTG        60

CCCCAAATCG CGAGTATGAC GTCAGTTAAG ACTTCGTATT TTAAGAGTTA AACACGAGCC       120

TTAAAGAGCG ATATTTTTT TGTTAAACAC TTCCAACTTA ATACAATTGG CAAACTTTCA        180

AAAATAAAGT GGAAAAGGAG GTAAAAAAGA TGAAAAAAAT TCGCATACAA TAGAATACAA       240

TAAAATGTGT TGTCTTTACT GTCAACACTT ACTGTTCGTT CGGTCACAGC TGTGAATCGG       300

GGTGACTTTA TGTTTGTAGT GGTCTTAAAA ACGGGTACTT GGTTGTTTTG AAAATTTTAA       360

AACCTACATA TGATTCTCCT AAAATTTGT TTATAAATTA GCACCATTTG CGACCTAAAT        420

CTTTTTTGTA GTCTTAAGTT TAGTTGACAT AAAAACAAAA TTTGTAACAA CACACGGTAT       480

AAACTAAATA GCTTCAGATG GGTCGTATGA CAAGGAAACT TTTAAATAAT TATGAAAGTT       540

TTTTTAAAAT TTGACTAAGG TTTAGATT ATG TGG GTG ACA TGC TTC GAC ACG         592
                                Met Trp Val Thr Cys Phe Asp Thr
                                  1               5

TTT CTT TTT GTT TGT GAA AGT TCA GTT TTC TGT TTG TTG TGT GTG TGG         640
Phe Leu Phe Val Cys Glu Ser Ser Val Phe Cys Leu Leu Cys Val Trp
     10              15                  20

AGG TTT GGT TTC TGT AGG TGG CGT GTT TTC TAC AGT TTT CCA TTC GTT         688
Arg Phe Gly Phe Cys Arg Trp Arg Val Phe Tyr Ser Phe Pro Phe Val
 25                  30                  35              40

AAG TCA ACA GTT GTT TTA TTA CAG TGT TAC CAT TAC TCT CTC CAC AAT         736
Lys Ser Thr Val Val Leu Leu Gln Cys Tyr His Tyr Ser Leu His Asn
                 45                  50                  55

ACC TCA AAG TTC TAC TCT GTG AAT CCT GAC AAG CCA GAG TAC ATT CTT         784
Thr Ser Lys Phe Tyr Ser Val Asn Pro Asp Lys Pro Glu Tyr Ile Leu
             60                  65                  70

TCA GGT TTA GTT CTA GGG CTA CTA GCC CAA AAA ATG CGC CCA GTT CAG         832
Ser Gly Leu Val Leu Gly Leu Leu Ala Gln Lys Met Arg Pro Val Gln
         75                  80                  85

TCC AAA GGA GTA GAT CTA GGC TTG TGT GAT GAA ACG AGG TTC GAG TGT         880
Ser Lys Gly Val Asp Leu Gly Leu Cys Asp Glu Thr Arg Phe Glu Cys
     90                  95                 100

AAG TGT GGC GAT CCA GGC TAT GTG TTC AAC ATT CCA GTG AAA CAA TGT         928
Lys Cys Gly Asp Pro Gly Tyr Val Phe Asn Ile Pro Val Lys Gln Cys
105                 110                 115                 120
```

| | | | | | | | | | | | | | | | | |
|---|---|---|---|---|---|---|---|---|---|---|---|---|---|---|---|---|
| ACA | TAC | TTT | TAT | CGA | TGG | AGG | CCG | TAT | TGT | AAA | CCA | TGT | GAT | GAC | CTG | 976 |
| Thr | Tyr | Phe | Tyr | Arg | Trp | Arg | Pro | Tyr | Cys | Lys | Pro | Cys | Asp | Asp | Leu | |
| | | | 125 | | | | | 130 | | | | | 135 | | | |
| GAG | GCT | AAG | GAT | ATT | TGT | CCA | AAG | TAC | AAA | CGA | TGT | CAA | GAG | TGT | AAG | 1024 |
| Glu | Ala | Lys | Asp | Ile | Cys | Pro | Lys | Tyr | Lys | Arg | Cys | Gln | Glu | Cys | Lys | |
| | | 140 | | | | | 145 | | | | | 150 | | | | |
| GCT | GGT | CTT | GAT | AGT | TGT | GTT | ACT | TGT | CCA | CCT | AAC | AAA | TAT | GGT | ACT | 1072 |
| Ala | Gly | Leu | Asp | Ser | Cys | Val | Thr | Cys | Pro | Pro | Asn | Lys | Tyr | Gly | Thr | |
| | | 155 | | | | | 160 | | | | | 165 | | | | |
| TGG | TGT | AGC | GGT | GAA | TGT | CAG | TGT | AAG | AAT | GGA | GGT | ATC | TGT | GAC | CAG | 1120 |
| Trp | Cys | Ser | Gly | Glu | Cys | Gln | Cys | Lys | Asn | Gly | Gly | Ile | Cys | Asp | Gln | |
| | | 170 | | | | 175 | | | | | 180 | | | | | |
| AGG | ACA | GGA | GCT | TGT | GCA | TGT | CGT | GAC | AGA | TAT | GAA | GGG | GTG | CAC | TGT | 1168 |
| Arg | Thr | Gly | Ala | Cys | Ala | Cys | Arg | Asp | Arg | Tyr | Glu | Gly | Val | His | Cys | |
| 185 | | | | | 190 | | | | | 195 | | | | | 200 | |
| GAA | ATT | CTC | AAA | GGT | TGT | CCT | CTT | CTT | CCA | TCG | GAT | TCT | CAG | GTT | CAG | 1216 |
| Glu | Ile | Leu | Lys | Gly | Cys | Pro | Leu | Leu | Pro | Ser | Asp | Ser | Gln | Val | Gln | |
| | | | | 205 | | | | | 210 | | | | | 215 | | |
| GAA | GTC | AGA | AAT | CCA | CCA | GAT | AAT | CCC | CAA | ACT | ATT | GAC | TAC | AGC | TGT | 1264 |
| Glu | Val | Arg | Asn | Pro | Pro | Asp | Asn | Pro | Gln | Thr | Ile | Asp | Tyr | Ser | Cys | |
| | | | 220 | | | | | 225 | | | | | 230 | | | |
| TCA | CCA | GGG | TTC | AAG | CTT | AAG | GGT | ATG | GCA | CGA | ATT | AGC | TGT | CTC | CCA | 1312 |
| Ser | Pro | Gly | Phe | Lys | Leu | Lys | Gly | Met | Ala | Arg | Ile | Ser | Cys | Leu | Pro | |
| | | 235 | | | | | 240 | | | | | 245 | | | | |
| AAT | GGA | CAG | TGG | AGT | AAC | TTT | CCA | CCC | AAA | TGT | ATT | CGA | GAA | TGT | GCC | 1360 |
| Asn | Gly | Gln | Trp | Ser | Asn | Phe | Pro | Pro | Lys | Cys | Ile | Arg | Glu | Cys | Ala | |
| | 250 | | | | | 255 | | | | | 260 | | | | | |
| ATG | GTT | TCA | TCT | CCA | GAA | CAT | GGG | AAA | GTG | AAT | GCT | CTT | AGT | GGT | GAT | 1408 |
| Met | Val | Ser | Ser | Pro | Glu | His | Gly | Lys | Val | Asn | Ala | Leu | Ser | Gly | Asp | |
| 265 | | | | | 270 | | | | | 275 | | | | | 280 | |
| ATG | ATA | GAA | GGG | GCT | ACT | TTA | CGG | TTC | TCA | TGT | GAT | AGT | CCC | TAC | TAC | 1456 |
| Met | Ile | Glu | Gly | Ala | Thr | Leu | Arg | Phe | Ser | Cys | Asp | Ser | Pro | Tyr | Tyr | |
| | | | | 285 | | | | | 290 | | | | | 295 | | |
| TTG | ATT | GGT | CAA | GAA | ACA | TTA | ACC | TGT | CAG | GGT | AAT | GGT | CAG | TGG | AAT | 1504 |
| Leu | Ile | Gly | Gln | Glu | Thr | Leu | Thr | Cys | Gln | Gly | Asn | Gly | Gln | Trp | Asn | |
| | | | 300 | | | | | 305 | | | | | 310 | | | |
| GGA | CAG | ATA | CCA | CAA | TGT | AAG | AAC | TTA | GTC | TTC | TGT | CCT | GAC | CTG | GAT | 1552 |
| Gly | Gln | Ile | Pro | Gln | Cys | Lys | Asn | Leu | Val | Phe | Cys | Pro | Asp | Leu | Asp | |
| | | 315 | | | | | 320 | | | | | 325 | | | | |
| CCT | GTA | AAC | CAT | GCT | GAA | CAC | AAG | GTT | AAA | ATT | GGT | GTG | GAA | CAA | AAA | 1600 |
| Pro | Val | Asn | His | Ala | Glu | His | Lys | Val | Lys | Ile | Gly | Val | Glu | Gln | Lys | |
| | 330 | | | | | 335 | | | | | 340 | | | | | |
| TAT | GGT | CAG | TTT | CCT | CAA | GGC | ACT | GAA | GTG | ACC | TAT | ACG | TGT | TCG | GGT | 1648 |
| Tyr | Gly | Gln | Phe | Pro | Gln | Gly | Thr | Glu | Val | Thr | Tyr | Thr | Cys | Ser | Gly | |
| 345 | | | | | 350 | | | | | 355 | | | | | 360 | |
| AAC | TAC | TTC | TTG | ATG | GGT | TTT | GAC | ACC | TTA | AAA | TGT | AAC | CCT | GAT | GGG | 1696 |
| Asn | Tyr | Phe | Leu | Met | Gly | Phe | Asp | Thr | Leu | Lys | Cys | Asn | Pro | Asp | Gly | |
| | | | | 365 | | | | | 370 | | | | | 375 | | |
| TCT | TGG | TCA | GGA | TCA | CAG | CCA | TCC | TGT | GTT | AAA | GTG | GCA | GAC | AGA | GAG | 1744 |
| Ser | Trp | Ser | Gly | Ser | Gln | Pro | Ser | Cys | Val | Lys | Val | Ala | Asp | Arg | Glu | |
| | | | 380 | | | | | 385 | | | | | 390 | | | |
| GTC | GAC | TGT | GAC | AGT | AAA | GCT | GTA | GAC | TTC | TTG | GAT | GAT | GTT | GGT | GAA | 1792 |
| Val | Asp | Cys | Asp | Ser | Lys | Ala | Val | Asp | Phe | Leu | Asp | Asp | Val | Gly | Glu | |
| | | 395 | | | | | 400 | | | | | 405 | | | | |
| CCT | GTC | AGG | ATC | CAC | TGT | CCT | GCT | GGC | TGT | TCT | TTG | ACA | GCT | GGT | ACT | 1840 |
| Pro | Val | Arg | Ile | His | Cys | Pro | Ala | Gly | Cys | Ser | Leu | Thr | Ala | Gly | Thr | |
| | 410 | | | | | 415 | | | | | 420 | | | | | |
| GTG | TGG | GGT | ACA | GCC | ATA | TAC | CAT | GAA | CTT | TCC | TCA | GTG | TGT | CGT | GCA | 1888 |
| Val | Trp | Gly | Thr | Ala | Ile | Tyr | His | Glu | Leu | Ser | Ser | Val | Cys | Arg | Ala | |
| 425 | | | | | 430 | | | | | 435 | | | | | 440 | |

| | | | | | | | | | | | | | | | | |
|---|---|---|---|---|---|---|---|---|---|---|---|---|---|---|---|---|
| GCC | ATC | CAT | GCT | GGC | AAG | CTT | CCA | AAC | TCT | GGA | GGA | GCG | GTG | CAT | GTT | 1936 |
| Ala | Ile | His | Ala | Gly | Lys | Leu | Pro | Asn | Ser | Gly | Gly | Ala | Val | His | Val | |
| | | | | 445 | | | | | 450 | | | | | 455 | | |
| GTG | AAC | AAT | GGC | CCC | TAC | TCG | GAC | TTT | CTG | GGT | AGT | GAC | CTG | AAT | GGG | 1984 |
| Val | Asn | Asn | Gly | Pro | Tyr | Ser | Asp | Phe | Leu | Gly | Ser | Asp | Leu | Asn | Gly | |
| | | | 460 | | | | | 465 | | | | | 470 | | | |
| ATA | AAA | TCC | GAA | GAG | TTG | AAG | TCT | CTT | GCC | CGG | AGT | TTC | CGA | TTC | GAT | 2032 |
| Ile | Lys | Ser | Glu | Glu | Leu | Lys | Ser | Leu | Ala | Arg | Ser | Phe | Arg | Phe | Asp | |
| | | 475 | | | | | 480 | | | | | 485 | | | | |
| TAT | GTC | AGT | TCC | TCC | ACA | GCA | GGT | AAA | TCA | GGA | TGT | CCT | GAT | GGA | TGG | 2080 |
| Tyr | Val | Ser | Ser | Ser | Thr | Ala | Gly | Lys | Ser | Gly | Cys | Pro | Asp | Gly | Trp | |
| | 490 | | | | | 495 | | | | | 500 | | | | | |
| TTT | GAG | GTA | GAC | GAG | AAC | TGT | GTG | TAC | GTT | ACA | TCA | AAA | CAG | AGA | GCC | 2128 |
| Phe | Glu | Val | Asp | Glu | Asn | Cys | Val | Tyr | Val | Thr | Ser | Lys | Gln | Arg | Ala | |
| 505 | | | | | 510 | | | | | 515 | | | | | 520 | |
| TGG | GAA | AGA | GCT | CAA | GGT | GTG | TGT | ACC | AAT | ATG | GCT | GCT | CGT | CTT | GCT | 2176 |
| Trp | Glu | Arg | Ala | Gln | Gly | Val | Cys | Thr | Asn | Met | Ala | Ala | Arg | Leu | Ala | |
| | | | | 525 | | | | | 530 | | | | | 535 | | |
| GTG | CTG | GAC | AAA | GAT | GTA | ATT | CCA | AAT | TCA | TTG | ACT | GAG | ACT | CTA | CGA | 2224 |
| Val | Leu | Asp | Lys | Asp | Val | Ile | Pro | Asn | Ser | Leu | Thr | Glu | Thr | Leu | Arg | |
| | | | 540 | | | | | 545 | | | | | 550 | | | |
| GGG | AAA | GGG | TTA | ACA | ACC | ACG | TGG | ATA | GGA | TTG | CAC | AGA | CTA | GAT | GCT | 2272 |
| Gly | Lys | Gly | Leu | Thr | Thr | Thr | Trp | Ile | Gly | Leu | His | Arg | Leu | Asp | Ala | |
| | | 555 | | | | | 560 | | | | | 565 | | | | |
| GAG | AAG | CCC | TTT | ATT | TGG | GAG | TTA | ATG | GAT | CGT | AGT | AAT | GTG | GTT | CTG | 2320 |
| Glu | Lys | Pro | Phe | Ile | Trp | Glu | Leu | Met | Asp | Arg | Ser | Asn | Val | Val | Leu | |
| | 570 | | | | | 575 | | | | | 580 | | | | | |
| AAT | GAT | AAC | CTA | ACA | TTC | TGG | GCC | TCT | GGC | GAA | CCT | GGA | AAT | GAA | ACT | 2368 |
| Asn | Asp | Asn | Leu | Thr | Phe | Trp | Ala | Ser | Gly | Glu | Pro | Gly | Asn | Glu | Thr | |
| 585 | | | | | 590 | | | | | 595 | | | | | 600 | |
| AAC | TGT | GTA | TAT | ATG | GAC | ATC | CAA | GAT | CAG | TTG | CAG | TCT | GTG | TGG | AAA | 2416 |
| Asn | Cys | Val | Tyr | Met | Asp | Ile | Gln | Asp | Gln | Leu | Gln | Ser | Val | Trp | Lys | |
| | | | | 605 | | | | | 610 | | | | | 615 | | |
| ACC | AAG | TCA | TGT | TTT | CAG | CCC | TCA | AGT | TTT | GCT | TGC | ATG | ATG | GAT | CTG | 2464 |
| Thr | Lys | Ser | Cys | Phe | Gln | Pro | Ser | Ser | Phe | Ala | Cys | Met | Met | Asp | Leu | |
| | | | 620 | | | | | 625 | | | | | 630 | | | |
| TCA | GAC | AGA | AAT | AAA | GCC | AAA | TGC | GAT | GAT | CCT | GGA | TCA | CTG | GAA | AAT | 2512 |
| Ser | Asp | Arg | Asn | Lys | Ala | Lys | Cys | Asp | Asp | Pro | Gly | Ser | Leu | Glu | Asn | |
| | | 635 | | | | | 640 | | | | | 645 | | | | |
| GGA | CAC | GCC | ACA | CTT | CAT | GGA | CAA | AGT | ATT | GAT | GGG | TTC | TAT | GCT | GGT | 2560 |
| Gly | His | Ala | Thr | Leu | His | Gly | Gln | Ser | Ile | Asp | Gly | Phe | Tyr | Ala | Gly | |
| | 650 | | | | | 655 | | | | | 660 | | | | | |
| TCT | TCT | ATA | AGG | TAC | AGC | TGT | GAG | GTT | CTC | CAC | TAC | CTC | AGT | GGA | ACT | 2608 |
| Ser | Ser | Ile | Arg | Tyr | Ser | Cys | Glu | Val | Leu | His | Tyr | Leu | Ser | Gly | Thr | |
| 665 | | | | | 670 | | | | | 675 | | | | | 680 | |
| GAA | ACC | GTA | ACT | TGT | ACA | ACA | AAT | GGC | ACA | TGG | AGT | GCT | CCT | AAA | CCT | 2656 |
| Glu | Thr | Val | Thr | Cys | Thr | Thr | Asn | Gly | Thr | Trp | Ser | Ala | Pro | Lys | Pro | |
| | | | | 685 | | | | | 690 | | | | | 695 | | |
| CGA | TGT | ATC | AAA | GTC | ATC | ACC | TGC | CAA | AAC | CCC | CCT | GTA | CCA | TCA | TAT | 2704 |
| Arg | Cys | Ile | Lys | Val | Ile | Thr | Cys | Gln | Asn | Pro | Pro | Val | Pro | Ser | Tyr | |
| | | | 700 | | | | | 705 | | | | | 710 | | | |
| GGT | TCT | GTG | GAA | ATC | AAA | CCC | CCA | AGT | CGG | ACA | AAC | TCG | ATA | AGT | CGT | 2752 |
| Gly | Ser | Val | Glu | Ile | Lys | Pro | Pro | Ser | Arg | Thr | Asn | Ser | Ile | Ser | Arg | |
| | | 715 | | | | | 720 | | | | | 725 | | | | |
| GTT | GGG | TCA | CCT | TTC | TTG | AGG | TTG | CCA | CGG | TTA | CCC | CTC | CCA | TTA | GCC | 2800 |
| Val | Gly | Ser | Pro | Phe | Leu | Arg | Leu | Pro | Arg | Leu | Pro | Leu | Pro | Leu | Ala | |
| | 730 | | | | | 735 | | | | | 740 | | | | | |
| AGA | GCA | GCC | AAA | CCT | CCT | CCA | AAA | CCT | AGA | TCC | TCA | CAA | CCC | TCT | ACT | 2848 |
| Arg | Ala | Ala | Lys | Pro | Pro | Pro | Lys | Pro | Arg | Ser | Ser | Gln | Pro | Ser | Thr | |
| 745 | | | | | 750 | | | | | 755 | | | | | 760 | |

```
GTG GAC TTG GCT TCT AAA GTT AAA CTA CCT GAA GGT CAT TAC CGG GTA        2896
Val Asp Leu Ala Ser Lys Val Lys Leu Pro Glu Gly His Tyr Arg Val
            765             770                 775

GGG TCT CGA GCC ATT TAC ACG TGC GAG TCG AGA TAC TAC GAA CTA CTT        2944
Gly Ser Arg Ala Ile Tyr Thr Cys Glu Ser Arg Tyr Tyr Glu Leu Leu
            780             785                 790

GGA TCT CAA GGC AGA AGA TGT GAC TCT AAT GGA AAC TGG AGT GGT CGG        2992
Gly Ser Gln Gly Arg Arg Cys Asp Ser Asn Gly Asn Trp Ser Gly Arg
            795             800                 805

CCA GCG AGC TGT ATT CCA GTT TGT GGA CGG TCA GAC TCT CCT CGT TCT        3040
Pro Ala Ser Cys Ile Pro Val Cys Gly Arg Ser Asp Ser Pro Arg Ser
            810             815                 820

CCT TTT ATC TGG AAT GGG AAT TCT ACA GAA ATA GGT CAG TGG CCG TGG        3088
Pro Phe Ile Trp Asn Gly Asn Ser Thr Glu Ile Gly Gln Trp Pro Trp
825             830             835                 840

CAG GCA GGA ATC TCT AGA TGG CTT GCA GAC CAC AAT ATG TGG TTT CTC        3136
Gln Ala Gly Ile Ser Arg Trp Leu Ala Asp His Asn Met Trp Phe Leu
                845             850                 855

CAG TGT GGA GGA TCT CTA TTG AAT GAG AAA TGG ATC GTC ACT GCT GCC        3184
Gln Cys Gly Gly Ser Leu Leu Asn Glu Lys Trp Ile Val Thr Ala Ala
            860             865                 870

CAC TGT GTC ACC TAC TCT GCT ACT GCT GAG ATT ATT GAC CCC AAT CAG        3232
His Cys Val Thr Tyr Ser Ala Thr Ala Glu Ile Ile Asp Pro Asn Gln
            875             880                 885

TTT AAA ATG TAT CTG GGC AAG TAC TAC CGT GAT GAC AGT AGA GAC GAT        3280
Phe Lys Met Tyr Leu Gly Lys Tyr Tyr Arg Asp Asp Ser Arg Asp Asp
            890             895                 900

GAC TAT GTA CAA GTA AGA GAG GCT CTT GAG ATC CAC GTG AAT CCT AAC        3328
Asp Tyr Val Gln Val Arg Glu Ala Leu Glu Ile His Val Asn Pro Asn
905             910             915                 920

TAC GAC CCC GGC AAT CTC AAC TTT GAC ATA GCC CTA ATT CAA CTG AAA        3376
Tyr Asp Pro Gly Asn Leu Asn Phe Asp Ile Ala Leu Ile Gln Leu Lys
                925             930                 935

ACT CCT GTT ACT TTG ACA ACA CGA GTC CAA CCA ATC TGT CTG CCT ACT        3424
Thr Pro Val Thr Leu Thr Thr Arg Val Gln Pro Ile Cys Leu Pro Thr
            940             945                 950

GAC ATC ACA ACA AGA GAA CAC TTG AAG GAG GGA ACA TTA GCA GTG GTG        3472
Asp Ile Thr Thr Arg Glu His Leu Lys Glu Gly Thr Leu Ala Val Val
            955             960                 965

ACA GGT TGG GGT TTG AAT GAA AAC AAC ACC TAT TCA GAG ACG ATT CAA        3520
Thr Gly Trp Gly Leu Asn Glu Asn Asn Thr Tyr Ser Glu Thr Ile Gln
            970             975                 980

CAA GCT GTG CTA CCT GTT GTT GCA GCC AGC ACC TGT GAA GAG GGG TAC        3568
Gln Ala Val Leu Pro Val Val Ala Ala Ser Thr Cys Glu Glu Gly Tyr
985             990             995                 1000

AAG GAA GCA GAC TTA CCA CTG ACA GTA ACA GAG AAC ATG TTC TGT GCA        3616
Lys Glu Ala Asp Leu Pro Leu Thr Val Thr Glu Asn Met Phe Cys Ala
            1005            1010                1015

GGT TAC AAG AAG GGA CGT TAT GAT GCC TGC AGT GGG GAC AGT GGA GGA        3664
Gly Tyr Lys Lys Gly Arg Tyr Asp Ala Cys Ser Gly Asp Ser Gly Gly
            1020            1025                1030

CCT TTA GTG TTT GCT GAT GAT TCC CGT ACC GAA AGG CGG TGG GTC TTG        3712
Pro Leu Val Phe Ala Asp Asp Ser Arg Thr Glu Arg Arg Trp Val Leu
            1035            1040                1045

GAA GGG ATT GTC AGC TGG GGC AGT CCC AGT GGA TGT GGC AAG GCG AAC        3760
Glu Gly Ile Val Ser Trp Gly Ser Pro Ser Gly Cys Gly Lys Ala Asn
            1050            1055                1060

CAG TAC GGG GGC TTC ACT AAA GTT AAC GTT TTC CTG TCA TGG ATT AGG        3808
Gln Tyr Gly Gly Phe Thr Lys Val Asn Val Phe Leu Ser Trp Ile Arg
            1065            1070                1075            1080
```

```
CAG TTC ATT TGAAACTGAT CTAAATATTT TAAGCATGGT TATAAACGTC         3857
Gln Phe Ile

TTGTTCCTAT TATTGCTTTA CTGGTTTAAC CCATAAGAAG GTTAACGGGG TAAGGCACAA  3917

GGATCATTGT TTCTGTTTGT TTTTACAAAT GGTTCTTTTA GTCAGTGAAT GAGAATAGTA  3977

TCCATTGGAG ACTGTTACCT TTTATTCTAC CTTTTTATAT TACTATGCAA GTATTTGGGA  4037

TATCTTCTAC ACATGAAAAT TCTGTCATTT TACCATAAAT TTGGTTTCTG GTGTGTGTGT  4097

TAAGTCCACC ACTAGAGAAC GATGTAATTT TCAATAGTAC ATGAAATAAA TATAGAACAA  4157

ATCTATTATA AAAAAAAAAA AAAAA                                       4182
```

( 2 ) INFORMATION FOR SEQ ID NO:2:

( i ) SEQUENCE CHARACTERISTICS:
      ( A ) LENGTH: 1083 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met Trp Val Thr Cys Phe Asp Thr Phe Leu Phe Val Cys Glu Ser Ser
 1               5                  10                  15

Val Phe Cys Leu Leu Cys Val Trp Arg Phe Gly Phe Cys Arg Trp Arg
                20                  25                  30

Val Phe Tyr Ser Phe Pro Phe Val Lys Ser Thr Val Val Leu Leu Gln
            35                  40                  45

Cys Tyr His Tyr Ser Leu His Asn Thr Ser Lys Phe Tyr Ser Val Asn
        50                  55                  60

Pro Asp Lys Pro Glu Tyr Ile Leu Ser Gly Leu Val Leu Gly Leu Leu
65                  70                  75                  80

Ala Gln Lys Met Arg Pro Val Gln Ser Lys Gly Val Asp Leu Gly Leu
                85                  90                  95

Cys Asp Glu Thr Arg Phe Glu Cys Lys Cys Gly Asp Pro Gly Tyr Val
            100                 105                 110

Phe Asn Ile Pro Val Lys Gln Cys Thr Tyr Phe Tyr Arg Trp Arg Pro
        115                 120                 125

Tyr Cys Lys Pro Cys Asp Asp Leu Glu Ala Lys Asp Ile Cys Pro Lys
    130                 135                 140

Tyr Lys Arg Cys Gln Glu Cys Lys Ala Gly Leu Asp Ser Cys Val Thr
145                 150                 155                 160

Cys Pro Pro Asn Lys Tyr Gly Thr Trp Cys Ser Gly Glu Cys Gln Cys
                165                 170                 175

Lys Asn Gly Gly Ile Cys Asp Gln Arg Thr Gly Ala Cys Ala Cys Arg
            180                 185                 190

Asp Arg Tyr Glu Gly Val His Cys Glu Ile Leu Lys Gly Cys Pro Leu
        195                 200                 205

Leu Pro Ser Asp Ser Gln Val Gln Glu Val Arg Asn Pro Pro Asp Asn
    210                 215                 220

Pro Gln Thr Ile Asp Tyr Ser Cys Ser Pro Gly Phe Lys Leu Lys Gly
225                 230                 235                 240

Met Ala Arg Ile Ser Cys Leu Pro Asn Gly Gln Trp Ser Asn Phe Pro
                245                 250                 255

Pro Lys Cys Ile Arg Glu Cys Ala Met Val Ser Ser Pro Glu His Gly
            260                 265                 270

Lys Val Asn Ala Leu Ser Gly Asp Met Ile Glu Gly Ala Thr Leu Arg
```

|     |     |     |     | 275 |     |     |     |     |     | 280 |     |     |     |     |     | 285 |     |     |
|-----|-----|-----|-----|-----|-----|-----|-----|-----|-----|-----|-----|-----|-----|-----|-----|-----|-----|-----|

Phe Ser Cys Asp Ser Pro Tyr Tyr Leu Ile Gly Gln Glu Thr Leu Thr
290                     295                     300

Cys Gln Gly Asn Gly Gln Trp Asn Gly Gln Ile Pro Gln Cys Lys Asn
305                 310                     315                 320

Leu Val Phe Cys Pro Asp Leu Asp Pro Val Asn His Ala Glu His Lys
                325                     330                     335

Val Lys Ile Gly Val Glu Gln Lys Tyr Gly Gln Phe Pro Gln Gly Thr
            340                     345                     350

Glu Val Thr Tyr Thr Cys Ser Gly Asn Tyr Phe Leu Met Gly Phe Asp
        355                     360                     365

Thr Leu Lys Cys Asn Pro Asp Gly Ser Trp Ser Gly Ser Gln Pro Ser
    370                     375                     380

Cys Val Lys Val Ala Asp Arg Glu Val Asp Cys Asp Ser Lys Ala Val
385                     390                     395                 400

Asp Phe Leu Asp Asp Val Gly Glu Pro Val Arg Ile His Cys Pro Ala
                405                     410                     415

Gly Cys Ser Leu Thr Ala Gly Thr Val Trp Gly Thr Ala Ile Tyr His
            420                     425                     430

Glu Leu Ser Ser Val Cys Arg Ala Ala Ile His Ala Gly Lys Leu Pro
        435                     440                     445

Asn Ser Gly Gly Ala Val His Val Val Asn Asn Gly Pro Tyr Ser Asp
    450                     455                     460

Phe Leu Gly Ser Asp Leu Asn Gly Ile Lys Ser Glu Glu Leu Lys Ser
465                     470                     475                 480

Leu Ala Arg Ser Phe Arg Phe Asp Tyr Val Ser Ser Ser Thr Ala Gly
                485                     490                     495

Lys Ser Gly Cys Pro Asp Gly Trp Phe Glu Val Asp Glu Asn Cys Val
            500                     505                     510

Tyr Val Thr Ser Lys Gln Arg Ala Trp Glu Arg Ala Gln Gly Val Cys
        515                     520                     525

Thr Asn Met Ala Ala Arg Leu Ala Val Leu Asp Lys Asp Val Ile Pro
    530                     535                     540

Asn Ser Leu Thr Glu Thr Leu Arg Gly Lys Gly Leu Thr Thr Thr Trp
545                     550                     555                 560

Ile Gly Leu His Arg Leu Asp Ala Glu Lys Pro Phe Ile Trp Glu Leu
                565                     570                     575

Met Asp Arg Ser Asn Val Val Leu Asn Asp Asn Leu Thr Phe Trp Ala
            580                     585                     590

Ser Gly Glu Pro Gly Asn Glu Thr Asn Cys Val Tyr Met Asp Ile Gln
        595                     600                     605

Asp Gln Leu Gln Ser Val Trp Lys Thr Lys Ser Cys Phe Gln Pro Ser
    610                     615                     620

Ser Phe Ala Cys Met Met Asp Leu Ser Asp Arg Asn Lys Ala Lys Cys
625                     630                     635                 640

Asp Asp Pro Gly Ser Leu Glu Asn Gly His Ala Thr Leu His Gly Gln
                645                     650                     655

Ser Ile Asp Gly Phe Tyr Ala Gly Ser Ser Ile Arg Tyr Ser Cys Glu
            660                     665                     670

Val Leu His Tyr Leu Ser Gly Thr Glu Thr Val Thr Cys Thr Thr Asn
        675                     680                     685

Gly Thr Trp Ser Ala Pro Lys Pro Arg Cys Ile Lys Val Ile Thr Cys
    690                     695                     700

-continued

```
Gln  Asn  Pro  Pro  Val  Pro  Ser  Tyr  Gly  Ser  Val  Glu  Ile  Lys  Pro  Pro
705                      710                     715                     720

Ser  Arg  Thr  Asn  Ser  Ile  Ser  Arg  Val  Gly  Ser  Pro  Phe  Leu  Arg  Leu
               725                      730                          735

Pro  Arg  Leu  Pro  Leu  Pro  Leu  Ala  Arg  Ala  Ala  Lys  Pro  Pro  Pro  Lys
               740                 745                     750

Pro  Arg  Ser  Ser  Gln  Pro  Ser  Thr  Val  Asp  Leu  Ala  Ser  Lys  Val  Lys
          755                      760                     765

Leu  Pro  Glu  Gly  His  Tyr  Arg  Val  Gly  Ser  Arg  Ala  Ile  Tyr  Thr  Cys
     770                      775                     780

Glu  Ser  Arg  Tyr  Tyr  Glu  Leu  Leu  Gly  Ser  Gln  Gly  Arg  Arg  Cys  Asp
785                      790                     795                          800

Ser  Asn  Gly  Asn  Trp  Ser  Gly  Arg  Pro  Ala  Ser  Cys  Ile  Pro  Val  Cys
                    805                     810                     815

Gly  Arg  Ser  Asp  Ser  Pro  Arg  Ser  Pro  Phe  Ile  Trp  Asn  Gly  Asn  Ser
               820                      825                     830

Thr  Glu  Ile  Gly  Gln  Trp  Pro  Trp  Gln  Ala  Gly  Ile  Ser  Arg  Trp  Leu
          835                      840                     845

Ala  Asp  His  Asn  Met  Trp  Phe  Leu  Gln  Cys  Gly  Gly  Ser  Leu  Leu  Asn
850                           855                     860

Glu  Lys  Trp  Ile  Val  Thr  Ala  Ala  His  Cys  Val  Thr  Tyr  Ser  Ala  Thr
865                 870                      875                          880

Ala  Glu  Ile  Ile  Asp  Pro  Asn  Gln  Phe  Lys  Met  Tyr  Leu  Gly  Lys  Tyr
               885                      890                     895

Tyr  Arg  Asp  Asp  Ser  Arg  Asp  Asp  Tyr  Val  Gln  Val  Arg  Glu  Ala
               900                 905                     910

Leu  Glu  Ile  His  Val  Asn  Pro  Asn  Tyr  Asp  Pro  Gly  Asn  Leu  Asn  Phe
          915                      920                     925

Asp  Ile  Ala  Leu  Ile  Gln  Leu  Lys  Thr  Pro  Val  Thr  Leu  Thr  Thr  Arg
930                           935                     940

Val  Gln  Pro  Ile  Cys  Leu  Pro  Thr  Asp  Ile  Thr  Thr  Arg  Glu  His  Leu
945                      950                      955                          960

Lys  Glu  Gly  Thr  Leu  Ala  Val  Val  Thr  Gly  Trp  Gly  Leu  Asn  Glu  Asn
               965                      970                     975

Asn  Thr  Tyr  Ser  Glu  Thr  Ile  Gln  Gln  Ala  Val  Leu  Pro  Val  Val  Ala
               980                      985                     990

Ala  Ser  Thr  Cys  Glu  Glu  Gly  Tyr  Lys  Glu  Ala  Asp  Leu  Pro  Leu  Thr
          995                      1000                    1005

Val  Thr  Glu  Asn  Met  Phe  Cys  Ala  Gly  Tyr  Lys  Lys  Gly  Arg  Tyr  Asp
1010                          1015                    1020

Ala  Cys  Ser  Gly  Asp  Ser  Gly  Gly  Pro  Leu  Val  Phe  Ala  Asp  Asp  Ser
1025                1030                     1035                         1040

Arg  Thr  Glu  Arg  Arg  Trp  Val  Leu  Glu  Gly  Ile  Val  Ser  Trp  Gly  Ser
               1045                     1050                    1055

Pro  Ser  Gly  Cys  Gly  Lys  Ala  Asn  Gln  Tyr  Gly  Gly  Phe  Thr  Lys  Val
               1060                     1065                    1070

Asn  Val  Phe  Leu  Ser  Trp  Ile  Arg  Gln  Phe  Ile
          1075                     1080
```

( 2 ) INFORMATION FOR SEQ ID NO:3:

( i ) SEQUENCE CHARACTERISTICS:
        ( A ) LENGTH: 3448 base pairs
        ( B ) TYPE: nucleic acid
        ( C ) STRANDEDNESS: single
        ( D ) TOPOLOGY: both (ii) MOLECULE TYPE: cDNA (iii) HYPOTHETICAL: NO (iv) ANTI-SENSE: NO (vi) ORIGINAL SOURCE:
(A) ORGANISM: Carcinoscorpius rotundicauda (ix) FEATURE:
(A) NAME/KEY: CDS
(B) LOCATION: 18..3074

(xi) SEQUENCE DESCRIPTION: SEQ ID NO:3:

```
GTGAAGGTAA CTTAAGT ATG GTC TTA GCG TCG TTT TTG GTG TCT GGT TTA       50
                    Met Val Leu Ala Ser Phe Leu Val Ser Gly Leu
                     1               5                      10

GTT CTA GGG CTA CTA GCC CAA AAA ATG CGC CCA GTT CAG TCC AAA GGA       98
Val Leu Gly Leu Leu Ala Gln Lys Met Arg Pro Val Gln Ser Lys Gly
         15                  20                  25

GTA GAT CTA GGC TTG TGT GAT GAA ACG AGG TTC GAG TGT AAG TGT GGC      146
Val Asp Leu Gly Leu Cys Asp Glu Thr Arg Phe Glu Cys Lys Cys Gly
         30                  35                  40

GAT CCA GGC TAT GTG TTC AAC ATT CCA GTG AAA CAA TGT ACA TAC TTT      194
Asp Pro Gly Tyr Val Phe Asn Ile Pro Val Lys Gln Cys Thr Tyr Phe
         45                  50                  55

TAT CGA TGG AGG CCG TAT TGT AAA CCA TGT GAT GAC CTG GAG GCT AAG      242
Tyr Arg Trp Arg Pro Tyr Cys Lys Pro Cys Asp Asp Leu Glu Ala Lys
 60                  65                  70                  75

GAT ATT TGT CCA AAG TAC AAA CGA TGT CAA GAG TGT AAG GCT GGT CTT      290
Asp Ile Cys Pro Lys Tyr Lys Arg Cys Gln Glu Cys Lys Ala Gly Leu
                 80                  85                  90

GAT AGT TGT GTT ACT TGT CCA CCT AAC AAA TAT GGT ACT TGG TGT AGC      338
Asp Ser Cys Val Thr Cys Pro Pro Asn Lys Tyr Gly Thr Trp Cys Ser
             95                 100                 105

GGT GAA TGT CAG TGT AAG AAT GGA GGT ATC TGT GAC CAG AGG ACA GGA      386
Gly Glu Cys Gln Cys Lys Asn Gly Gly Ile Cys Asp Gln Arg Thr Gly
         110                 115                 120

GCT TGT GCA TGT CGT GAC AGA TAT GAA GGG GTG CAC TGT GAA ATT CTC      434
Ala Cys Ala Cys Arg Asp Arg Tyr Glu Gly Val His Cys Glu Ile Leu
     125                 130                 135

AAA GGT TGT CCT CTT CTT CCA TCG GAT TCT CAG GTT CAG GAA GTC AGA      482
Lys Gly Cys Pro Leu Leu Pro Ser Asp Ser Gln Val Gln Glu Val Arg
140                 145                 150                 155

AAT CCA CCA GAT AAT CCC CAA ACT ATT GAC TAC AGC TGT TCA CCA GGG      530
Asn Pro Pro Asp Asn Pro Gln Thr Ile Asp Tyr Ser Cys Ser Pro Gly
                 160                 165                 170

TTC AAG CTT AAG GGT ATG GCA CGA ATT AGC TGT CTC CCA AAT GGA CAG      578
Phe Lys Leu Lys Gly Met Ala Arg Ile Ser Cys Leu Pro Asn Gly Gln
             175                 180                 185

TGG AGT AAC TTT CCA CCC AAA TGT ATT CGA GAA TGT GCC ATG GTT TCA      626
Trp Ser Asn Phe Pro Pro Lys Cys Ile Arg Glu Cys Ala Met Val Ser
         190                 195                 200

TCT CCA GAA CAT GGG AAA GTG AAT GCT CTT AGT GGT GAT ATG ATA GAA      674
Ser Pro Glu His Gly Lys Val Asn Ala Leu Ser Gly Asp Met Ile Glu
205                 210                 215

GGG GCT ACT TTA CGG TTC TCA TGT GAT AGT CCC TAC TAC TTG ATT GGT      722
Gly Ala Thr Leu Arg Phe Ser Cys Asp Ser Pro Tyr Tyr Leu Ile Gly
220                 225                 230                 235

CAA GAA ACA TTA ACC TGT CAG GGT AAT GGT CAG TGG AAT GGA CAG ATA      770
Gln Glu Thr Leu Thr Cys Gln Gly Asn Gly Gln Trp Asn Gly Gln Ile
             240                 245                 250
```

| | | | | | | | | | | | | | | | | |
|---|---|---|---|---|---|---|---|---|---|---|---|---|---|---|---|---|
| CCA | CAA | TGT | AAG | AAC | TTG | GTC | TTC | TGT | CCT | GAC | CTG | GAT | CCT | GTA | AAC | 818 |
| Pro | Gln | Cys | Lys | Asn | Leu | Val | Phe | Cys | Pro | Asp | Leu | Asp | Pro | Val | Asn | |
| | | | 255 | | | | 260 | | | | | 265 | | | | |
| CAT | GCT | GAA | CAC | AAG | GTT | AAA | ATT | GGT | GTG | GAA | CAA | AAA | TAT | GGT | CAG | 866 |
| His | Ala | Glu | His | Lys | Val | Lys | Ile | Gly | Val | Glu | Gln | Lys | Tyr | Gly | Gln | |
| | | | 270 | | | | 275 | | | | | 280 | | | | |
| TTT | CCT | CAA | GGC | ACT | GAA | GTG | ACC | TAT | ACG | TGT | TCG | GGT | AAC | TAC | TTC | 914 |
| Phe | Pro | Gln | Gly | Thr | Glu | Val | Thr | Tyr | Thr | Cys | Ser | Gly | Asn | Tyr | Phe | |
| | | 285 | | | | | 290 | | | | | 295 | | | | |
| TTG | ATG | GGT | TTT | GAC | ACC | TTA | AAA | TGT | AAC | CCT | GAT | GGG | TCT | TGG | TCA | 962 |
| Leu | Met | Gly | Phe | Asp | Thr | Leu | Lys | Cys | Asn | Pro | Asp | Gly | Ser | Trp | Ser | |
| 300 | | | | | 305 | | | | | 310 | | | | | 315 | |
| GGA | TCA | CAG | CCA | TCC | TGT | GTT | AAA | GTG | GCA | GAC | AGA | GAG | GTC | GAC | TGT | 1010 |
| Gly | Ser | Gln | Pro | Ser | Cys | Val | Lys | Val | Ala | Asp | Arg | Glu | Val | Asp | Cys | |
| | | | | 320 | | | | | 325 | | | | | 330 | | |
| GAC | AGT | AAA | GCT | GTA | GAC | TTC | TTG | GAT | GAT | GTT | GGT | GAA | CCT | GTC | AGG | 1058 |
| Asp | Ser | Lys | Ala | Val | Asp | Phe | Leu | Asp | Asp | Val | Gly | Glu | Pro | Val | Arg | |
| | | | 335 | | | | | 340 | | | | | 345 | | | |
| ATC | CAC | TGT | CCT | GCT | GGC | TGT | TCT | TTG | ACA | GCT | GGT | ACT | GTG | TGG | GGT | 1106 |
| Ile | His | Cys | Pro | Ala | Gly | Cys | Ser | Leu | Thr | Ala | Gly | Thr | Val | Trp | Gly | |
| | | 350 | | | | | 355 | | | | | 360 | | | | |
| ACA | GCC | ATA | TAC | CAT | GAA | CTT | TCC | TCA | GTG | TGT | CGT | GCA | GCC | ATC | CAT | 1154 |
| Thr | Ala | Ile | Tyr | His | Glu | Leu | Ser | Ser | Val | Cys | Arg | Ala | Ala | Ile | His | |
| | 365 | | | | | 370 | | | | | 375 | | | | | |
| GCT | GGC | AAG | CTT | CCA | AAC | TCT | GGA | GGA | GCG | GTG | CAT | GTT | GTG | AAC | AAT | 1202 |
| Ala | Gly | Lys | Leu | Pro | Asn | Ser | Gly | Gly | Ala | Val | His | Val | Val | Asn | Asn | |
| 380 | | | | | 385 | | | | | 390 | | | | | 395 | |
| GGC | CCC | TAC | TCG | GAC | TTT | CTG | GGT | AGT | GAC | CTG | AAT | GGG | ATA | AAA | TCG | 1250 |
| Gly | Pro | Tyr | Ser | Asp | Phe | Leu | Gly | Ser | Asp | Leu | Asn | Gly | Ile | Lys | Ser | |
| | | | | 400 | | | | | 405 | | | | | 410 | | |
| GAA | GAG | TTG | AAG | TCT | CTT | GCC | CGG | AGT | TTC | CGA | TTC | GAT | TAT | GTC | CGT | 1298 |
| Glu | Glu | Leu | Lys | Ser | Leu | Ala | Arg | Ser | Phe | Arg | Phe | Asp | Tyr | Val | Arg | |
| | | | 415 | | | | | 420 | | | | | 425 | | | |
| TCC | TCC | ACA | GCA | GGT | AAA | TCA | GGA | TGT | CCT | GAT | GGA | TGG | TTT | GAG | GTA | 1346 |
| Ser | Ser | Thr | Ala | Gly | Lys | Ser | Gly | Cys | Pro | Asp | Gly | Trp | Phe | Glu | Val | |
| | | 430 | | | | | 435 | | | | | 440 | | | | |
| GAC | GAG | AAC | TGT | GTG | TAC | GTT | ACA | TCA | AAA | CAG | AGA | GCC | TGG | GAA | AGA | 1394 |
| Asp | Glu | Asn | Cys | Val | Tyr | Val | Thr | Ser | Lys | Gln | Arg | Ala | Trp | Glu | Arg | |
| | 445 | | | | | 450 | | | | | 455 | | | | | |
| GCT | CAA | GGT | GTG | TGT | ACC | AAT | ATG | GCT | GCT | CGT | CTT | GCT | GTG | CTG | GAC | 1442 |
| Ala | Gln | Gly | Val | Cys | Thr | Asn | Met | Ala | Ala | Arg | Leu | Ala | Val | Leu | Asp | |
| 460 | | | | | 465 | | | | | 470 | | | | | 475 | |
| AAA | GAT | GTA | ATT | CCA | AAT | TCG | TTG | ACT | GAG | ACT | CTA | CGA | GGG | AAA | GGG | 1490 |
| Lys | Asp | Val | Ile | Pro | Asn | Ser | Leu | Thr | Glu | Thr | Leu | Arg | Gly | Lys | Gly | |
| | | | | 480 | | | | | 485 | | | | | 490 | | |
| TTA | ACA | ACC | ACG | TGG | ATA | GGA | TTG | CAC | AGA | CTA | GAT | GCT | GAG | AAG | CCC | 1538 |
| Leu | Thr | Thr | Thr | Trp | Ile | Gly | Leu | His | Arg | Leu | Asp | Ala | Glu | Lys | Pro | |
| | | | 495 | | | | | 500 | | | | | 505 | | | |
| TTT | ATT | TGG | GAG | TTA | ATG | GAT | CGT | AGT | AAT | GTG | GTT | CTG | AAT | GAT | AAC | 1586 |
| Phe | Ile | Trp | Glu | Leu | Met | Asp | Arg | Ser | Asn | Val | Val | Leu | Asn | Asp | Asn | |
| | | | 510 | | | | | 515 | | | | | 520 | | | |
| CTA | ACA | TTC | TGG | GCC | TCT | GGC | GAA | CCT | GGA | AAT | GAA | ACT | AAC | TGT | GTA | 1634 |
| Leu | Thr | Phe | Trp | Ala | Ser | Gly | Glu | Pro | Gly | Asn | Glu | Thr | Asn | Cys | Val | |
| | 525 | | | | | 530 | | | | | 535 | | | | | |
| TAT | ATG | GAC | ATC | CAA | GAT | CAG | TTG | CAG | TCT | GTG | TGG | AAA | ACC | AAG | TCA | 1682 |
| Tyr | Met | Asp | Ile | Gln | Asp | Gln | Leu | Gln | Ser | Val | Trp | Lys | Thr | Lys | Ser | |
| 540 | | | | | 545 | | | | | 550 | | | | | 555 | |
| TGT | TTT | CAG | CCC | TCA | AGT | TTT | GCT | TGC | ATG | ATG | GAT | CTG | TCA | GAC | AGA | 1730 |
| Cys | Phe | Gln | Pro | Ser | Ser | Phe | Ala | Cys | Met | Met | Asp | Leu | Ser | Asp | Arg | |
| | | | | 560 | | | | | 565 | | | | | 570 | | |

| | | | | | | | | | | | | | | | | |
|---|---|---|---|---|---|---|---|---|---|---|---|---|---|---|---|---|
| AAT | AAA | GCC | AAA | TGC | GAT | GAT | CCT | GGA | TCA | CTG | GAA | AAT | GGA | CAC | GCC | 1778 |
| Asn | Lys | Ala | Lys 575 | Cys | Asp | Asp | Pro 580 | Gly | Ser | Leu | Glu | Asn 585 | Gly | His | Ala | |
| ACA | CTT | CAT | GGA | CAA | AGT | ATT | GAT | GGG | TTC | TAT | GCT | GGT | TCT | TCT | ATA | 1826 |
| Thr | Leu | His 590 | Gly | Gln | Ser | Ile | Asp 595 | Gly | Phe | Tyr | Ala | Gly 600 | Ser | Ser | Ile | |
| AGG | TAC | AGC | TGT | GAG | GTT | CTC | CAC | TAC | CTC | AGT | GGA | ACT | GAA | ACC | GTA | 1874 |
| Arg | Tyr 605 | Ser | Cys | Glu | Val | Leu 610 | His | Tyr | Leu | Ser | Gly 615 | Thr | Glu | Thr | Val | |
| ACT | TGT | ACA | ACA | AAT | GGC | ACA | TGG | AGT | GCT | CCT | AAA | CCT | CGA | TGT | ATC | 1922 |
| Thr 620 | Cys | Thr | Thr | Asn | Gly 625 | Thr | Trp | Ser | Ala | Pro 630 | Lys | Pro | Arg | Cys | Ile 635 | |
| AAA | GTC | ATC | ACC | TGC | CAA | AAC | CCC | CCT | GTA | CCA | TCA | TAT | GGT | TCT | GTG | 1970 |
| Lys | Val | Ile | Thr | Cys 640 | Gln | Asn | Pro | Pro | Val 645 | Pro | Ser | Tyr | Gly | Ser 650 | Val | |
| GAA | ATC | AAA | CCC | CCA | AGT | CGG | ACA | AAC | TCG | ATA | AGT | CGT | GTT | GGG | TCA | 2018 |
| Glu | Ile | Lys | Pro 655 | Pro | Ser | Arg | Thr | Asn 660 | Ser | Ile | Ser | Arg | Val 665 | Gly | Ser | |
| CCT | TTC | TTG | AGG | TTG | CCA | CGG | TTA | CCC | CTC | CCA | TTA | GCT | AGA | GCA | GCC | 2066 |
| Pro | Phe | Leu 670 | Arg | Leu | Pro | Arg | Leu 675 | Pro | Leu | Pro | Leu | Ala 680 | Arg | Ala | Ala | |
| AAA | CCT | CCT | CCA | AAA | CCT | AGA | TCC | TCA | CAA | CCC | TCT | ACT | GTG | GAC | TTG | 2114 |
| Lys | Pro | Pro | Pro 685 | Lys | Pro | Arg | Ser | Ser 690 | Gln | Pro | Ser | Thr | Val 695 | Asp | Leu | |
| GCT | TCT | AAA | GTT | AAA | CTA | CCT | GAA | GGT | CAT | TAC | CGG | GTA | GGG | TCT | CGA | 2162 |
| Ala | Ser | Lys | Val | Lys 705 | Leu | Pro | Glu | Gly | His 710 | Tyr | Arg | Val | Gly | Ser 715 | Arg | |
| 700 | | | | | | | | | | | | | | | | |
| GCC | ATC | TAC | ACG | TGC | GAG | TCG | AGA | TAC | TAC | GAA | CTA | CTT | GGA | TCT | CAA | 2210 |
| Ala | Ile | Tyr | Thr | Cys 720 | Glu | Ser | Arg | Tyr | Tyr 725 | Glu | Leu | Leu | Gly | Ser 730 | Gln | |
| GGC | AGA | AGA | TGT | GAC | TCT | AAT | GGA | AAC | TGG | AGT | GGT | CGG | CCA | GCG | AGC | 2258 |
| Gly | Arg | Arg | Cys 735 | Asp | Ser | Asn | Gly | Asn 740 | Trp | Ser | Gly | Arg | Pro 745 | Ala | Ser | |
| TGT | ATT | CCA | GTT | TGT | GGA | CGG | TCA | GAC | TCT | CCT | CGT | TCT | CCT | TTT | ATC | 2306 |
| Cys | Ile | Pro | Val 750 | Cys | Gly | Arg | Ser | Asp 755 | Ser | Pro | Arg | Ser | Pro 760 | Phe | Ile | |
| TGG | AAT | GGG | AAT | TCT | ACA | GAA | ATA | GGT | CAG | TGG | CCG | TGG | CAG | GCA | GGA | 2354 |
| Trp | Asn | Gly 765 | Asn | Ser | Thr | Glu | Ile 770 | Gly | Gln | Trp | Pro | Trp 775 | Gln | Ala | Gly | |
| ATC | TCT | AGA | TGG | CTT | GCA | GAC | CAC | AAT | ATG | TGG | TTT | CTC | CAG | TGT | GGA | 2402 |
| Ile | Ser | Arg | Trp 780 | Leu | Ala | Asp | His | Asn 785 | Met | Trp | Phe | Leu | Gln 790 | Cys | Gly 795 | |
| GGA | TCT | CTA | TTG | AAT | GAG | AAA | TGG | ATC | GTC | ACT | GCT | GCC | CAC | TGT | GTC | 2450 |
| Gly | Ser | Leu | Leu | Asn 800 | Glu | Lys | Trp | Ile | Val 805 | Thr | Ala | Ala | His | Cys 810 | Val | |
| ACC | TAC | TCT | GCT | ACT | GCT | GAG | ATT | ATT | GAC | CCC | AAT | CAG | TTT | AAA | ATG | 2498 |
| Thr | Tyr | Ser | Ala 815 | Thr | Ala | Glu | Ile | Ile 820 | Asp | Pro | Asn | Gln | Phe 825 | Lys | Met | |
| TAT | CTG | GGC | AAG | TAC | TAC | CGT | GAT | GAC | AGT | AGA | GAC | GAT | GAC | TAT | GTA | 2546 |
| Tyr | Leu | Gly 830 | Lys | Tyr | Tyr | Arg | Asp 835 | Asp | Ser | Arg | Asp | Asp 840 | Asp | Tyr | Val | |
| CAA | GTA | AGA | GAG | GCT | CTT | GAG | ATC | CAC | GTG | AAT | CCT | AAC | TAC | GAC | CCC | 2594 |
| Gln | Val | Arg 845 | Glu | Ala | Leu | Glu | Ile 850 | His | Val | Asn | Pro | Asn 855 | Tyr | Asp | Pro | |
| GGC | AAT | CTC | AAC | TTT | GAC | ATA | GCC | CTA | ATT | CAA | CTG | AAA | ACT | CCT | GTT | 2642 |
| Gly | Asn | Leu 860 | Asn | Phe | Asp | Ile | Ala 865 | Leu | Ile | Gln | Leu | Lys 870 | Thr | Pro | Val 875 | |
| ACT | TTG | ACA | ACA | CGA | GTC | CAA | CCA | ATC | TGT | CTG | CCT | ACT | GAC | ATC | ACA | 2690 |
| Thr | Leu | Thr | Thr | Arg 880 | Val | Gln | Pro | Ile | Cys 885 | Leu | Pro | Thr | Asp | Ile 890 | Thr | |

| | | | | | | | | | | | | | | | | |
|---|---|---|---|---|---|---|---|---|---|---|---|---|---|---|---|---|
| ACA | AGA | GAA | CAC | TTG | AAG | GAG | GGA | ACA | TTA | GCA | GTG | GTG | ACA | GGT | TGG | 2738 |
| Thr | Arg | Glu | His 895 | Leu | Lys | Glu | Gly | Thr 900 | Leu | Ala | Val | Val | Thr 905 | Gly | Trp | |
| GGT | TTG | AAT | GAA | AAC | AAC | ACC | TAT | TCA | GAG | ACG | ATT | CAA | CAA | GCT | GTG | 2786 |
| Gly | Leu | Asn 910 | Glu | Asn | Asn | Thr | Tyr 915 | Ser | Glu | Thr | Ile | Gln 920 | Gln | Ala | Val | |
| CTA | CCT | GTT | GTT | GCA | GCC | AGC | ACC | TGT | GAA | GAG | GGG | TAC | AAG | GAA | GCA | 2834 |
| Leu | Pro 925 | Val | Val | Ala | Ala | Ser 930 | Thr | Cys | Glu | Glu | Gly 935 | Tyr | Lys | Glu | Ala | |
| GAC | TTA | CCA | CTG | ACA | GTA | ACA | GAG | AAC | ATG | TTC | TGT | GCA | GGT | TAC | AAG | 2882 |
| Asp 940 | Leu | Pro | Leu | Thr | Val 945 | Thr | Glu | Asn | Met | Phe 950 | Cys | Ala | Gly | Tyr | Lys 955 | |
| AAG | GGA | CGT | TAT | GAT | GCC | TGC | AGT | GGG | GAC | AGT | GGA | GGA | CCT | TTA | GTG | 2930 |
| Lys | Gly | Arg | Tyr | Asp 960 | Ala | Cys | Ser | Gly | Asp 965 | Ser | Gly | Gly | Pro | Leu 970 | Val | |
| TTT | GCT | GAT | GAT | TCC | CGT | ACC | GAA | AGG | CGG | TGG | GTC | TTG | GAA | GGG | ATT | 2978 |
| Phe | Ala | Asp | Asp 975 | Ser | Arg | Thr | Glu | Arg 980 | Arg | Trp | Val | Leu | Glu 985 | Gly | Ile | |
| GTC | AGC | TGG | GGC | AGT | CCC | AGT | GGA | TGT | GGC | AAG | GCG | AAC | CAG | TAC | GGG | 3026 |
| Val | Ser | Trp 990 | Gly | Ser | Pro | Ser | Gly 995 | Cys | Gly | Lys | Ala | Asn 1000 | Gln | Tyr | Gly | |
| GGC | TTC | ACT | AAA | GTT | AAC | GTT | TTC | CTG | TCA | TGG | ATT | AGG | CAG | TTC | ATT | 3074 |
| Gly | Phe | Thr 1005 | Lys | Val | Asn | Val | Phe 1010 | Leu | Ser | Trp | Ile | Arg 1015 | Gln | Phe | Ile | |

| | | | | |
|---|---|---|---|---|
| TGAAACTGAT | CTAAATATTT | TAAGCATGGT | TATAAACGTC | TTGTTTCCTA | TTATTGCTTT | 3134 |
| ACTAGTTTAA | CCCATAAGAA | GGTTAACTGG | GTAAGGCACA | AGGATCATTG | TTTCTGTTTG | 3194 |
| TTTTTACAAA | TGGTTATTTT | AGTCAGTGAA | TGAGAATAGT | ATCCATTGAA | GACTGTTACC | 3254 |
| TTTTATTCTA | CCTTTTTATA | TTACTATGTA | AGTATTGGG | ATATCTTCTA | CACATGAAAA | 3314 |
| TTCTGTCATT | TTACCATAAA | TTTGGTTTCT | GGTGTGTGCT | AAGTCCACCA | GTAGAGAACG | 3374 |
| ATGTAATTTT | CACTAGCACA | TGAAATAAAT | ATAGAACAAA | TCTATTATAA | ACTACCTTAA | 3434 |
| AAAAAAAAAA | AAAA | | | | | 3448 |

( 2 ) INFORMATION FOR SEQ ID NO:4:

( i ) SEQUENCE CHARACTERISTICS:
        ( A ) LENGTH: 1019 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Val | Leu | Ala | Ser 5 | Phe | Leu | Val | Ser | Gly 10 | Leu | Val | Leu | Gly 15 | Leu |
| Ala | Gln | Lys | Met 20 | Arg | Pro | Val | Gln | Ser 25 | Lys | Gly | Val | Asp | Leu 30 | Gly | Leu |
| Cys | Asp | Glu | Thr 35 | Arg | Phe | Glu | Cys 40 | Lys | Cys | Gly | Asp | Pro 45 | Gly | Tyr | Val |
| Phe | Asn 50 | Ile | Pro | Val | Lys | Gln 55 | Cys | Thr | Tyr | Phe | Tyr 60 | Arg | Trp | Arg | Pro |
| Tyr 65 | Cys | Lys | Pro | Cys | Asp 70 | Asp | Leu | Glu | Ala | Lys 75 | Asp | Ile | Cys | Pro | Lys 80 |
| Tyr | Lys | Arg | Cys | Gln 85 | Glu | Cys | Lys | Ala | Gly 90 | Leu | Asp | Ser | Cys | Val 95 | Thr |
| Cys | Pro | Pro | Asn 100 | Lys | Tyr | Gly | Thr | Trp 105 | Cys | Ser | Gly | Glu | Cys 110 | Gln | Cys |
| Lys | Asn | Gly | Gly | Ile | Cys | Asp | Gln | Arg | Thr | Gly | Ala | Cys | Ala | Cys | Arg |

-continued

```
              115                        120                        125
Asp  Arg  Tyr  Glu  Gly  Val  His  Cys  Glu  Ile  Leu  Lys  Gly  Cys  Pro  Leu
     130                       135                       140
Leu  Pro  Ser  Asp  Ser  Gln  Val  Gln  Glu  Val  Arg  Asn  Pro  Pro  Asp  Asn
145                      150                       155                       160
Pro  Gln  Thr  Ile  Asp  Tyr  Ser  Cys  Ser  Pro  Gly  Phe  Lys  Leu  Lys  Gly
                    165                       170                       175
Met  Ala  Arg  Ile  Ser  Cys  Leu  Pro  Asn  Gly  Gln  Trp  Ser  Asn  Phe  Pro
               180                       185                       190
Pro  Lys  Cys  Ile  Arg  Glu  Cys  Ala  Met  Val  Ser  Ser  Pro  Glu  His  Gly
          195                       200                       205
Lys  Val  Asn  Ala  Leu  Ser  Gly  Asp  Met  Ile  Glu  Gly  Ala  Thr  Leu  Arg
     210                       215                       220
Phe  Ser  Cys  Asp  Ser  Pro  Tyr  Tyr  Leu  Ile  Gly  Gln  Glu  Thr  Leu  Thr
225                      230                       235                       240
Cys  Gln  Gly  Asn  Gly  Gln  Trp  Asn  Gly  Gln  Ile  Pro  Gln  Cys  Lys  Asn
                    245                       250                       255
Leu  Val  Phe  Cys  Pro  Asp  Leu  Asp  Pro  Val  Asn  His  Ala  Glu  His  Lys
               260                       265                       270
Val  Lys  Ile  Gly  Val  Glu  Gln  Lys  Tyr  Gly  Gln  Phe  Pro  Gln  Gly  Thr
          275                       280                       285
Glu  Val  Thr  Tyr  Thr  Cys  Ser  Gly  Asn  Tyr  Phe  Leu  Met  Gly  Phe  Asp
     290                       295                       300
Thr  Leu  Lys  Cys  Asn  Pro  Asp  Gly  Ser  Trp  Ser  Gly  Ser  Gln  Pro  Ser
305                      310                       315                       320
Cys  Val  Lys  Val  Ala  Asp  Arg  Glu  Val  Asp  Cys  Asp  Ser  Lys  Ala  Val
                    325                       330                       335
Asp  Phe  Leu  Asp  Asp  Val  Gly  Glu  Pro  Val  Arg  Ile  His  Cys  Pro  Ala
               340                       345                       350
Gly  Cys  Ser  Leu  Thr  Ala  Gly  Thr  Val  Trp  Gly  Thr  Ala  Ile  Tyr  His
          355                       360                       365
Glu  Leu  Ser  Ser  Val  Cys  Arg  Ala  Ala  Ile  His  Ala  Gly  Lys  Leu  Pro
     370                       375                       380
Asn  Ser  Gly  Gly  Ala  Val  His  Val  Val  Asn  Asn  Gly  Pro  Tyr  Ser  Asp
385                      390                       395                       400
Phe  Leu  Gly  Ser  Asp  Leu  Asn  Gly  Ile  Lys  Ser  Glu  Glu  Leu  Lys  Ser
                    405                       410                       415
Leu  Ala  Arg  Ser  Phe  Arg  Phe  Asp  Tyr  Val  Arg  Ser  Ser  Thr  Ala  Gly
               420                       425                       430
Lys  Ser  Gly  Cys  Pro  Asp  Gly  Trp  Phe  Glu  Val  Asp  Glu  Asn  Cys  Val
          435                       440                       445
Tyr  Val  Thr  Ser  Lys  Gln  Arg  Ala  Trp  Glu  Arg  Ala  Gln  Gly  Val  Cys
     450                       455                       460
Thr  Asn  Met  Ala  Ala  Arg  Leu  Ala  Val  Leu  Asp  Lys  Asp  Val  Ile  Pro
465                      470                       475                       480
Asn  Ser  Leu  Thr  Glu  Thr  Leu  Arg  Gly  Lys  Gly  Leu  Thr  Thr  Thr  Trp
                    485                       490                       495
Ile  Gly  Leu  His  Arg  Leu  Asp  Ala  Glu  Lys  Pro  Phe  Ile  Trp  Glu  Leu
               500                       505                       510
Met  Asp  Arg  Ser  Asn  Val  Val  Leu  Asn  Asp  Asn  Leu  Thr  Phe  Trp  Ala
          515                       520                       525
Ser  Gly  Glu  Pro  Gly  Asn  Glu  Thr  Asn  Cys  Val  Tyr  Met  Asp  Ile  Gln
     530                       535                       540
```

```
Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Ser Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
        595                 600                 605

Val Leu His Tyr Leu Ser Gly Thr Glu Thr Val Thr Cys Thr Thr Asn
    610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655

Ser Arg Thr Asn Ser Ile Ser Arg Val Gly Ser Pro Phe Leu Arg Leu
            660                 665                 670

Pro Arg Leu Pro Leu Pro Leu Ala Arg Ala Ala Lys Pro Pro Pro Lys
        675                 680                 685

Pro Arg Ser Ser Gln Pro Ser Thr Val Asp Leu Ala Ser Lys Val Lys
    690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
            740                 745                 750

Gly Arg Ser Asp Ser Pro Arg Ser Pro Phe Ile Trp Asn Gly Asn Ser
    755                 760                 765

Thr Glu Ile Gly Gln Trp Pro Trp Gln Ala Gly Ile Ser Arg Trp Leu
770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Asn Gln Phe Lys Met Tyr Leu Gly Lys Tyr
            820                 825                 830

Tyr Arg Asp Asp Ser Arg Asp Asp Asp Tyr Val Gln Val Arg Glu Ala
    835                 840                 845

Leu Glu Ile His Val Asn Pro Asn Tyr Asp Pro Gly Asn Leu Asn Phe
850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu
                885                 890                 895

Lys Glu Gly Thr Leu Ala Val Val Thr Gly Trp Gly Leu Asn Glu Asn
            900                 905                 910

Asn Thr Tyr Ser Glu Thr Ile Gln Gln Ala Val Leu Pro Val Val Ala
    915                 920                 925

Ala Ser Thr Cys Glu Glu Gly Tyr Lys Glu Ala Asp Leu Pro Leu Thr
930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975
```

| | | | | | | | | | | | | | | |
|---|---|---|---|---|---|---|---|---|---|---|---|---|---|---|
| Arg | Thr | Glu | Arg 980 | Arg | Trp | Val | Leu | Glu 985 | Gly | Ile | Val | Ser | Trp 990 | Gly | Ser |
| Pro | Ser | Gly 995 | Cys | Gly | Lys | Ala | Asn | Gln 1000 | Tyr | Gly | Gly | Phe | Thr 1005 | Lys | Val |
| Asn | Val | Phe 1010 | Leu | Ser | Trp | Ile | Arg 1015 | Gln | Phe | Ile | | | | | |